(12) United States Patent
Kim et al.

(10) Patent No.: US 6,846,913 B1
(45) Date of Patent: Jan. 25, 2005

(54) **CRUDE EXTRACT FROM *VISCUM ALBUM COLORATUM*, AND PROTEINS AND LECTINS ISOLATED THEREFROM**

(75) Inventors: Jongbae Kim, Pohang-si (KR); Seongkyu Song, Pohang-si (KR); Byungsun Suh, Pohang-si (KR); Kwanhee Lee, Pohang-si (KR); Myoungsool Doo, Pohang-si (KR); Jinhwan Kwak, Pohang-si (KR); Byeoungdoo Song, Pohang-si (KR); Taekjoon Yoon, Goyang-si (KR); Taebong Kang, Pohang-si (KR); Choonho Park, Pohang-si (KR)

(73) Assignee: Mistle Biotech Co., Ltd., Pohang-si (KR)

( * ) Notice: Subject to any disclaimer, the term of this patent is extended or adjusted under 35 U.S.C. 154(b) by 332 days.

(21) Appl. No.: 09/627,165

(22) Filed: Jul. 27, 2000

(30) Foreign Application Priority Data

Jul. 27, 1999 (KR) ........................................ 1999-30638

(51) Int. Cl.⁷ .......................... A61K 38/16; C07K 14/00
(52) U.S. Cl. .................... 530/396; 530/350; 530/387.1; 514/8; 514/2; 514/12; 536/23.6; 435/320.1; 435/252.1; 435/325
(58) Field of Search .................... 514/8, 2, 12; 530/396, 530/350, 387.1; 536/23.6, 23.1; 435/320.1, 252.1, 325

(56) References Cited

U.S. PATENT DOCUMENTS 5,565,200 A    10/1996    Khwaja

OTHER PUBLICATIONS

Khwaja et al. (Proc. Am. Assoc. Cancer Res. Annu. Meet. 28, 303 (1987)).*
Yoon et al., International J. Immunopharmacology 20, 163–172 (Apr.–May 1998).*

* cited by examiner

Primary Examiner—Christopher S. F. Low
Assistant Examiner—Chih-Min Kam
(74) Attorney, Agent, or Firm—Nath & Associates PLLC; Gary M. Nath; Lee C. Heiman

(57) ABSTRACT

Disclosed is an extract from Korean mistletoe KM-110, which is of immunity enhancement and activity against tumor metastasis and can be used as an adjuvant material for vaccines applicable for the induction of humoral and cell-mediated immunity. Also disclosed are its fractions, a protein fraction KM-AS, a lectin fraction KML-C, lectin components KML-IIU and KML-IIL, which both are further purified from lectin fraction KML-C, a protein KMHBP which is obtained through heparin binding chromatography eluting with NaCl from a fraction C-free AS which is a portion of the KM-AS free of KML-C, and a mixture KM of the KMHBP and the KML-C. They are revealed as to their roles in the humoral and cell-mediated immunity enhancement and antitumoral activity.

3 Claims, 24 Drawing Sheets

Fig. 5
A) Induction of IL-1 by KM-100 in various doses
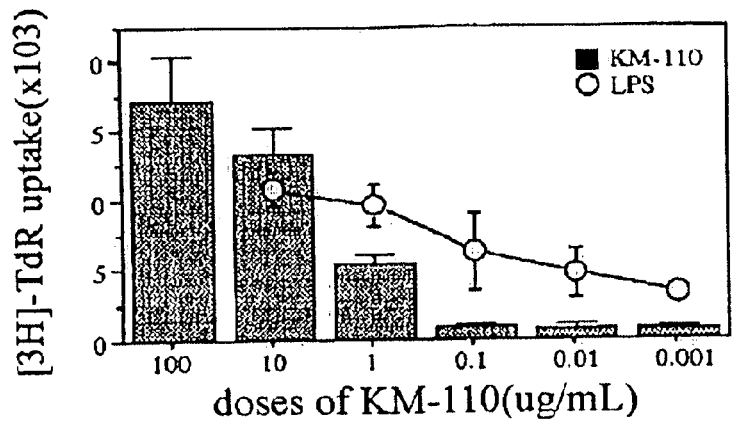
B) Time course of the induction of IL-1 by KM-110
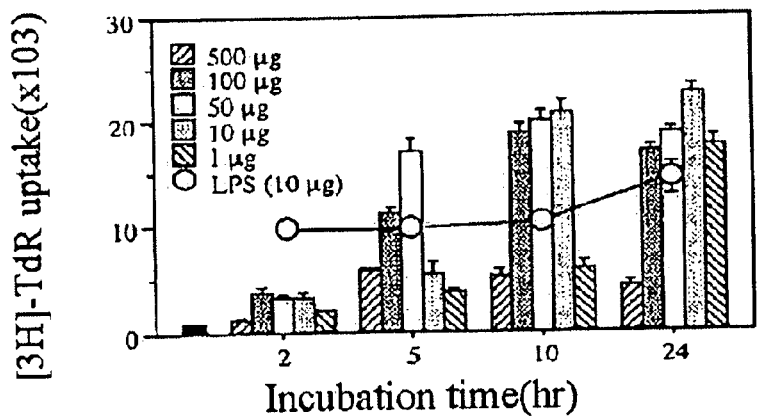
C) Time course of the induction of IL-1 by KM-AS
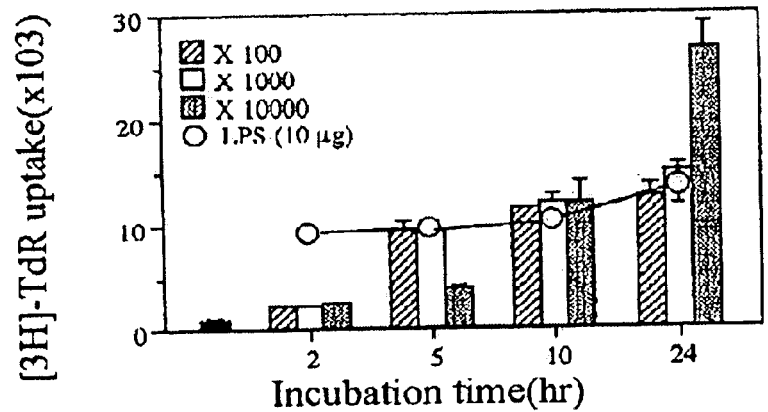

Fig. 8
1) TNF-α
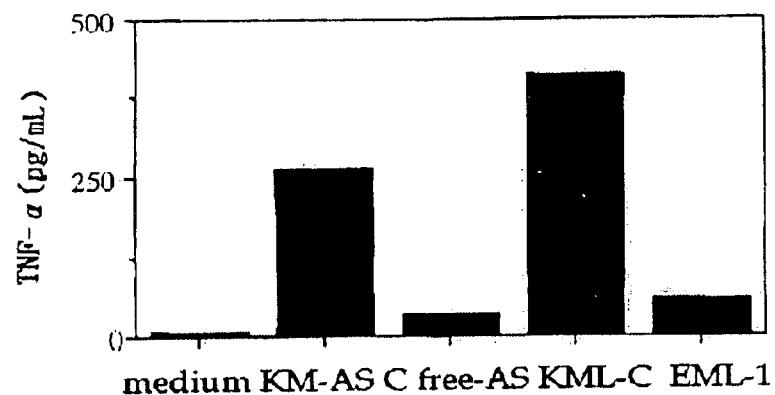
2) IL-6
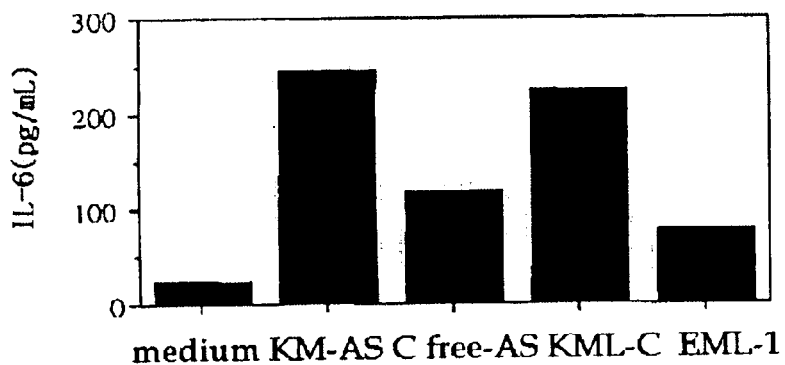
3) IFN-γ
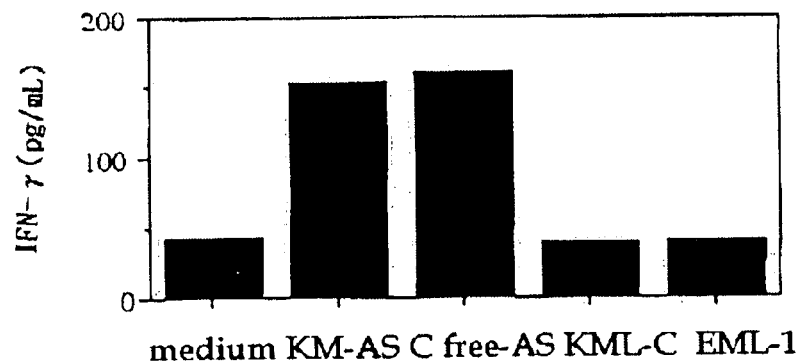

Fig. 12
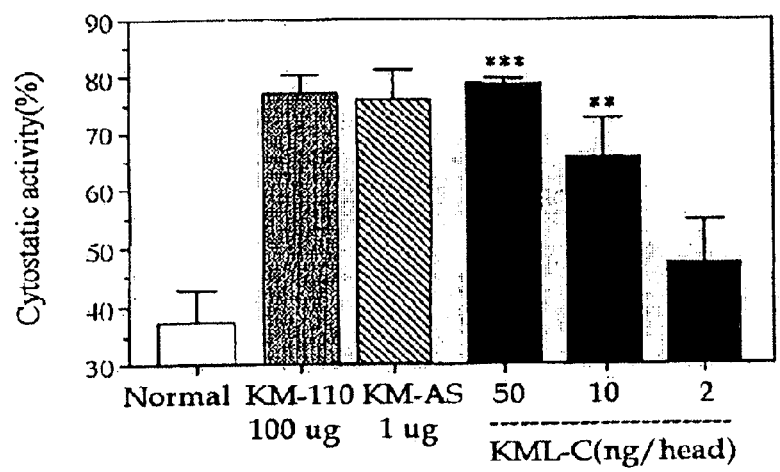
1) E/T ratio : 100
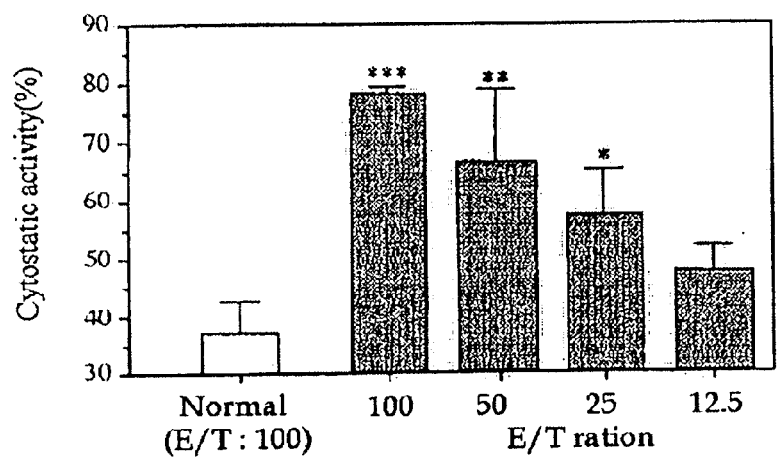
2) KML-C : 50 ng/head

Fig. 18 a/c
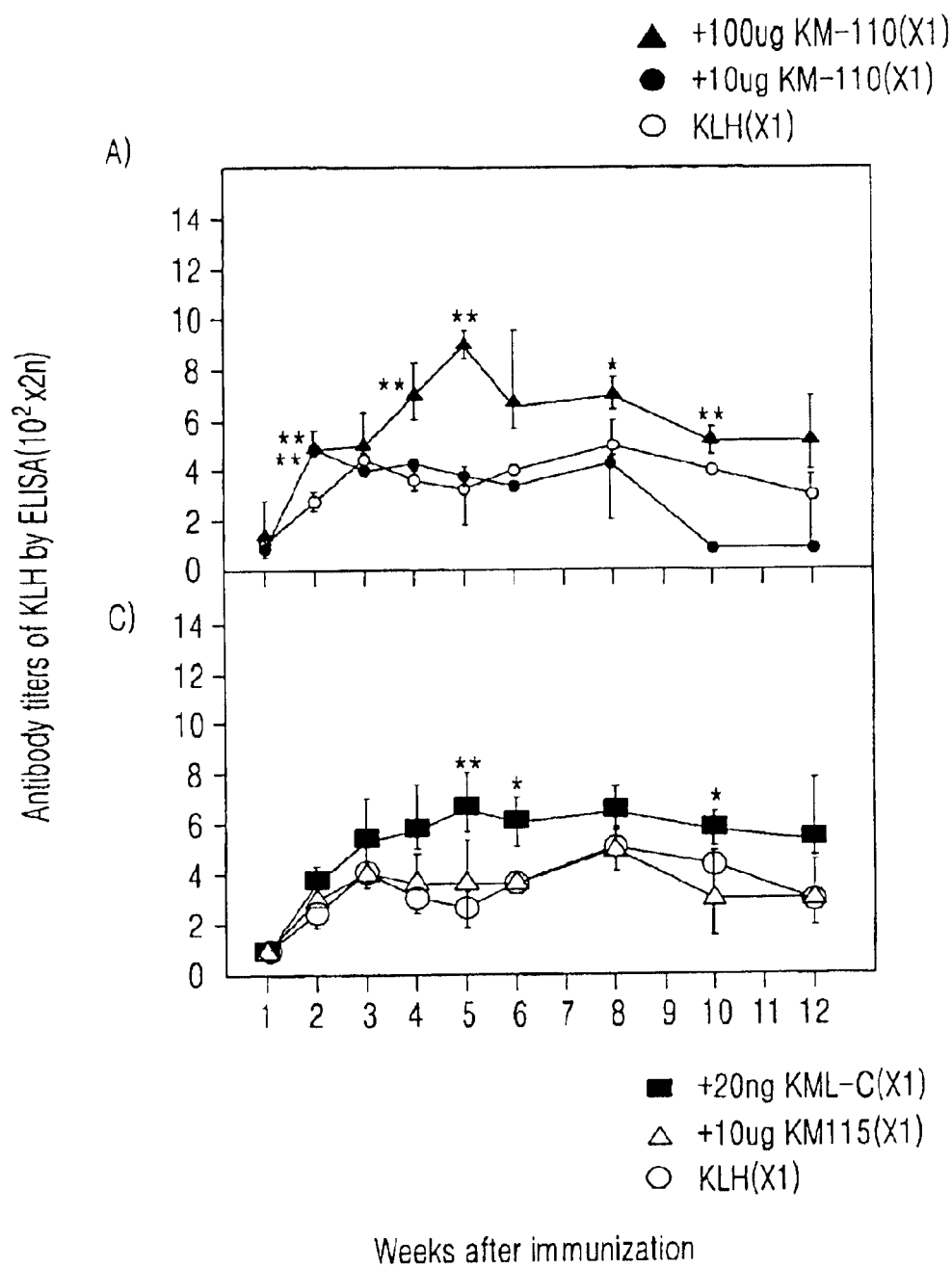

Fig. 18 b/d
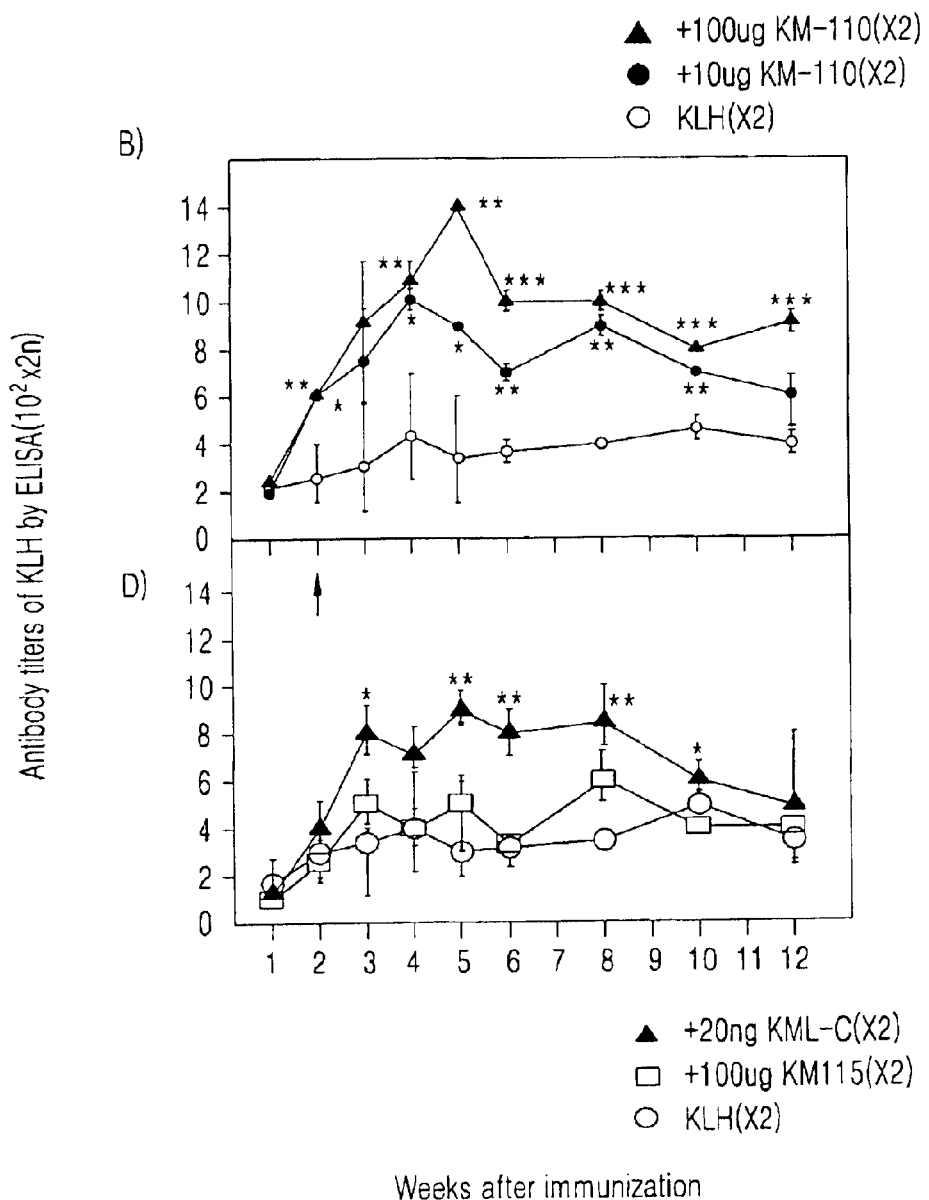

Concentration of lectin(ng/mL)

CRUDE EXTRACT FROM VISCUM ALBUM COLORATUM, AND PROTEINS AND LECTINS ISOLATED THEREFROM

FIELD OF THE INVENTION

The present invention relates, in general, to a crude extract from *Viscum album coloratum* and proteins and lectins isolated therefrom. More particularly, the present invention relates to an extract from *Viscum album coloratum* which enhances biological immunity with antitumoral activity and can be applied for an adjuvant to induce cell-mediated immunity. Also, the present invention is concerned with proteins and lectins which are present as a medicinally effective ingredients in the extract.

BACKGROUND OF THE INVENTION

Mistletoe, scientifically named Viscum album, is a semi-parasitic plant that lives in or on various tree hosts, from the body of which it obtains nutriment, and as many as about 1,500 species thereof, which belong to about 30 genuses, are now known to be present over the world. Of various mistletoes, the species belonging to the genus *Viscum*, especially *Viscum album loranthacea* that inhabits European areas, are used as medicinal materials. From a long time ago, such European loranthacea mistletoe had been used as a mysterious folk remedy curative of hypertension, arteriosclerosis, cancers, etc. In 1921, the *loranthacea* mistletoe was acknowledged to be of anticancer activity nd, from then, has been used as a curative or a therapeutical aid against tumors.

Accordingly, active research has been directed mainly to the biological activity of the European mistletoes, reporting that they have the immunity enhancement effect of stimulating humoral and cell-mediated immune systems as well as activate macrophages and natural killer cells, both taking direct and indirect parts in controlling tumor cells, to inhibit the growth of tumor cells and improve the viability of patients suffering from cancers. Also, mistletoe is found to exert cytotoxicity directly on tumor cells. Representative of active materials of mistletoe are lectin components, which are divided into letin-I, -II and III according to sugar chain specificity and molecular weight. Immunological and biochemical attention is being paid largely to lectin-I.

Korean mistletoe (*viscum album coloratum*), distinguishable from European mistletoe, has been used as medicinal materials effective for the treatment of lumbago, hypertension and teethache and the prevention of miscarriage in Korean folk remedies and Oriental herb medicine. Particularly, in Oriental herb medicine, different names are given to mistletoes in accordance with the kinds of the host trees, suggesting that there might be differences in medicinal efficacy and effective component between the mistletoes which grow in or on different host trees. As a matter of fact, European mistletoes were reported to be different from one to another in lectin components in accordance with their host trees. Hence, the possibility cannot exclude that Korean mistletoes might be also different in components on account of their different host trees.

On the basis of such possibility, Khwaja et al. reported the anti-tumor effects and active components of Korean mistletoes for the first time in Korea, asserting that, unlike European mistletoes, the anti-tumor effects of Korean mistletoes come from the cytotoxicity attributable to alkaloids of strong toxicity rather than from lectins and thus, Korean mistletoes are quite different from European ones in active components against tumors and anti-tumor activity mechanism. However, no details for the difference have yet been reported.

Recent research of the present inventors has demonstrated that Korean mistletoes also directly activated macrophages to induce the secretion of interleukin-1 (hereinafter referred to as "IL-1")and tumor necrosis factor-α (hereinafter referred to as "TNF-α") and that the activators to induce the secretion of these cytokines are proteinaceous ingredients which are precipitated by mmonium sulphate. In result, two kinds of lectins were isolated from Korean mistletoes.

SUMMARY OF THE INVENTION

Therefore, it is an object of the present invention to provide an extract from Korean mistletoe, which is of immunity enhancement and activity against tumor metastasis and can be used as an adjuvant material for vaccines applicable for the induction of cell-mediated immunity.

It is another object of the present invention to provide protein fractions and lectin fractions, which both are present as immunologically effective ingredients in the extract from Korean mistletoe.

It is a further object of the present invention to provide DNA base sequences coding for the lectins extracted from Korean mistletoe.

BRIEF DESCRIPTION OF THE INVENTION

FIGS. 2A–2C show the cytotoxicity effects of KM-110 and KM-AS over B16-BL6 (A), Raji (B) and normal lymphocyte (C).

FIGS. 5A–5C show the IL-1 induction by KM-110 (A and B) and KM-AS (C).

FIG. 6 shows the IL-1 induction activity by KML-C isolated from KM-AS.

FIGS. 8-1, 8-2 and 8-3 show the activity of KM-110, KML-C, EML-1 and C-free AS to secrete TNF-α, IL-C and IFN-γ.

FIGS. 12-1 and 12-2 show the NK-cell activity induced KML-C against the cell proliferation of YAC-1.

FIGS. 18A–18D show the effects of KM-110 and KML-C on the antibody production of KLH.

FIGS. 31-1, 31-2 and 31-3 show the comparison in the antibody production against HBV among KML-110, KML-IIU and KML-IIL.

DETAILED DESCRIPTION OF THE INVENTION

Figure 1A:
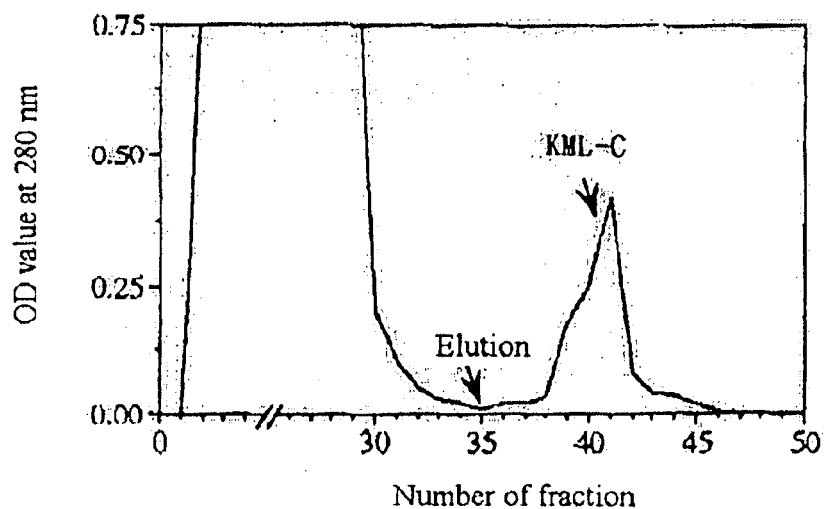
FIGS. 1A–1B show the isolation of the lectin fraction KML-C from the protein fraction KM-AS derived from the Korean mistletoe extract of the invention through a hydrolyzed sepharose-4B column in a chromatogram (A) and in an electrophoresis

One- or two-year-old Korean mistletoe is used as the substance of the present invention. Its leaves, stems and fruits are squashed in distilled water. The resulting solution is centrifuged and the supernatant is filtered by use of a membrane. The filtrate is freeze-dried to give a brown powder, which is designated "KM-110" hereinafter.

From KM-110, a protein fraction is obtained by precipitation using ammonium sulphate. KM-110 is added in a 70% saturated ammonium sulphate solution and allowed to precipitate by weakly stirring. The precipitate is purified by dialysis to give a protein fraction, called KM-AS.

Column chromatography is useful to further fractionate KM-AS. For this, a column is filled with sepharose-4B which is previously hydrolyzed with 0.2 M HCl and then, KM-AS is let to pass through the column. As an eluent, a solution of 0.1M lactose in PBS is used to collect fractions. The resulting eluate is further purified by dialysis to give a lectin component, call KML-C. Its molecular weight can be determined by SDS-PAGE.

In addition to electrophoresis, another electrophoretic method frequently used for characterizing proteins is based on differences in their isoelectric points. This method, called isoelectric focusing, is adapted to determine whether the Korean mistletoe lectin component KML-C is different from or identical to the European mistleto lectin component EML-I. As a result of isoelectric focusing, KML-C was revealed to be quite different from EML-I at least in isoelectric point.

$$$In order to investigate the immunological activity of KM-110 and KM-AS, they are applied to B16-BL6, Raji and a mouse lymphocytes, which are then subjected to cytotoxicity assay.

The relation with the mitogens for immune-competent cells is helpful in understanding the entity of KM-110 and its purified fractions KM-AS and KML-C. For this, a mitogen such as Con. A or LPS is applied to the immune-competent cells taken from mice which are already injected with the sample of interest, that is, KM-110, KM-AS or KML-C. Using radioactive labels, the DNA synthesis in the immune-competent cells is examined. Compared with normal mice, the mice administered with KM-110, KM-AS or KML-C are improved in the activity of DNA synthesis within mature immunocytes, but not within immature cells.

In connection with the enhancement of host immune defense, it is also needed to reveal how KM-110, KM-AS and KML-C function in the host. First, they are examined for cytokine induction. Macrophages are taken from the abdominal cells of mice and stimulated with the samples. After culturing, the culture media is examined for the secretion of IL-1 by ELISA. This examination is also applied for other cytokines, such as TNF-$\alpha$, IL-6 and IFN-$\gamma$. IL-1 is induced by all of the samples and, in particular, in a KML-C concentration-dependent pattern. Thus, KML-C is mainly responsible for the induction of IL-1. TNF-$\alpha$ and IL-6 is found to be induced by all of the samples. As for IFN-$\gamma$, it can be induced by KM-AS, but not by KML-C. Accordingly, it is required to identify the factor that induces IFN-$\gamma$.

For the isolation of the IFN-$\gamma$ inducer, a heparin column (Pharmacia) is employed. From C-free AS, which is a fraction of KM-AS free of KML-C, a protein fraction is isolated through the heparin column. As a test, the activity to induce IFN-$\gamma$ was detected largely from the fraction which was eluted by a phosphate buffer containing 100 mM NaCl. Thus, the ingredient of KM-110 which has the activity of inducing IFN-$\gamma$ is a Korean mistletoe heparin binding protein (KMHBP) fraction.

Next, KM-110, KML-C and KMHBP are examined for their safety in the body. After being intravenously injected ith the samples at various doses, mice are observed as to whether they die or can survive. The lethal dose $LD_{50}$ was estimated to be 1.0–1.5 mg/mouse (about 1.25 mg/mouse) for KM-110, about 12.5 $\mu$g/mouse for KM-AS, 1.25 $\mu$g/mouse for KML-C, and 50–100 $\mu$g/kg of body weight for KMHBP.

Whether KML-C has a repressive activity against tumor Metastasis is also examined. Regarding colon 26-M3.1 carcinoma, more than 5 ng of KML-C can prevent the metastasis of the cancer. This antitumoral activity of KML-C is also effective to L5178BY-ML25 lymphoma. The antitumoral activity of KML-C is believed to result from the direct cytotoxicity effect on tumor cells as well as the immunological stimulation to induce the activity of macrophages and NK-cells, which both are involved in the defense mechanism against tumors.

With regard to the enhancement of the host defense system, attention is turned to the tumor cell killing activity of macrophage. Macrophages taken from the mice administered with KML-C are co-cultured with tumor cells, such as B16-BL6 melanoma, after which the killing activity of the macrophages is observed. The tumor cell killing activity of macrophages is known to be carried out by secreting TNF-α or by bringing themselves into direct contact with tumor cells in addition to being related to the secretion of killing materials, in the inventors' estimation.

Following are the separation of lectin components from KML-C, and the characterization thereof. In addition, a description will be given of the genes coding for the lectin components.

To be used for the separation of lectin components later, anti-KML-C monoclonal antibodies are obtained by use of P3U1 myeloma. Through an antibody-specific ELISA experiment, there are obtained three types of antibodies: 9H7-D10 highly specific for KML-C, 8B11-2C5 with high cross-reactivity for KML-C and EML-I, and 8E12-3E9 with a positive reaction against KML-C. As for antibody subtype, 9H7-D10 and 8B11-2C5 both proved to be of an IgG1 type while 8E12-3E9 was of an IgM type.

By immuno-affinity column chromatography using these antibodies, two lectin components, respectively called "KML-IIU" and "KML-IIL", were obtained. They both are heterodimers consisting of two domains as analyzed by electrophoresis. In detail, KML-IIU is 61.8 kD in molecular weight, consisting of a 33.2 kD peptide chain and a 28.6 kD peptide chain while KML-IIL has a molecular weight of 56.4 kD composed of a 31 kD peptide chain and a 28.6 kD peptide chain. KML-IIU and KML-IIL are both restrained from hemagglutinating by lactose, galactose, and N-acetylgalactoseamine. On the other hand, the hemagglutination of EML-I is reported to be inhibited by lactose and galactose. Because none of Korean and European lectins are inhibited from hemagglutinating by glucose, a component composing lactose, the Korean mistletoe lectins separated according to the present invention are of specificity for galactose and N-acetylgalatoseamine.

To compare the amino acid sequences of KL-IIU and KML-IIL with that of EML-I, N-terminal amino acid sequencing was conducted. As a result of the amino acid sequence analysis, KML-IIU is believed to have a different structure from European lectins EML-I, -II and -III in terms of at least the amino acid sequence from the N-terminal to the 30$^{th}$ amino acid residue in one polypeptide chain. Also, KML-IIL is revealed to be quite different from the European lectins in amino acid sequence in the other polypeptide chain.

These lectins of the present invention are also tested for their immunity enhancement through the experiments concerning cytotoxicity, cytokine induction, and activity against tumor metastasis as in the above. In these experiments, the lectins KML-IIU and KML-IIL both prove to be immunologically effective materials.

Of the antibodies prepared above, 9H7-D10 antibody shows specific reactivity for KML-IIU without a cross-reaction with KML-IIL and EML-I while 8B11-2C5 antibody reacts with all of KML-IIU, KML-IIL and EML-1. On the basis of this result, 9H7-D10 antibody can neutralize the cytotoxicity of KML-IIU only, whereas 8B11-2C5 antibody is of cytotoxicity neutralization activity over KML-II, KML-IIL and EML-I. Thus, KML-IIU and KML-IIL are different in at least epitope from EML-1. In addition, 8B11-2C5 antibody shows cross-reactivity to all Korean and European lectins. Thus, KML-IIU and EML-I may be identical to each other or have remarkably similar epitopes. However, KML-IIL is a lectin different from EML-I when considering that KML-IIL is different in sugar specificity and B-chain amino acid sequence from EML-I in addition to having 10-folds more potent cytotoxicity than does EML-I.

The immunity enhancement action of KML-IIU and KML-IIL can be identified by the antibody productivity against an antigen. In this regard, the pre-S2 domain of hepatitis B virus (HBV), which is of pathogenicity, is used. Each lectin adjuvant shows higher antibody titer than does the control, aluminum hydroxide adjuvant in the first week after injection. Each lectin can induce higher initial immune responses than the alum adjuvant. In the second week after booster injection, KM-110 and KML-IIU were similar in antibody titer to the alum adjuvant, but KML-IIL shows an antibody titer twice larger than those of the other samples. Similar to the aluminum-based adjuvant in the aspect of maintaining antibody production, the adjuvants of the invention can induce antigen-specific antibody production until the fifth week of the initial immunization.

In order to molecular-biologically approach the lectins of the invention, portions of Korean mistletoe lectin genes were cloned. Based on the amino acid sequences of purified KML-IIU and KML-IIL, a set of two oligopeptides were designed as primers:

Primer 1: 5'-GTIACICAT CAIACIGG-3' (SEQ. ID. NO. 17)

Primer 2: 5'-ACIATICGC ACIFTIGGTC-3' (SEQ. ID. NO. 18)

From the genomic DNA of Korean mistletoe, a portion of the gene of interest was amplified by PCR. The clones obtained were base-sequenced. Some differences in base sequence among the clones suggest that there might exist various isoforms of Korean mistletoe. From the DNA base sequences, amino acid sequences can be deduced.

Using the extracts of the present invention, various adjuvants which show immunity enhancement activity can be prepared. For this, KM-110 is mixed with conventional adjuvants and the combined adjuvants are measured for the antibody titer against an antigen, such as mycoplasma. As a result, a significant immunological enhancement effect was obtained by adding KM-110 to conventional adjuvants, indicating that KM-110 can be used to prepare immunologically more effective adjuvants.

Next, the difference in the lectin content and thus, in the immunological effect of mistletoe extracts is considered according to the various host trees. The protein contents in various extracts are different from one host tree to another. In the mistletoes tested, *Prunus*-parasitic mistletoe contains the most abundant KML-C. Thus, the highest cytotoxicity is obtained from the the *Prunus*-parasitic mistletoe extract which was highest in lectin content, as measured by a lectin assay.

Because the lectin fraction KML-C can induce cytokines such as TNF-α, IL-1 and IL-6 while KMHBP shows IFN-γ induction activity, a mixture (KM) of KML-C and KMHBP can effectively induce all of the cytokines tested, TNF-α, IL-1, IFN-γ and IL-6. In addition, this mixture KM is greatly decreased in direct cytotoxicity on normal cells. Consequently, KM is improved not only in cytokine induction j us 15 activity, but also is safe to normal cells. In a test, the KM fraction, composed of KMHBP separated through a heparin column and KML-C, did not cause a sudden death in mice, so that the lethal material(s) is removed by the separation through the heparin column. KM is not different in the repressive activity against tumor metastasis from KM-110, so that it maintains the activity of KM-110 as it is.

A better understanding of the present invention may be obtained in light of the following examples which are set forth to illustrate, but are not to be construed to limit the present invention.

EXAMPLE 1

Extract of Korean Mistletoe and Protein Fraction Isolated Therefrom

Used were mistletoes that had been grown for one or two years in Korea before being gathered in January. From the plants were taken the leaves, stems and fruits within the stretch from branch ends to the second knarls, and they were sufficiently washed with distilled water, packed in vacuo, and stored at –80° C. until the next use. After being thawed, the mistletoe leaves and stems were finely cut, mixed by use of a blender, and stirred at 4° C. for 8–12 hours in five volumes of distilled water. Then, the solution was centrifuged at 10,000 rpm at 4° C. for 30 min and the supernatant was let to pass through membranes which were different in pore size (7.2, 0.45 and 0.22 ?mm), in order. Freeze-drying the filtrate afforded a brown powder, KM-110. The yield of KM-110 from Korean mistletoe was 10%.

To make a stock solution, this freeze-dried powder was dissolved at a concentration of 10 mg/ml in a phosphate buffer (pH 7.4) (hereinafter referred to as "PBS"), and aliquoted before storage at –20° C. Isolation of protein from the extract KM-110 was achieved in a precipitation method using ammonium sulphate. Korean mistletoes were stirred in a solution of 0.15 M NaCl of PBS in the same manner as in the preparation of KM-16 and added with ammonium sulphate powder to the extent of 70% of the saturation. Weakly stirring the 70% saturated ammonium sulphate solution at 4° C. allowed the precipitation of proteinaceous ingredients. After being dissolved in PBS, the precipitates were dialyzed against a buffer while the buffer was changed to a fresh one every other day. The supernatant obtained from the centrifugation of the dialyzate at 15,000 g for 30 min was passed through a 0.45 μm membrane filter to give a protein fraction, which was subjected to quantitative analysis with the aid of a protein assay kit (Boehringer Mannheim) and called KM-AS. It was stored at –20° C. until the next use. The yield of KM-AS from mistletoe was 0.3 to 1.5%.

EXAMPLE II

Isolation of Lectin Components and Determination of their Molecular Weights Isolation of lectin components from KM-AS was conducted through column chromatography using the sepharose-4B which was previously hydrolyzed with 0.2 M HCl. KM-AS obtained in Example I was let to pass through the column which was then washed with five column volumes of PBS until the absorbance (O.D.) at 280 nm was zero. A solution of 0.1 M lactose in PBS was used as an eluent to separate the materials bound to the column and the eluate was dialyzed against PBS to remove the lactose. The dialyzate was called KML-C.

Figure 1B:
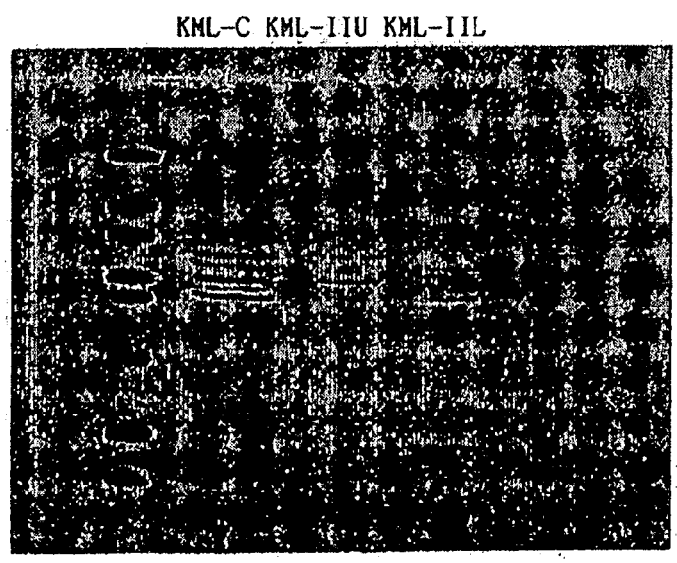
Figure 2:
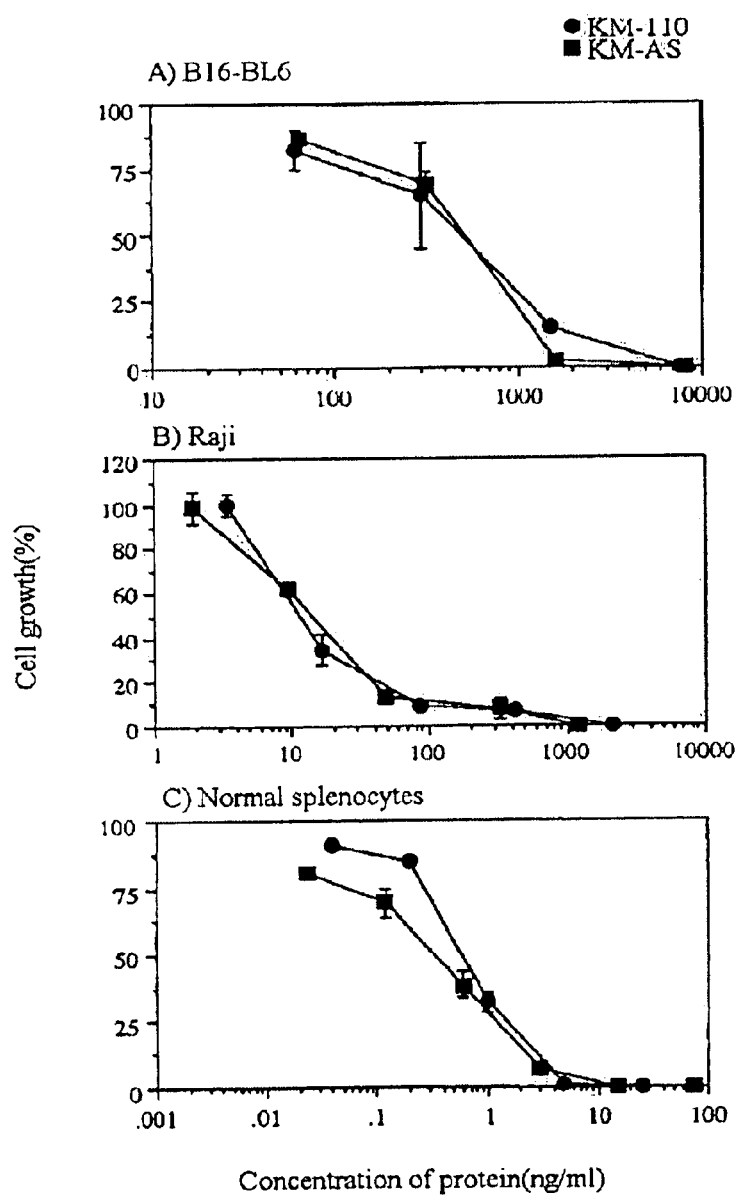

To determine the molecular weight and purity of KML-C, the dialyzate was electrophoresed on a 13% polyacrylamide containing 0.1% SDS, together with a protein marker (FIG. 1B).

EXAMPLE III

Reactivity to the Mitogens for Immune-Competent Cells 6-week-old Balb/c female mice, which were grouped in threes, were injected with 100 μg of KM-10 through an intravenous route and splenocytes were taken from each group after 1, 3 and 5 days of the injection.

The splenocytes were put in each well of flat-bottomed 96-well culture plates (Nunc, Denmark) at a density of $5 \times 10^5$ cells/100 μl, after which the cells in each well were treated with 100 ml of Con. A and LPS, known as mitogens of T cells and B cells respectively, at a density of 0.5 and 5 μg/ml, respectively. Cell culturing was conducted at 37° C. for 3 days in a 5% $CO_2$ atmosphere. At 6 hours before the completion of the cell culturing, [$^3$H]-TdR of 0.5 μCi was added to the cells in each well, followed by adsorbing the cells to glass filters with the aid of Filter Mate 196 (Packard Instrument, Meriden Conn.), which were subsequently measured for radioactivity in Matrix 96TM Direct Beta Counter (Packard).

Figure 3:
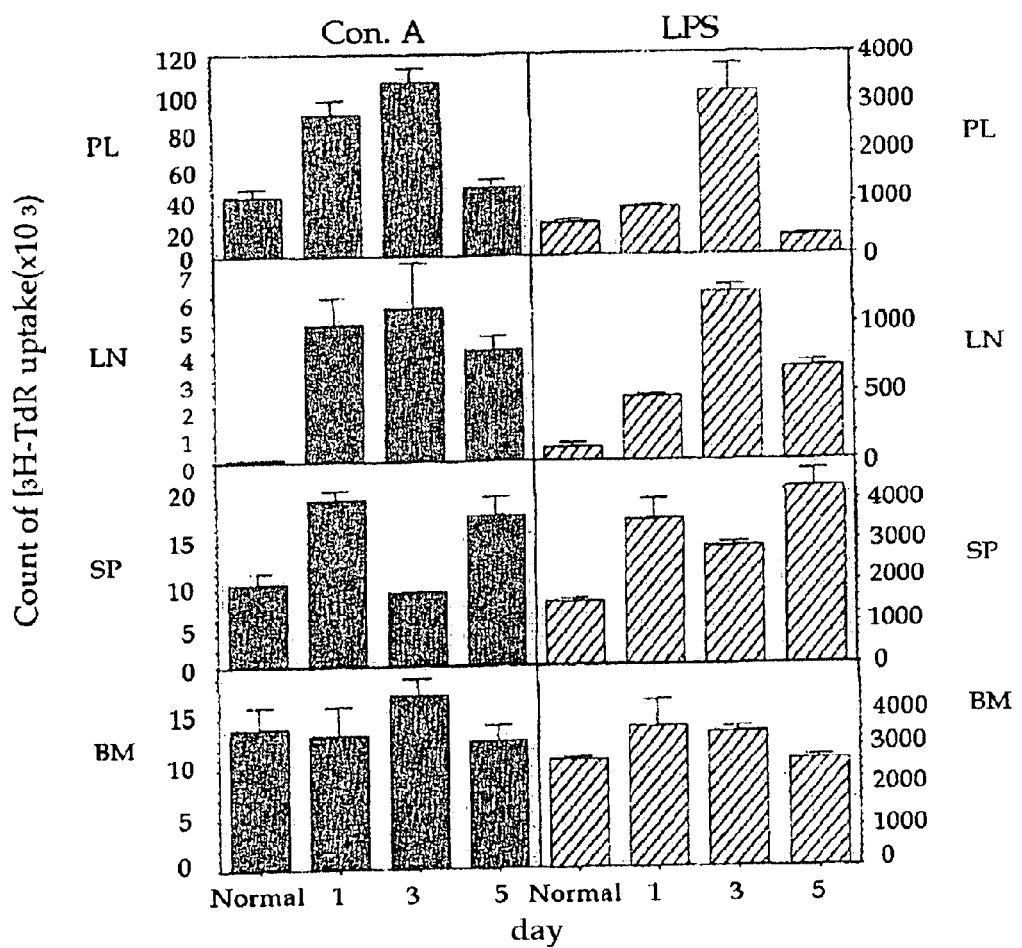
FIG. 3 shows the responses of the immuno-competent cell administered with KM-110 to mitogens Con. A and LPS.

The results are given in FIG. 3. As seen in the figure, the administration of KM-110 led to direct stimulation to the cells (lymphocytes) responsible to the immunity in various organs. Compared with the lymphocytes of normal mice, the lymph nodes (LN), peripheral lymphocytes (PL), spleen lymphocytes (SL) of the KM-110 administered mice were improved in DNA synthesis when being cultured after the treatment with Con. A and LPS, which are mitogens of T and B cells respectively. That is, KM-110 showed an effective response to the mitogens. This response began to increase after the first day of the KM-110 administration and at least doubled on the third day fib after the administration, compared with that of the normal mice, and had a tendency to decline on the fifth day. Since no effective responses were found from bone marrow cells, a kind of immature cells, KM-110 is believed to exert its action only on mature immunocytes.

Figure 4:
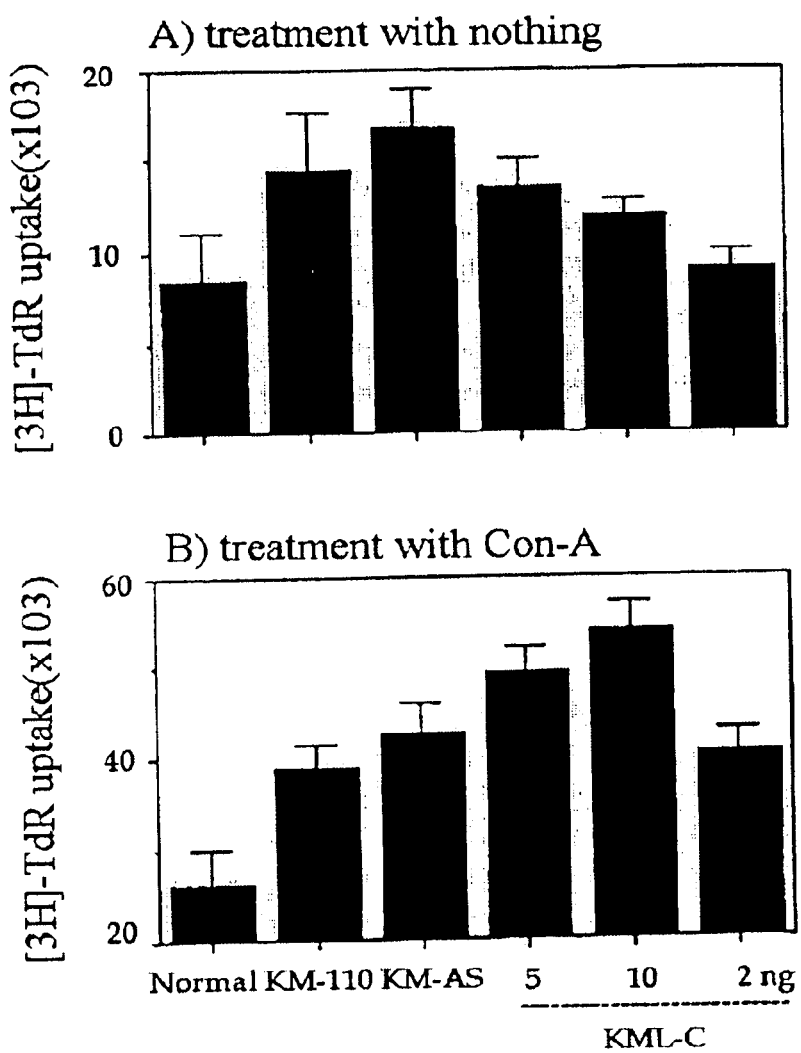
FIGS. 4A–4B show the response of the immuno-competent cell administered with KML-C to Con. A.

100 μg of KM-110 was measured to contain 1.5 μg of proteins. In order to examine the activity of the protein fraction alone among the components of KM-110, an equal amount of KM-AS was administered into mice. As apparent from the results, the splenocytes of the mice administered with each of the samples were more increased in DNA synthesis, even when not stimulated by the mitogens, compared with the non-administered control. This demonstrates that the sample materials stimulate the cell proliferation of splenocytes in vivo. In addition, when used together with the mitogens, the samples of interest were found to amplify the activity of the mitogens. As for KML-C, its administration resulted in increasing the activity of the mitogen in proportion to its concentration, as seen in FIG. 4. Thus, there is a strong suggestion that, of the KM-110, the ingredient that stimulates immunity-related cells is KML-C, a lectin separated from the protein fraction KM-AS.

Taken together, the results obtained in this example demonstrate that KM-110 and its fractions enhance a series of cellular reactions to make mature immunocytes of hosts effectively perform the immune reactions as well as amplify the number of the cells involved in the antigen-specific immune reactions, which are induced when the hosts are exposed to antigens, thereby eliciting effective immunity against the antigens.

EXAMPLE 4

Cytokine Induction of KM-110, KM-AS and KML-C

Balb/c mice were peritoneally injected with 1 ml of 1% thioglycollate and euthanized by the separation of cervical vertebra after 4 days of the injection. 10 ml of an RPMI 1640 medium was injected to the peritoneal cavity of the dead mice whose abdominal walls were, then, lightly hit to mix well the abdominal cells. After being collected from the mice, peritoneal exudative cells were allotted at a density of $1.5 \times 10^6$ cells per well in 24-well culture plates. After a 2 hour culturing, KM-110 and KM-AS were added at various concentrations in the wells and allowed to stimulate the macrophages attached on the plates for 24 hours. Following the stimulation, the induction of cytokines was examined. In this regard, first, a bioassay was conducted to determine whether the supernatants of the cell cultures were of IL-1 activity. Its confirmation was achieved with the aid of an ELISA kit (ENDOGEN). The results are given in FIG. 5. Based on the results, other cytokines, such as TNF-$\alpha$, IL-6 and IFN-$\gamma$ were measured for their induction activity by ELISA. The results are given as shown in FIG. 8.

COMPARATIVE EXAMPLE I

IL-1 Induction

After being stimulated with the samples of interest at 100 $\mu$g–1 $\mu$g/ml for 1 hour, macrophages were cultured in fresh media for 24 hours. As shown in FIG. 5a, the macrophage culture supernatant stimulated with KM-110 was comparable in IL-1 activity to that stimulated with LPS. Based on this result, an examination was made of the IL-1 activity change according to time periods at various concentrations of KM-110. As seen in FIG. 5b, IL-1 activities obtained at the concentration range of 100–10 $\mu$g/ml were maximized to almost the same level at 10 hours after the stimulation while the highest IL-activity was obtained at 50 $\mu$g/ml in an early stage of the stimulation (until 5 hours after the stimulation). Meanwhile, whereas no noticeable IL-1 activity was found at 500 $\mu$g/ml even after 24 hours of stimulation, the stimulation with 1 $\mu$g/ml was recognized to elicit IL-1 activity after 24 hours. From the above results, it is understood that the most effective dose of IL-1 for the induction of IL-1 falls in the range of 10–100 $\mu$g/ml and the IL-1 activity of the supernatant can be maintained at as low as 1 $\mu$g/ml.

To determine which component of KM-110 plays a critical role in the induction of IL-1, KM-AS, the protein component of KM-110, was tested. The protein component KM-AS was used at an amount of 0.25 mg/ml in this experiment.

For use, it was diluted in a 100-fold dilution manner. As shown in FIG. 5c, an activity of IL-1 induction was obtained in KM-AS, indicating that the protein component of KM-110 acts as an IL-1 inducer.

Figure 6:
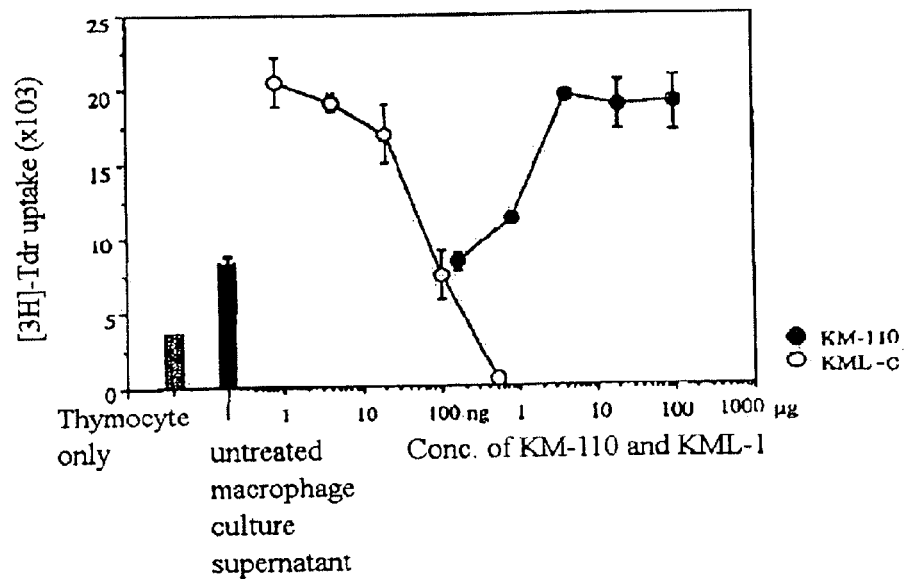

KML-C, isolated from KM-AS, was also investigated for the activity for IL-1 induction and the result is given in FIG. 6. The IL-1 induction in macrophage was noticeable in the concentration range of KML-C from 50 ng/ml to 1 ng/ml, exhibiting a KML-C concentration-dependent behavior.

Figure 7:
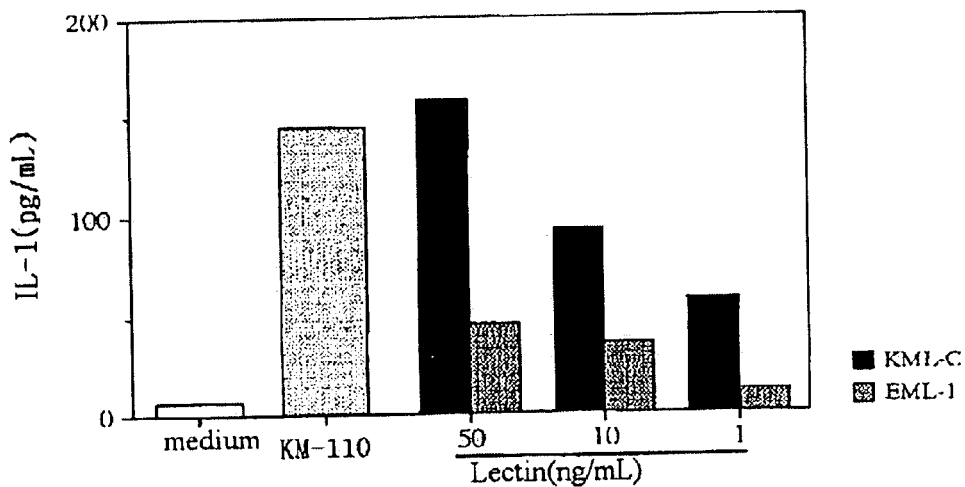
FIG. 7 shows the IL-1 secretion into the culture supernatants of the macrophages stimulated with samples.

By a bioassay, it was verified that the supernatant of the macrophage cell culture stimulated with the mistletoe components has IL-1 activity which activates T thymocytes and KML-C is mainly responsible for the induction of IL-1. The confirmation of the secretion of IL-1 was achieved by ELISA. For ELISA assay of IL-1, samples of interest were sed at the concentrations used to induce IL-1 activity in the bioassay (KM-110: 10 $\mu$g/ml, KML-C: 10 ng/ml). As a control, EML-I, which is a European mistletoe lectin, was used (10 ng/ml). As shown in FIG. 7, all of the test samples succeeded in inducing IL-1 from macrophages while KML-C was identified as one of the most important activators in the IL-1 induction of KM-110. Compared with EML-I, KML-C was believed to be a more active cytokine inducer for its higher IL-1 induction capability. The concentration at which for KML-C to induce macrophages to secrete IL-1 was estimated to range from 1 to 100 ng for mice and from 100 ng to 100 $\mu$g for humans.

COMPARATIVE EXAMPLE 2

Induction of TNF-$\alpha$, IFN-$\gamma$ and IL-6

Using macrophage culture supernatant, KM-AS, KML-C, EML-I and C-free AS, which is a protein fraction free of KML-C, were tested for the induction of TNF-a, IFN-$\gamma$ and IL-6. The results are given in FIG. 8. The fraction concentration capable of stimulating macrophages to induce the cytokines was found to be 5 $\mu$l/ml for KM-AS and C-free AS and 10 $\mu$l/ml for KML-C and EML-I. As seen, KM-AS, KML-C and C-free AS were able to induce IL-6 and TNF-$\alpha$ from macrophages with superiority of KML-C to EML-I in the induction activity. IFN-$\gamma$ was not induced by KML-C. On the other hand, C-free AS was as active to induce IFN-$\gamma$ as KM-AS. From this result, it was deduced that the induction IFN-$\gamma$ from macrophages was carried out not by KML-C, a lectin component, but by another protein component. In addition, the activity of KM-110 to stimulate macrophages to induce IL-1, IL-6, TNF-$\alpha$ and IFN-$\gamma$ was attributed generally to its protein fraction, KM-AS. Further, KML-C was responsible for the induction of IL-1, IL-6 and TNF-$\alpha$, but did not act as an inducer for IFN-$\gamma$. Accordingly, there was a requirement for the identification of the factor that induces IFN-$\gamma$. This work was carried out in the following Example 5.

EXAMPLE 5

Examination of IFN-$\gamma$ Inducer in KM-AS

Figure 9:
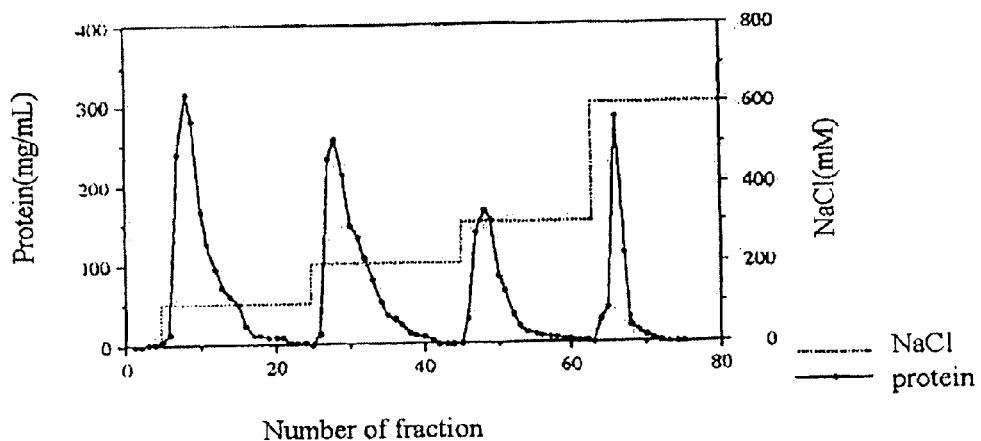
FIG. 9 shows the fractions eluted with various concentrations NaCl to isolate an IFN-γ inducer from KML-C in a chromatogram.

KML-C, a lectin fraction, was able to induce most of the cytokines induced by KM-110 or KM-AS, but could not function as an INF-$\gamma$ inducer, as mentioned in Example 4. As a material used to search for the IFN-$\gamma$ inducer, C-free AS, which is a KM-AS fraction free of KML-C, was selected because it showed a useful activity of inducing IFN-$\gamma$. For the isolation of the IFN-$\gamma$ inducer, a heparin column (Pharmacia) was employed. After being dissolved in a phosphate buffer (0.01 M, pH 7.4), C-free AS was loaded on the heparin column which was, then, washed sufficiently with the same buffer until materials unbound to the column were throughly removed. After washing, the materials bound to the column were eluted by using an NaCl gradient (10 mM–1 M) in the same buffer. FIG. 9 is a chromatogram showing the fraction patterns which were eluted depending on NaCl concentration. Because the elutates, even though not separated as being pure, showed different electrophoresis patterns, they were different from one another in terms of at least the affinity for heparin.

Figure 10:
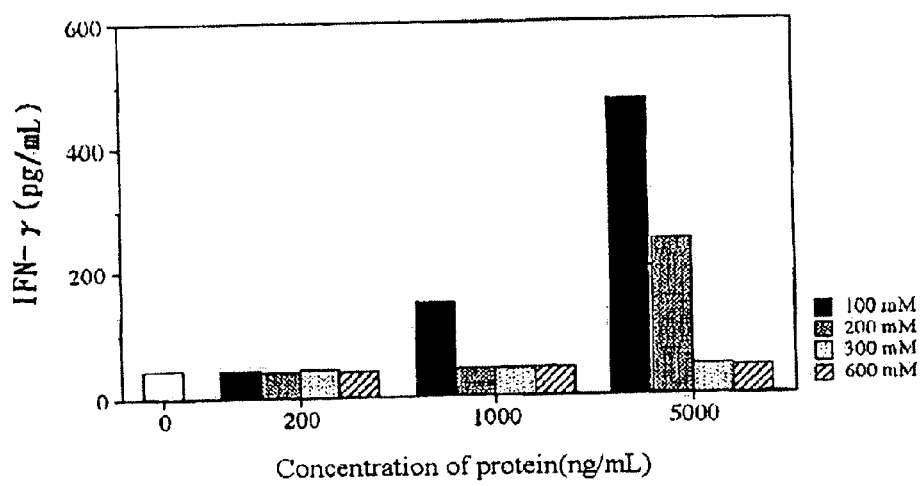
FIG. 10 shows the IFN-γ induction activity of the fractions eluted with various concentrations of NaCl.
Figure 11:
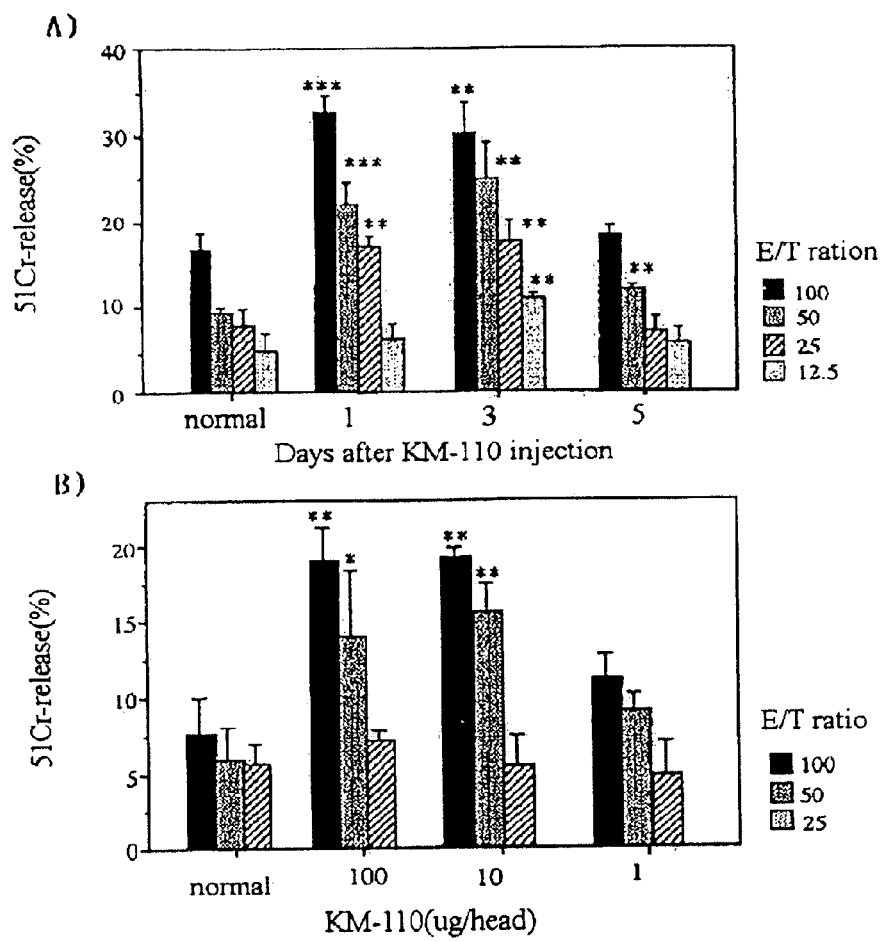
FIG. 11 show NK-cell activity changes according to the administration period of time and concentration of KM-110.
Figure 13:
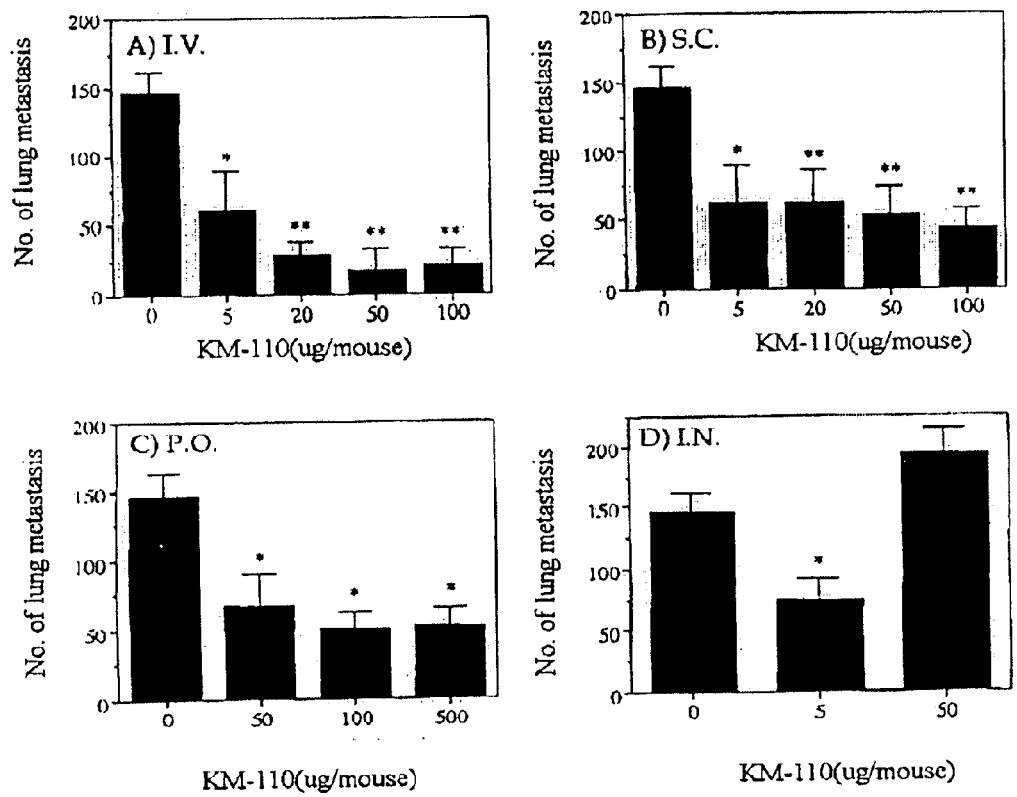
FIGS. 13A–13D show the activity of KM-110 against tumor metastasis in Balb/c mice and C57BL/6 which are injected with KM-110 intravenously, subcutaneously, orally, and nasotracheally, two days before the transplantation of tumors.

Next, an examination was made to determine whether the eluted fractions were active to induce IFN-γ. Each of the fractions separated by the heparin column was used at concentrations of 200–5,000 ng/ml to stimulate macrophages and the resulting culture supernatants were investigated in the same manner as in Comparative Example 2. The results are given in FIG. 10. As seen, the activity to induce IFN-γ was detected largely from the fraction which was eluted by a phosphate buffer containing 100 mM NaCl. Thus, the ingredient of KM-110 which had the activity of inducing IFN-γ was a Korean mistletoe haparin binding protein (KMHBP) fraction which was eluted with 100 mM NaCl. In order to induce the most effective immune activity, therefore, there are required not only the lectin component KML-C, but also the KMHBP ingredient (hereinafter referred to as "KMHBP-100") which is separated from C-free AS by heparin column chromatography eluting with a 100 mM NaCl phosphate buffer. In mice, a mixture of 5–100 ng of KML-C mixture of 500 ng–100 µg of KML-C and 10 µg–10 mg of KMHBP-100 is effective.

EXAMPLE 6

In Vivo Acute Toxicity of KM-110 and Other Fractions

KM-110, KML-C and KMHBP, which are extracts from mistletoe parasitic on *Quercus*, were examined for the acute toxic effects on mice. Into 6-week-old Balb/c mice (female), KML-C was intravenously injected at amounts of 5, 2.5, 1.25, and 0.62 mg and KMHBP-100 at amounts of 110, 50 and 25 µg. Afterwards, the mice were measured for body weight change and viability for 7 days. Each test group consisted of 10 mice.

The results are given in Tables 1 and 2, below. As seen in Table 1, when administered with KM-110, the 1.5 mg/mice group were all killed within 24 hours of the administration. On the other hand, no dead were found in the 1.0 mg/mice group. The mice which had been alive after being administered with 1.0 mg of KM-110, were decreased in body weight on the third day of the administration, but revived to the normal state on the fifth day. After 7 days of administration, no outward abnormalities could be found from the mice group. The lethal dose $LD_{50}$, which stands for acute toxicity, was estimated to be 1.0–1.5 mg/mouse (about 1.25 mg/mouse) for KM-110 and about 12.5 µg/mouse for KM-AS.

As for KML-C, a dose of 5 or 2.5 µg per mouse made the mice undergo serious piloerection and adynamia and they were finally put to death within 2 days. In the 1.25 µg/mice group, none were dead on the day of administration, but 2 mice were dead on the second day and another mouse on the third day. The mice administered with an amount of 1.25 µg were decreased in body weight by about 5% after 3–5 days of the administration as seen in Table 2, showing the piloerection and adynamia which were, to the inventor's knowledge, attributed to fever. From the sixth day of the administration, however, they were revived into the normal state, gaining in weight. No abnormalities were found in the 0.625 µg/mice group, compared with normal mice. Thus, KML-C was estimated to have an $LD_{50}$ of about 1.25 µg.

In the 100 µg/mice group administered with KMHBP-100, all were dead after one day of administration. Weight loss or other abnormalities could not be found in the group into which KMHBP-100 was injected at a dose of 50 µg. Thus, the $LD_{50}$ F KMHBP-100 was estimated to be between 100 and 50 µg/kg of body weight.

TABLE 1

Viability of Mice Administered with Mistletoe Extracts

| Samples | Dose/mouse | Days/Viability (%) | | | | | | | Results (%) |
| --- | --- | --- | --- | --- | --- | --- | --- | --- | --- |
| | | 1 | 2 | 3 | 4 | 5 | 6 | 7 | |
| KM-110 | 1.5 mg | 0 | — | — | — | — | — | — | 0 |
| | 1.0 mg | 100 | 100 | 100 | 100 | 100 | 100 | 100 | 100 |
| MKL-C | 5 µg | 40 | 0 | — | — | — | — | — | 0 |
| | 2.5 µg | 80 | 0 | — | — | — | — | — | 0 |
| | 1.25 µg | 100 | 60 | 60 | 60 | 40 | 40 | 40 | 40 |
| | 0.625 µg | 100 | 100 | 100 | 100 | 100 | 100 | 100 | 100 |
| KMHBP | 100 µg | 0 | 0 | 0 | 0 | 0 | 0 | 0 | 0 |
| | 50 µg | 80 | 70 | 70 | 70 | 70 | 70 | 70 | 70 |
| | 25 µg | 100 | 100 | 100 | 100 | 100 | 100 | 100 | 100 |

TABLE 2

Weight Change According to i.v. Injection of Mistletoe Extracts

| Samples | Dose/Mouse | Days/Avg. Wt (g) ± SD | | | |
| --- | --- | --- | --- | --- | --- |
| | | 1 | 3 | 5 | 7 |
| | — | 20.2 ± 0.5 | 20.3 ± 0.6 | 20.3 ± 0.7 | 20.2 ± 0.6 |
| KM-110 | 1.5 mg | — | — | — | — |
| | 1.0 mg | 20.2 ± 0.8 | 19.8 ± 0.6 | 20.0 ± 0.8 | 20.1 ± 0.9 |
| MKL-C | 5 µg | 19.5 ± 0.7 | — | — | — |
| | 2.5 µg | 19.4 ± 0.5 | — | — | — |
| | 1.25 µg | 19.6 ± 0.4 | 19.0 ± 0.6 | 19.1 ± 0.7 | 19.4 ± 0.5 |
| | 0.625 µg | 20.2 ± 0.5 | 19.7 ± 0.6 | 20.0 ± 0.6 | 20.1 ± 0.6 |
| KMHBP | 100 µg | — | — | — | — |
| | 50 µg | 20.2 ± 0.7 | 20.2 ± 0.7 | 20.3 ± 0.9 | 20.4 ± 0.8 |
| | 25 µg | 20.2 ± 0.7 | 20.5 ± 0.8 | 20.6 ± 0.8 | 20.6 ± 0.9 |

EXAMPLE 7

Repressive Activity of KML-C Against Tumor Metastasis

Based on the result of the in vitro experiments concerning cytotoxicity and cytokine induction, in which KML-C was found to be one of the most important active ingredients of KM-110, an examination was made to determine which ingredient of KM-110 has inhibitory activity against tumor metastasis.

Figure 14:
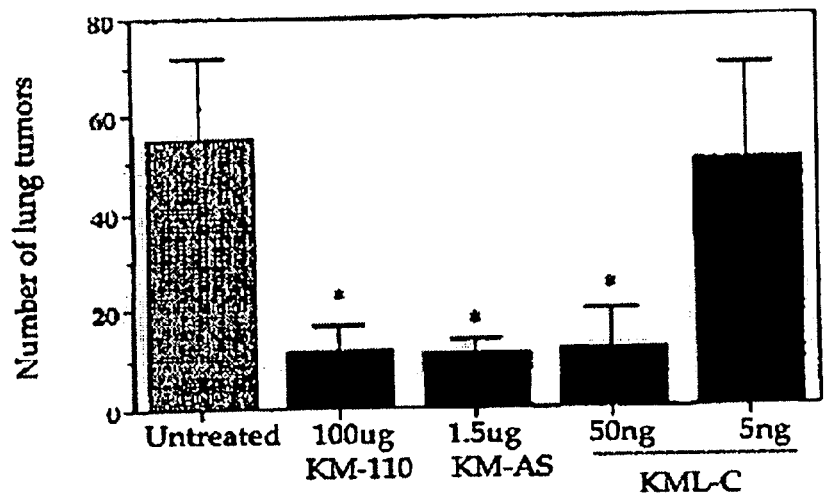
FIG. 14 shows the activity of KML-C against the tumor metastasis of the lung cancer caused by colon 26-M3.1 cells.

As shown in FIG. 14 which contains the experimental result regarding the preventive effects of the mistletoe extracts on colon 26-M3.1 carcinoma metastasis, the administration of 100 µg of KM-110 resulted in the repression of tumor metastasis by more than 80%. A similar repressive effect on tumor metastasis was detected between KM-AS and KM-110, indicating that the antitumoral activity of KM-110 exists in its protein ingredients. Like 100 μg of KM-110, 50 ng of KML-C also showed the activity of repressing the tumor metastasis by more than 80%. Since no repression effects on tumor metastasis were found from the administration of KML-C at a dose of 5 ng, the effective amount of KML-C for in vivo antitumoral activity was measured to be over 5 ng.

The repressive effects on tumor metastasis of KM-110 and KML-C were also true of the L5178Y-ML25 lymphoma. With regard to tumor metastasis, the active ingredient of KM-110 was, thus, KML-C. As shown in Tables 3 and 4, the effective amount of KML-C to repress tumor metastasis in vivo was measured to range from 10 to 50 ng. The antitumoral activity of KML-C is believed to result from the direct cytotoxicity effect on tumor cells as well as the immunological stimulation to induce the activity of macrophages and NK-cells, which both are involved in the defense mechanism against tumors.

TABLE 3

Curing Effects of KML-C on the Metastasis of Tumors Generated in Liver, Spleen and Lung (Experiment I: L5178Y-ML25 Lymphoma cells)

| Korean Mistletoe Treatment | | | Avg. Wt. (g) ± SD (%) | |
|---|---|---|---|---|
| | Inoculting Time | Dose | Liver | Spleen |
| Normal Mice | | | 1.07 ± 0.1 | 0.09 ± 0.02 |
| Non-treated | (Tumor Control) | | 3.54 ± 0.48 | 0.21 ± 0.05 |
| KM-110 | 1 day after tumor inoculation | 100 μg | 0.59 ± 0.22 (56.5) | 0.14 ± 0.02 (33.3)* |
| KML-C | | 50 μg | 1.83 ± 0.84 (48.3)** | 0.16 ± 0.04 |

*p < 0.05;
**P < 0.01, by student's two-tailed test, compared

TABLE 4

Curing Effects of KML-C on the Metastasis of Tumors Generated in Liver, Spleen and Lung (Experiment II: Colon 26-M3.1 Carcinoma cells)

| Korean Mistletoe Treatment | | | No. of Lung Cancer Metastasis | |
|---|---|---|---|---|
| | Inoculating Time | Dose | Avg. Wt. ± SD | Range |
| Non-treated | Tumor Control | | 100 ± 13 | 85~17 |
| KM-110 | 1, 2 and 3 days after tumor inoculation | 100 μg | 62 ± 30 (38.0)* | 27~93 |
| KM-AS | | 1.5 μg | 59 ± 18 (41.0)** | 44~83 |
| KML-C | | 500 ng | 74 ± 23 (26.0) | 41~97 |
| KML-C | | 25 ng | 54 ± 27 (46.0) | 26~77 |
| KML-C | | 10 ng | 61 ± 14 (39.0) | 43~76 |
| KML-C | | 1 ng | 98 ± 11 | 82~108 |

*p < 0.05;
**P < 0.01, by student's two-tailed test, compared

EXAMPLE 8

Tumor Cell Killing Activity by Activation of Macrophage

Macrophages, which take the lead in the immune surveillance system of the body, are well known as a defense tool against tumors, virus-infected cells, microbes, etc. With regard to antitumoral activity, macrophages kill tumor cells in two patterns: first, they secrete various cytokines which involve the immune mechanism of tumor cells; and they are brought into direct contact with tumor cells to exert their cytotoxicity effect on the tumor cells. In addition, macrophages induce a post-immune defense mechanism against the tumor cells.

To investigate whether the antitumoral activity of KM-110 and KML-C is related to the direct killing activity of macrophages, the materials of interest were injected into mice. 100 μg of KM-110 or 50 ng of KML-C was used for the peritoneal injection into mice (B16-BL/c). After 2 and 4 days of receiving the injection, macrophages (effector cells) were disinfectively collected with the aid of RPMI-1640 media and measured for tumor cell killing activity. As a target tumor cell, B16-BL6 melanoma was labeled with radioactive isotope $^{51}Cr$, and then added in 96-well culture plates at a cell density of $1 \times 10^4$ per well. To the wells in which the melanoma cells resided, the macrophages obtained from the mice administered with KM-110 or KML-C were added at cell densities of $1 \times 10^5$ and $5 \times 10^4$ per well, after which they both were co-cultured for 12 hours. As a control, macrophages obtained from the non-treated normal mice were utilized. After culturing, the activation of macrophages by the samples of interest was measured in tumor cell killing activity, which was calculated as follows:

$$\text{Killing Activity}(\%) = \frac{\text{experimental release} - \text{spontaneous release}}{\text{maximal release} - \text{spontaneous release}}$$

Figure 15:
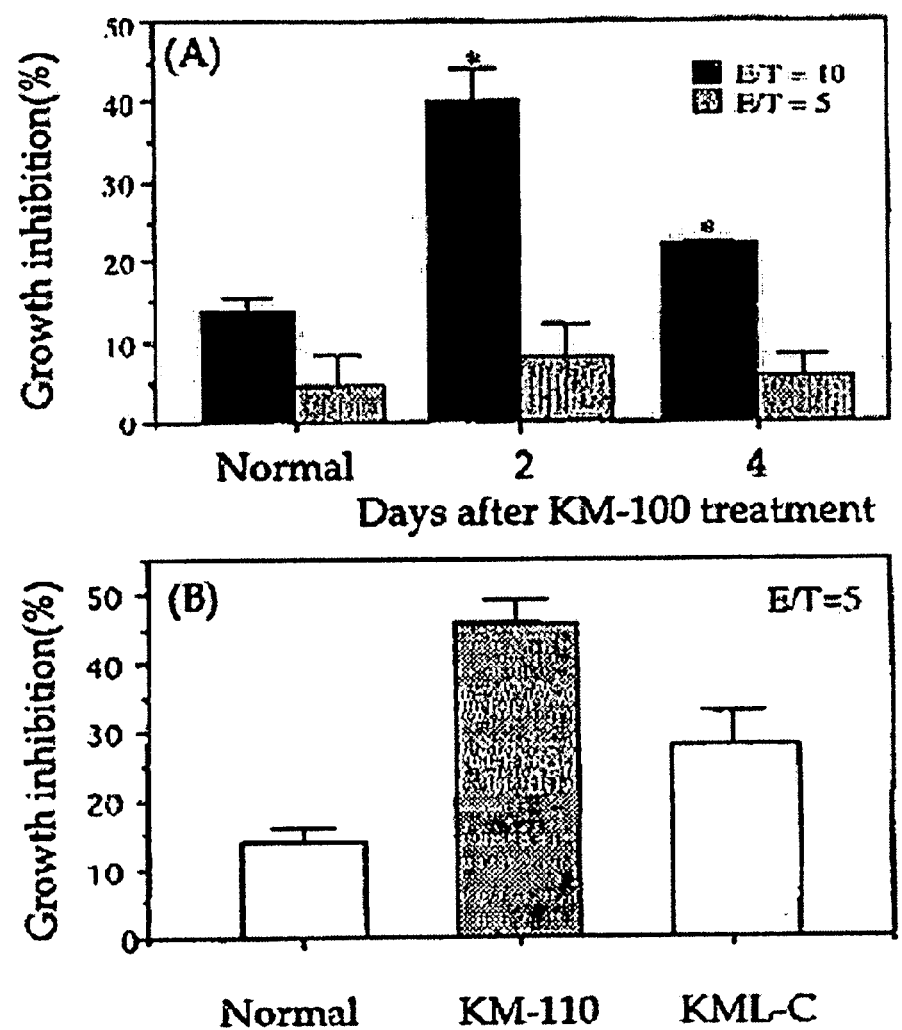
FIGS. 15A–15B show the killing activity of mouse macrophage induced by KM-110 over B16-BL6 melanoma.
Figure 16:
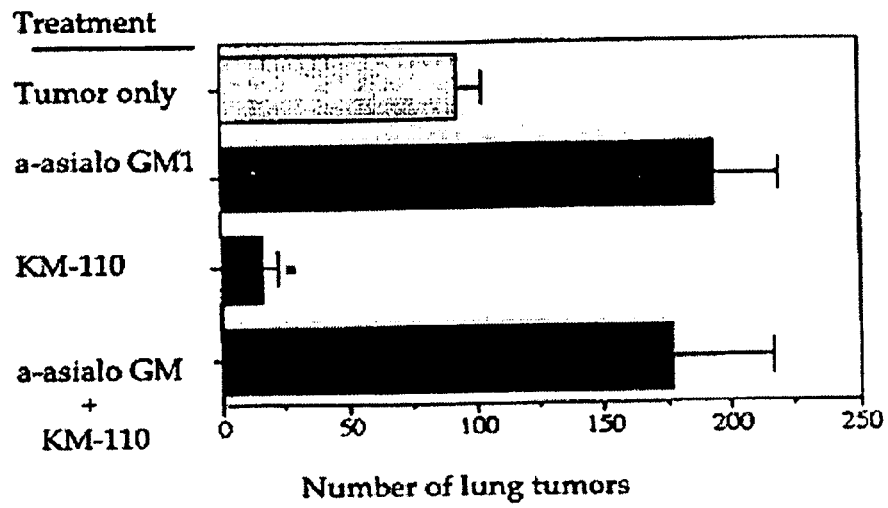
FIG. 16 shows the effect of KM-110 on the metastasis of colon 26-M3.1 lung cancer in the mice deprived of NK-4D cells by the injection of anti-asialo-GM1 antibody.
Figure 17:
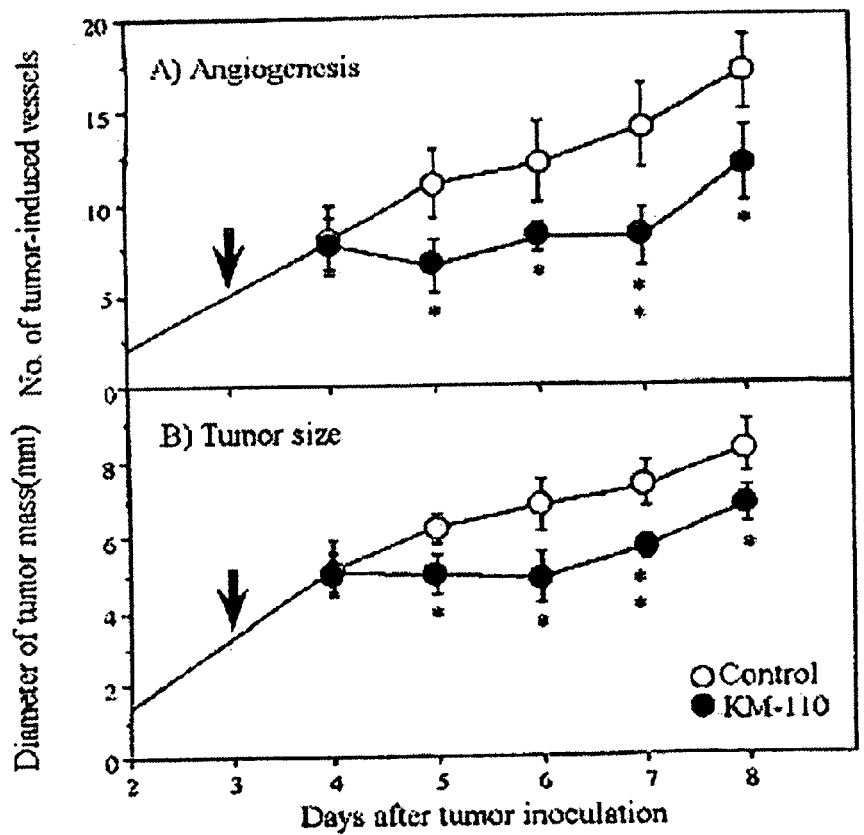
FIGS. 17A–17B show the inhibitory activity of KM-110 against tumor-dependent vascularization and tumor growth in vivo.
Figure 19:
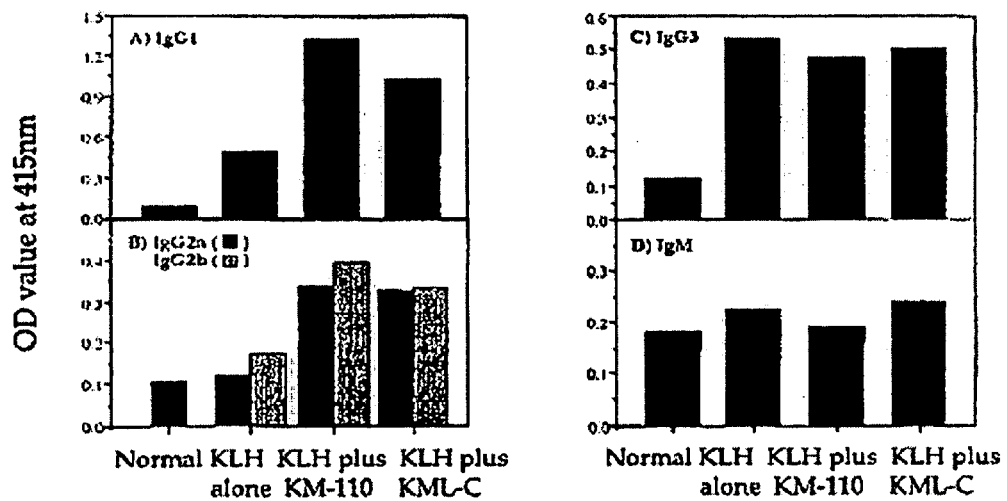
FIGS. 19A–19D show the sub-isotype analysis results of the KHL-specific antibodies induced by the immunization with KHL alone and in combination with KM-110.
Figure 20:
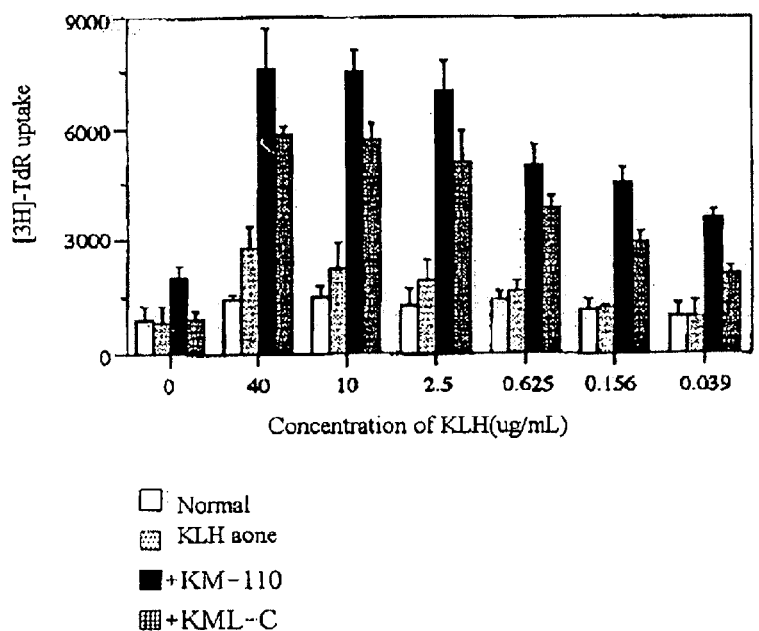
FIG. 20 shows antigen-specific differentiation activity of the splenocytes immunized with KLH.
Figure 21:
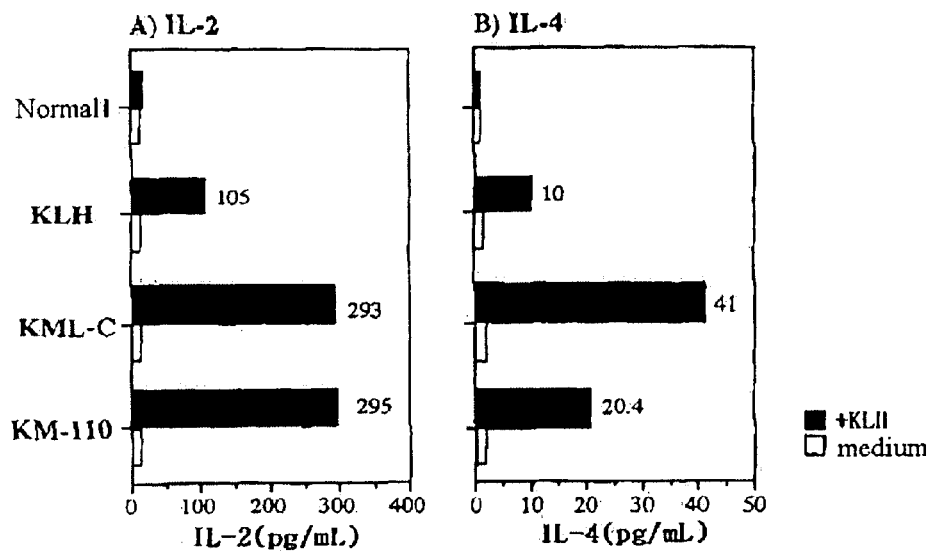
FIGS. 21A–21B show the induction results of IL-2 and IL-4 from mouse splenocytes immunized with KLH.
Figure 22:
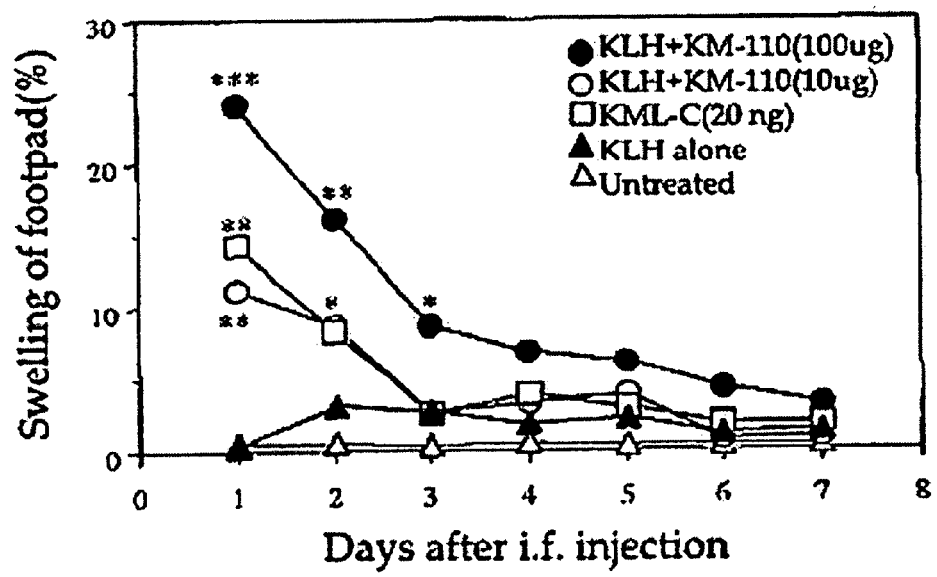
FIG. 22 shows the increase in footpad tumor number in the mice immunized with combinations of KM-110, KML-C and KLH compared with in the mice immunized with KM-110, KML-C and KLH alone.
Figure 23:
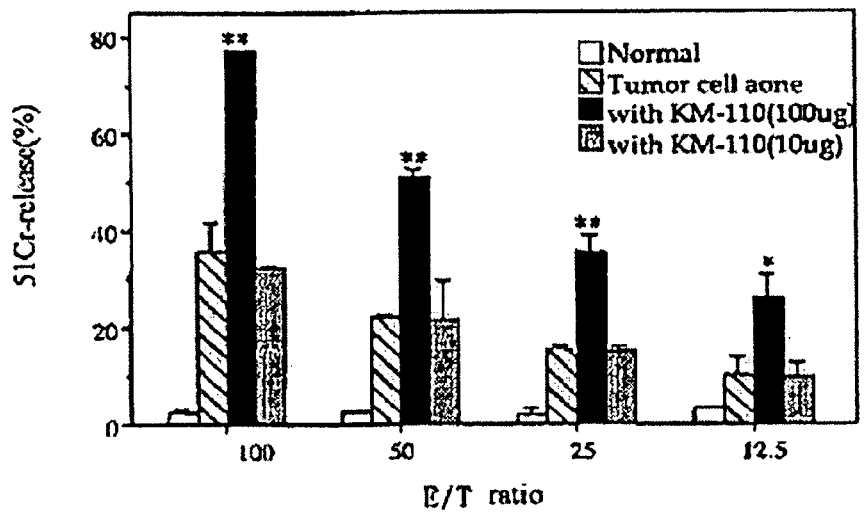
FIG. 23 shows the increase induced by KM-110 in the CTL activity over xenogenic tumor cells.
Figure 24:
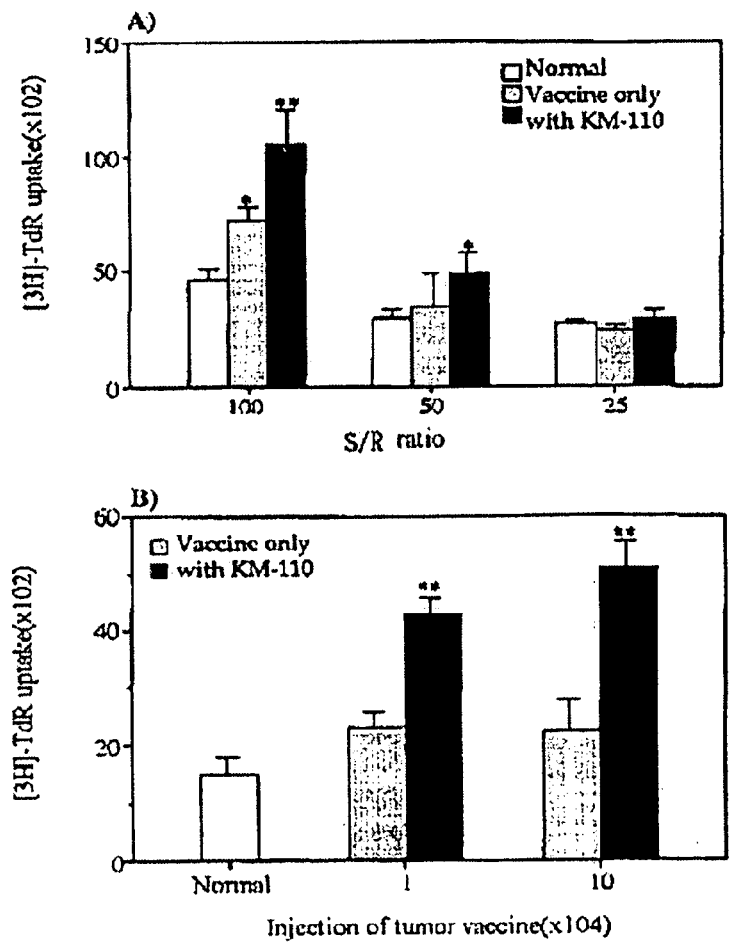
FIGS. 24A–24B show the specific differentiation of splenocytes upon tumor vaccine and KM-110 alone or in combination.

As shown in FIG. 15A, the macrophages of the mice injected with 100 μg of KM-110 were about three times as high in the inhibitory activity against B16-BL6 melanoma cell proliferation as those of the mice which were not treated with KM-110. This inhibitory activity reached a maximal point on the second day of the KM-110 injection and began to decrease from the forth day. Thus, KM-110 is deemed to function to activate macrophages in vivo, leading to killing tumor cells. Based on this result, the tumor cell killing activity of macrophage according to KML-C injection was measured on the second day of the injection. As seen in FIG. 15B, the macrophages showed an improved activity of effectively killing $^{51}Cr$-labeled B16-BL6 melanoma cells after 2 days of KML-C injection. These data obtained demonstrate that, of the KM-110 components, KML-C plays a major role in stimulating macrophages to exert the killing mechanism on tumor cells. The tumor cell killing activity of macrophages are known to be carried out by secreting TNF-α or by bringing themselves into direct contact with tumor cells. In addition, since activated macrophages secrete tumor cell-killing reactive oxygen (ROIs) and nitrogen monooxide (NO), the tumor cell killing activity of macrophages induced by KM-110 or KML-C would be related to the secretion of such killing materials, in the inventors' estimation.

EXAMPLE 9

Production and Characterization of Anti-KML-C Monoclonal Antibody

For the production of anti-KML-C monoclonal antibody, first, a PBS buffer containing KML-C at a concentration of 300 ng/100 μl was emulsified with an equal volume of the complete Freund's adjuvant and peritoneally injected into Balb/c mice. After 14 days, the primarily immunized mice were further immunized with the same amount of the antigen emulsified with incomplete Freund's adjuvant. After 10 days of the final immunization, a small amount of blood was taken from the immunized mice and measured for the antibody titer by an indirect ELISA in which the antigen was immobilized. Subsequently, using the antigen (100 ng) only, a booster injection was administered into the abdominal cavity of the mice. After one week, the splenocytes from the KML-C-immunized Balb/c mice were subjected to the cell fusion to P3U1 myeloma with the aid of PEG, followed by selecting the hybridoma cells in HAT media. An ELISA was carried out to screen the hydridoma cells which produced anti-KML-C antibodies. The hydridoma cells were cloned in 96-well plates in such a manner that one hybridoma existed in each well, and cultured to form colonies. The culture supernatant of the hybridomas grown to colonies was examined by ELISA to screen the hybridomas which produces antibodies against KML-C. This cloning and screening was repeated twice further to select the hybridoma cells which produce anti-KML-C monoclonal antibodies.

Figure 25:
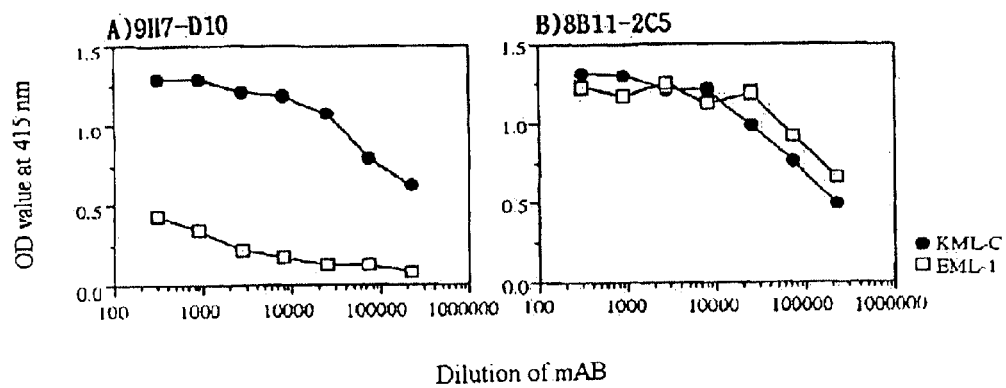
FIGS. 25A–25B show the cross reaction of monoclonal antibodies 9H7-D10 and 8B11-2C5 with KML-C and EML-I.

A large quantity of the monoclonal antibodies were required for their characterization. For this, the hybridoma cells were injected into the abdominal cavity of pristane-treated mice to obtain an ascitic fluid. The ascitic fluid was loaded on a protein-G affinity column to purify the monoclonal antibodies. Of them, the antibodies which were of specific activity for KML-C alone and the antibodies which showed cross-reactivity for KML-C and EML-I were selected by ELISA. To this end, KML-C or EML-I was first coated at 2 µg/ml on each well of an ELISA plate and blocked by BSA. Then, the ascitic fluid of hybridoma which showed a positive reaction was added to the wells and allowed to stand for the antigen-antibody reaction. An HRP-conjugated secondary antibody was added to the wells, followed by coloring by use of TMB (Sigma) as a substrate. Absorbance at 450 nm was measured and the result is given in FIG. 25. Through an antibody-specific ELISA experiment, 9R7-D10 was identified as an antibody highly specific for KML-C while 8B11-2C5 showed high cross-reactivity for KML-C and EML-I both, as seen in FIG. 25. As a result of a cross-reaction ELISA experiment, when the antibody titer of each antibody was expressed as the dilution of the ascitic fluid which showed an optical density (O.D.) significantly higher than that of NSB (non-specific binding) antibody, that is, an O.D of 0.5 or more, 9H7-D10 and 8B11-2C5 antibodies showed high antibody titers of more than 50,000 and 100,000, respectively. Additionally, 8E12-3E9 was also an antibody that showed a positive reaction against KML-C. As for antibody subtype, 9H7-D10 and 8B11-2C5 both proved to be of an IgG1 type while 8E12-3E9 was of an IgM type. These three antibodies were used for the isolation and fractionation of lectin, later.

EXAMPLE 10

Preparation of Immuno-Affinity Column and Isolation of KML-IIU and KML-IIL

Figure 26:
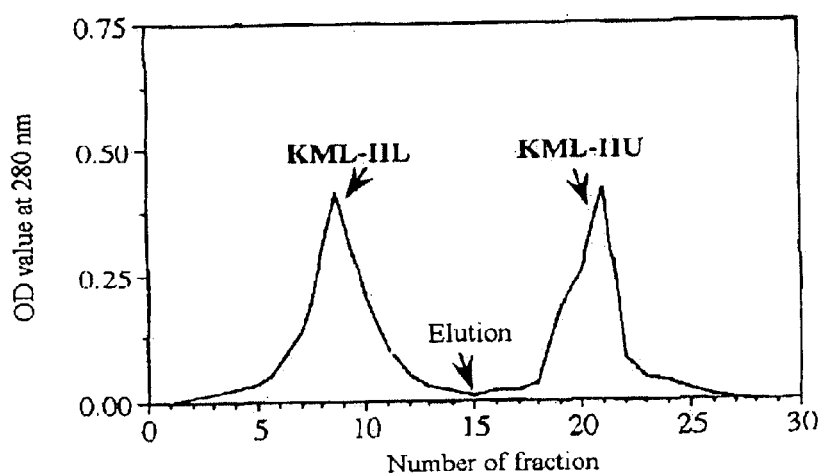
FIG. 26 shows the separation of lectins KML-IIU and KML-IIL from KML-C by immuno-affinity chromatograpy.

9H7-D10, which was found to react specifically to KML-C without cross-reaction with EML-I as measured by an ELISA, was used to rapidly separate two lectin ingredients from KML-C by affinity chromatography. For this, the monoclonal antibody was immobilized in a HiTrip NHS activated affinity column (Pharmacia Boitech) according to the manufacturer's indication, so as to obtain an immuno-affinity column. The column was equilibrated with PBS (pH 7.4) and KML-C was allowed to pass through the column. Subsequently, the effluent fractions were obtained by flowing PBS and a glycine-HCl buffer (pH 2.7) through the column at an elution rate of 1 ml/2 min. Each effluate was measured for purity and molecular weight by 10% SDS-polyacrylamide electrophoresis using KML-C and EML-I as controls. As shown in the results of FIG. 26, two fractions were separated from KML-C through the 9H7-D10 antibody-immobilized immuno-affinity column. The fraction which was larger in molecular weight according to the electrophoretic pattern, was called "KML-IIU" and the other "KML-IIL". Each of these fractions was found to be a heterodimer consisting of two domains which were different in molecular weight and linked to each other via a disulfide bond as analyzed by the electrophoresis on a mecaptoethanol-containing gel. In detail, KML-IIU was 61.8 kD in molecular weight, consisting of a 33.2 kD peptide chain and a 28.6 kD peptide chain while KML-IIL has a molecular weight of 56.4 kD composed of a 31 kD peptide chain and a 28.6 kD peptide chain. These constituent proteins are quite different in molecular weight from those of the European mistletoe lectin components (ML-I, -II, and -III) reported.

EXAMPLE 11

Sugar Specificity of KML-IIU and KML-IIL

To investigate whether the two protein fractions isolated from KML-C have lectin activity and for which sugar the two protein fractions, if being of lectin activity, exhibit specificity, experiments for hemagglutination and hemagglutination inhibition of sugar were carried out on U-type 96-well plates. A solution of 2% B-blood cell in PBS was added to each well of the plates, followed by the addition of various concentrations of the protein fractions to each well. After culturing for 1 hour at room temperature, the minimal concentrations at which the protein fractions can exhibit the hemagglutination were obtained (Table 5). As seen in Table 5, Korean mistletoe-derived KML-C and its KML-IIU and KML-IIL each hemagglutinated at a concentration of as low as 8 µg/ml, so they were identified as lentin materials.

In order to examine the specificity of the lectin materials for sugars, various sugars were stepwise diluted from 100 mM and added to the protein fractions which were present at a concentration necessary to exhibit hemagglutination, thereby causing the inhibition of hematogglutination (Table 6). KML-C, KML-IIU and KML-IIL were all restrained from hemagglutinating by lactose, galactose, and N-acetylgalactoseamine. On the other hand, the hemagglutination of EML-I was inhibited by lactose and galactose as reported. Because none of Korean and European lectins were inhibited from hemagglutinating by glucose, a component composing lactose, the Korean mistletoe lectins separated according to the present invention were found to be of specificity for galactose and N-acetylgalatoseamine.

TABLE 5

Hemagglutination Activity of KMLIIU and KML-IIL

| Lectin | Minimal Conc. (µg/mL) |
| --- | --- |
| KML-C | 8 |
| KML-IIU | 8 |
| KML-IIL | 8 |
| EML-1 | 2 |

TABLE 6

Minimal Concentrations of Various Sugars Necessary to Inhibit the Hemagglutination of KML-IIU and KML-IIL

| Saccharides | Minimal Conc. (mM) |
| --- | --- |
| Galactose | 6 |
| Lactose | 3 |
| N-Acetylgalactosamine | 3 |
| Mannose | >100 |

TABLE 6-continued

Minimal Concentrations of Various Sugars Necessary to
Inhibit the Hemagglutination of KML-IIU and KML-IIL

| Saccharides | Minimal Conc. (mM) |
|---|---|
| Glucose | >100 |
| N-Acetylglucosamine | >100 |

EXAMPLE 12

Amino Acid Sequences of KML-IIU, KML-IIL and European Lectins

N-terminal amino acid sequencing was conducted to compare the amino acid sequences of KML-IIU and KML-IIL with that of EML-I. A- and B-chain of KML-IIU, separated from each other on a reduced SDS-PAGE, were transferred into a PVDF (polyvinylidene difluoride) membrane by electroblotting at 85 mA for 70 min. The protein bands blotted were hydrolyzed at 110° C. for 24 hours in 6M HCl and applied to an amino acid analyzer (Effendorf/Niotronic, LC 3000) to analyze the amino acid sequence of each chain. In this manner, the amino acid sequence of KML-IIL was revealed, and compared with that of the European lectin EML-I as shown in Table 7, below. Each chain was called A-chain when it appeared at a lower position on an electrophoresis because of its smaller molecular weight. On the other hand, the chain which appeared at an upper position owing to larger molecular weight was designated B-chain. As a result of the amino acid sequence analysis for the A-chain of KML-IIU, in an amino acid stretch from the N-terminal to the $30^{th}$ amino acid residue, 24 amino acid residues, except for the $5^{th}$, the $15^{th}$, the $16^{th}$, the $27^{th}$, and the $28^{th}$ amino acid residue, were found to be identical to those of the EML-I, so that the KML-IIU A-chain is 15% different from the EML-I A-chain. EML-I, -II, and -III are reported to be identical in the amino acid sequence from the N-terminal to the $30^{th}$ amino acid residue. In addition, EML-II and -III are slightly smaller in molecular weight than EML-I and they are also distinguished even by different sugar-specific isoforms. When these situations are taken into account, the A-chain of KML-IIU is believed to have a different structure from corresponding chains of the whole European lectins EML-I, -II and -III in terms of at least the amino acid sequence from the N-terminal to the $30^{th}$ amino acid residue. Also, as a result of the analysis of B-chains, although the KML-IIU was unable to compare with the European lectins, KML-IIL was revealed to be quite different from the European lectins in amino acid sequence.

EXAMPLE 13

Cytotoxicity Effects of KML-IIU and KML-IIL on Cancer Cells

An examination was made of in vitro cytotoxicity effects of Korean mistletoe lectins on various cell lines with a control of European mistletoe lectin (EML-1) First, a predetermined amount of each cell strain was added to 96-well plates and allowed to react with various concentrations of lectins. After 48 hours, the cell growth was measured by an XTT(?ATT) assay. In Table 8 are given the doses ($ED_{50}$) at which the samples of interest effectively inhibited the growth of each cell strain by 50%. Most of the lectins are comparatively highly resistant to B16-BL6 melanoma, Meth A fibrosacoma cell lines while being relatively highly susceptible to 3LL carcinoma and Raji lymphoma, so that they are specific for some cancer cells. Over most cell lines, the cytotoxicity effects of KML-C were measured to be more potent than those of European lectins. In some cancer cell lines, the Korean mistletoe showed cytotoxicity 10 times as large as those of European lectins. Compared with KML-IIU, KML-IIL exhibited relatively higher cytotoxicity over all of colon 26-M3.1 carcinoma, B16-BL6 melanoma and L1210 leukemia cell lines.

TABLE 8

Killing Effects of Korean and European Mistletoe Lectins

| Cell lines | Sources | Conc. to Inhibit Tumor Cell Growth by 50% ($ED_{50}$) (/mL) | | | |
|---|---|---|---|---|---|
| | | KML-C | KML-II U | KML-II L | EML-1 |
| 26-M3.1 | Carcinoma | 5 ng | 40 ng | 1.1 ng | 8.1 ng |
| B16-BL6 | Melanoma | 15 ng | 140 ng | 21 ng | 320 ng |
| L1210 | Leukemia | 1.5 ng | 20.1 ng | 1.5 ng | 1.5 ng |
| Jurkat | Leukemia | 110 pg | 2.0 ng | 90 pg | 2.0 ng |
| HL60 | Leukemia | — | 50.5 ng | 1.0 ng | 21.0 ng |
| Meth A | Fibro-carcinoma | — | 210 ng | — | 1200 ng |
| 3LL | Carcinoma | — | 80 ng | — | 30 ng |

EXAMPLE 14

Reactivity of Monoclonal Antibody to Each Lectin and Neutralization Effect of Cytotoxicity Of the prepared monoclonal antibodies, 9H7-D10 and 8B11-2C5, which exhibited high reactivity to KML-C and EML-I, were used to examine the cross-reaction between monoclonal antibodies and lectins by a sandwich ELISA. 8E12-3E9 antibody, which is of an IgM type and cross-reacts with each lectin, was coated on each well of ELISA

TABLE 7

Amino Acid Sequences of KML-IIU, KML-IIL and EML-I Chains

Figure 27:
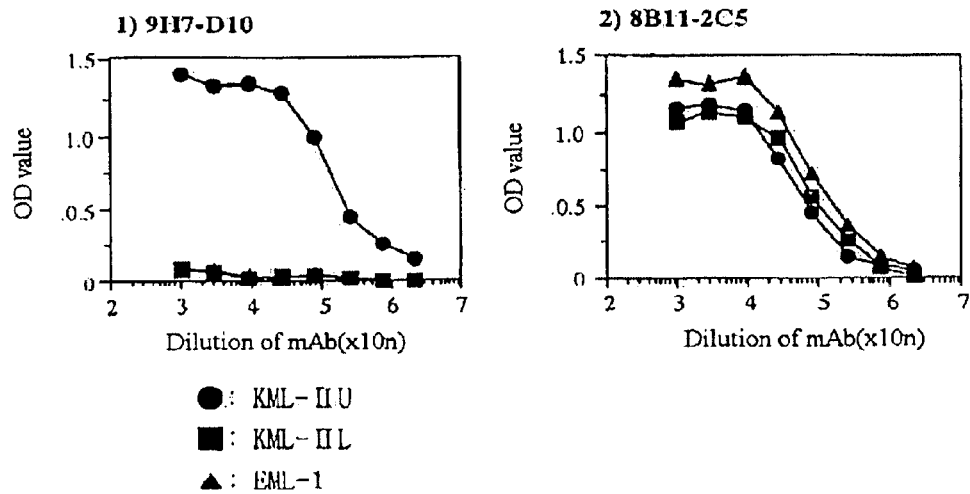
FIGS. 27A–27B show the cross reaction of monoclonal antibodies 9H7-D10 and 8B11-2C5 with KML-IIU, KML-IIL and EML-I.

| Lectin | Chain (Mw.) | Amino Acid Sequence | | | | |
|---|---|---|---|---|---|---|
| | | 1 | 10 | 20 | 30 | |
| KML-IIU | A (30 KDa) | YEREK | LRVTH | QTTGD | QYFKF ITLLA DQHS | (SEQ. ID. NO. 19) |
| KML-IIL | A (27.5 KDa) | YEREK | LRVTH | QTTGD | EYFRF ITLLA DTV | (SEQ. ID. NO. 20) |
| EML-I | A (29 KDa) | YEREK | LRVTH | QTTGD | EYFRF ITLLA DTVSS | (SEQ. ID. NO. 21) |
| KML-IIU | B (32.5 KDa) | unidentified | | | | |
| KML-IIL | B (31 KDa) | DVTXT | ASEPT | VRI | | (SEQ. ID. NO. 22) |
| EML-I | B (34 KDa) | DDVTS | SASEP | TVRIV | GRNGM | (SEQ. ID. NO. 23) | plates and allowed to react with various concentrations of each of KML-IIU, KML-IIL and EML-I. Thereafter, by taking advantage of a periodate method, an HRP conjugate was added to the 9H7-D10 and 8B11-2C5 to examine the reactivity between lectins and monoclonal antibodies. The result is given in FIG. 27. Without a cross-reaction with KML-IIL and EML-1, 9H7-D10 antibody showed specific reactivity for KML-IIU. On the other hand, 8B11-2C5 antibody reacted with all of KML-IIU, KML-IIL and EML-1.

Figure 28:
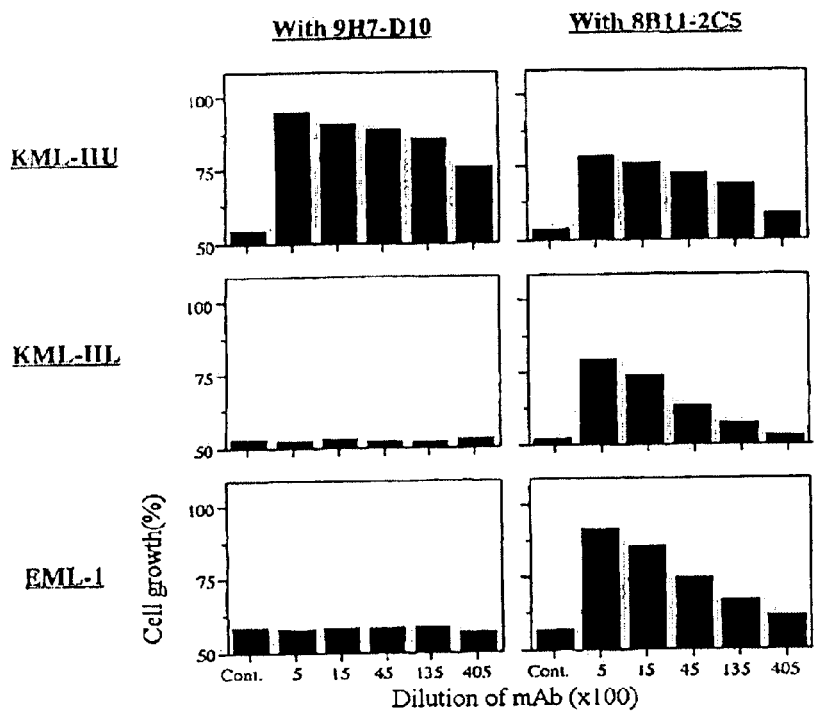
FIG. 28 shows the neutralization effects of monoclonal 9H7-D10 and 8B11-2C5 on the cytotoxicity of each lectin.

On the basis of this result, an examination was made of the neutralization effect of the monoclonal antibodies on the cytotoxicity of the lectins (FIG. 28). As seen in FIG. 28, 9H7-D10 antibody could neutralize the cytotoxicity of KML-IIU only, whereas 8B11-2C5 antibody showed cytotoxicity neutralization activity over KML-II, KML-IIL and EML-I. As apparent from the data of FIG. 28, KML-IIU and KML-IIL are different in at least epitope from EML-1.

8B11-2C5 antibody was of cross-reactivity to all Korean and European lectins. Thus, KML-IIU and EML-I may be identical to each other or have remarkably similar epitopes. However, KML-IIL is a lectin probably different from EML-I when account is taken of the following aspects: KML-IIL is different in sugar specificity and B-chain amino acid sequence from EML-I in addition to having 10-folds more potent cytotoxicity than does EML-I.

EXAMPLE 15

Induction of Cytokines from Macrophage by KML-IIU and KML-IIL

Figure 29:
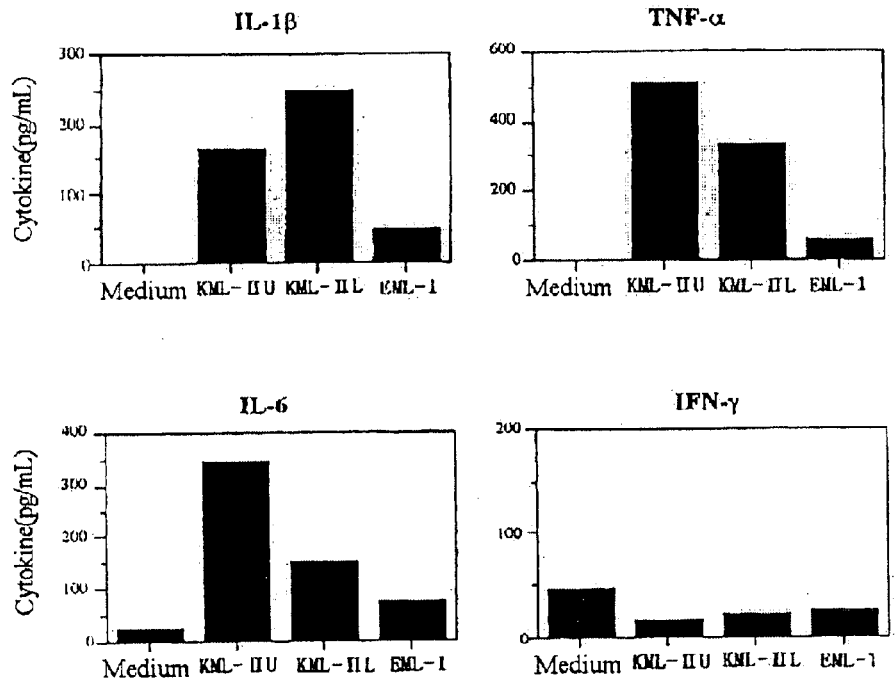
FIG. 29 shows the comparison in cytokine induction activity of KML-II and KML-IIL with EML-I.

The cytokine induction activity of KML-IIU and KML-IIL, both isolated from KML-C, was compared with that of EML-I by the same ELISA as in Example 4. When stimulating macrophages, each lectin was used at a concentration of 50 ng/ml. The result is given in FIG. 29. KML-IIU and KML-IIL directly stimulated mouse macrophages to induce IL-1, IL-6 and TNF-α, but were lacking in the induction of IFN-γ. Slightly different as they were from each other depending on cytokines, KML-IIU and KML-IIL were both superior to EML-I in cytokine induction activity. Consequently, an activity difference as well as a biochemical difference resides between Korean and European mistletoes.

EXAMPLE 16

Repressive Effect of KML-IIU and KML-IIL on Tumor Metastasis

Figure 30:
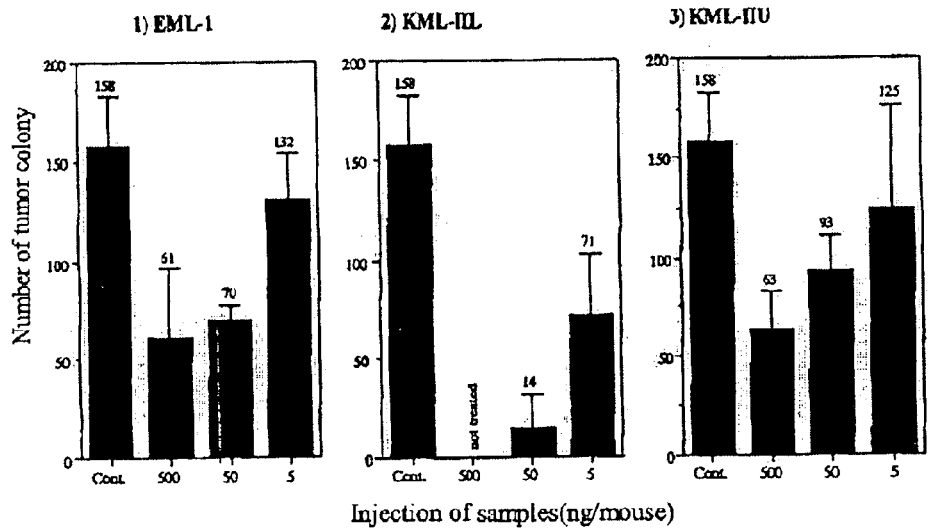
FIG. 30 shows the repressive activity of lectins on tumor metastasis, based on their cytotoxicity and cytokine induction activity.

Based on the cytotoxicity and cytokine induction activity, the two lectins were examined for in vivo repressive activity against tumor metastasis. Selected as a tumor cell line used for this experiment was colon 26-M3.1 lung carcinoma and before a couple of days of tumor inoculation, mice were administered with the samples of interest by i.v. injection. Each lectin was used at doses from 1 to 100 ng per mouse. The result is given in FIG. 30. KML-IIU and EML-I showed similar activity against tumor metastasis when being administered at doses of 50–100 ng. KML-IIL was active at a dose 10-folds lower than that of KML-IIU and EML-I and thus, the suitable dose at which KML-IIL can exert antitumoral activity in mice ranges from 5 to 50 ng. Thus, KML-IIL was interpreted to be 10-folds more potent in in vivo antitumoral activity than KML-IIU.

EXAMPLE 17

Anti-HBV Antibody Productivity of KML-IIU and KML-IIL

Comparison was made of immunological enhancement among KM-110, KML-IIU and KML-IIL. Used as an antigen was the pre-S2 domain of hepatitis B virus (HBV), which is of pathogenicity. Mice, which were grouped in fives, were immunized with the antigen by s.c. injection at two week intervals twice in total and, to fifteen weeks, sera were taken from the immunized mice to examine antibody titers. As a control, a 20% aluminum hydroxide adjuvant was employed. With regard to the ELISA to determine the antibody titer, the antigen was coated at an amount of 5 µg/ml on each well of ELISA plates and allowed to react with various concentrations of anti-sera. To quantitatively measure antigen-antibody complexes, an HRP-conjugated secondary anti-mouse antibody (rabbit-anti-mouse-IgG+A+ M-HRP; X8000, Zymed) was used. As a substrate for the enzyme reaction, TMB (Sigma) was added to the wells, followed by measuring absorbance at 450 nm (O.D.). The antibody titers were expressed as serum dilution ratios at which the O.D. of interest was three times as large as that of normal mice.

Figure 31:
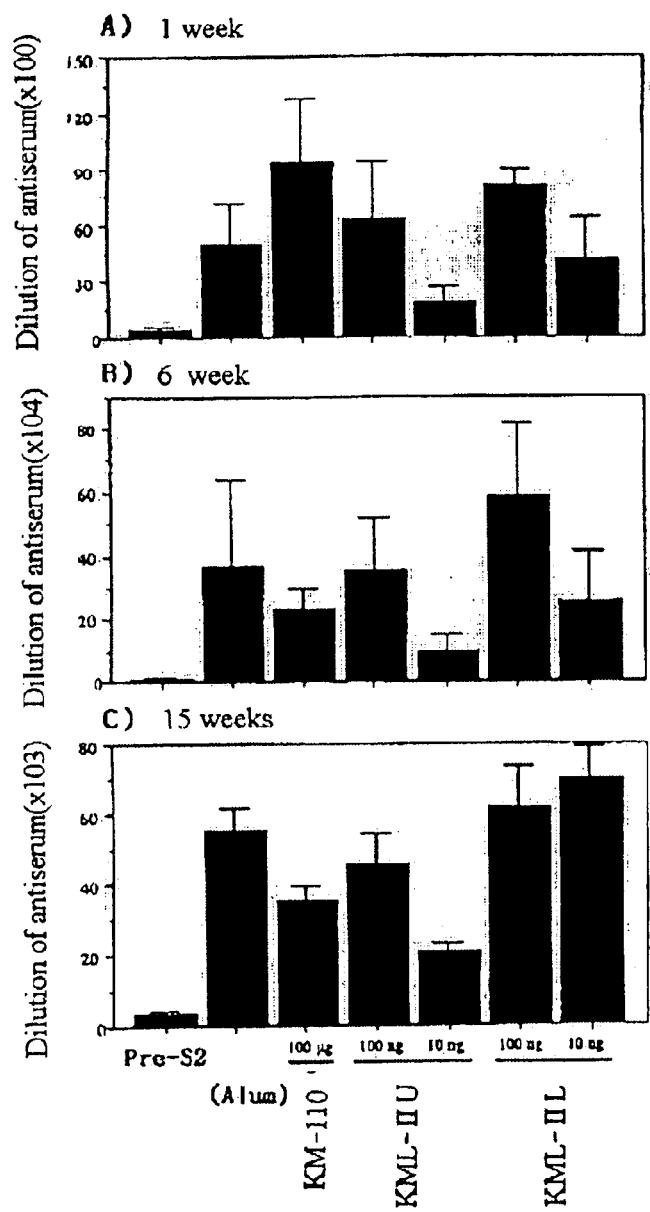

As shown in FIG. 31, KM-110 or each lectin adjuvant showed higher antibody titer than did the control, aluminum hydroxide adjuvant, in the first week after the initial immunization. Although aluminum-based adjuvants are generally known to show rapid responses, KM-110 and each lectin induced higher initial immune responses than the aluminum-based adjuvant. In the second week after the booster injection, KM-110 and KML-IIU were similar in antibody titer to the aluminum-based adjuvant, but KML-IIL showed an antibody titer twice larger than those of the other samples. Similar to the aluminum-based adjuvant in the aspect of maintaining antibody production, the adjuvants of the invention could induce antigen-specific antibody production until the fifth week of the initial immunization. As in the activity against tumor metastasis, the activity of the adjuvants, which have influence on the antibody productivity, turned out to be better in KML-IIL than in KML-IIU.

EXAMPLE 18

Partial Cloning of Korean Mistletoe Lectin Gene

Based on the amino acid sequences of purified KML-IIU and KML-IIL, two oligonucleotide primers were designed:

Primer 1: 5'-GTIACICAT CAIACIGG-3' (SEQ. ID. NO. 17)

Primer 2: 5'-ACIATICGC ACIFTIGGTC-3' (SEQ. ID. NO. 18)

Figure 32:
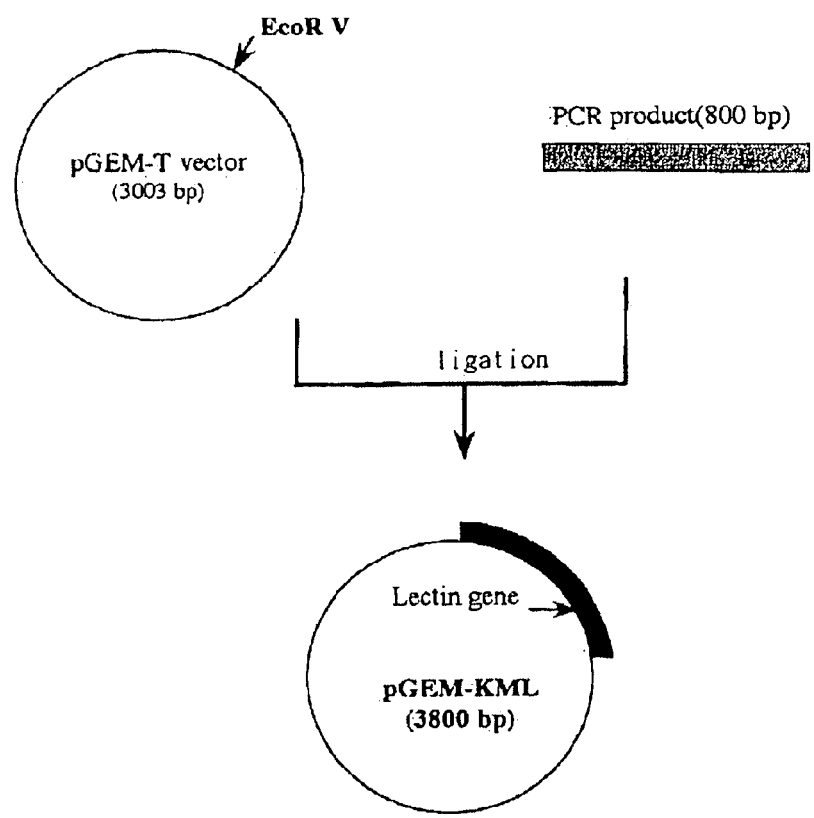
FIG. 32 is a schematic view showing a recombinant plasmid carrying a cloned lectin gene.

These primers were used to amplify a portion of the gene of interest by PCR with the genomic DNA of Korean mistletoe serving as a template. In this regard, a PCR reaction comprising 1 µg of the genomic DNA isolated by a CTAB method, 100 pmol of each primer, 200 µl of each dNTP, 1.5 mM $MgCl_2$, and 2.5 units of a DNA polymerase (Amplitaq, Perkin-Elmer) was subjected to 35 cycles of PCR, each consisting of a denaturing step at 94° C. for 1 min, an annealing step at 45° C. for 2 min and an extending step at 72° C. for 2 min, in a thermal cycler (Perkin-Elmer 9600). The PCR product, about 800 bp in length, was ligated into pGEM-T (Promega) at an EcoRV cloning site. The recombinant plasmid thus obtained was shown in FIG. 32.

EXAMPLE 19

Partial Base Sequence of Korean Mistletoe Lectin Gene and its Amino Acid Sequence Of the clones obtained, two were sequenced with the aid of an automated sequencer to determine their DNA base sequences for a KML-IIU gene and for a KML-IIL gene. In general, plant lectins are reported to exist as various isoforms. Also, there are some differences in base sequence among the clones, suggesting that there might exist various isoforms of Korean mistletoe.

Figure 33:
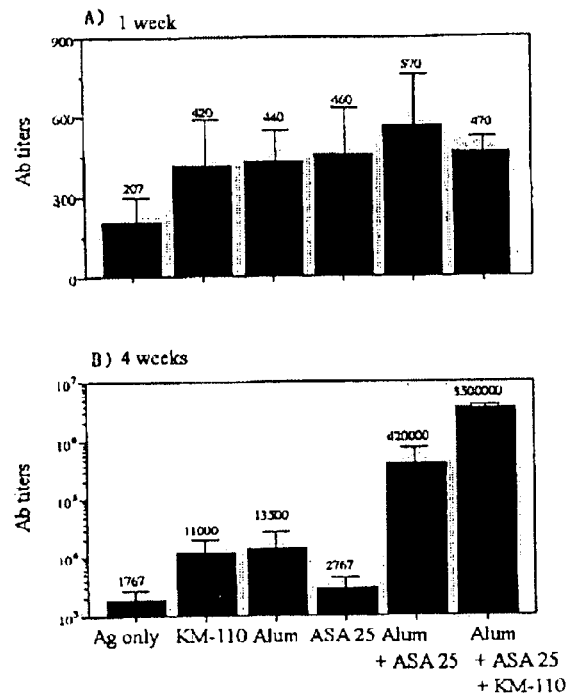
FIGS. 33A–33B show the synergistic activity in anti-mycoplasma antibody production, induced by composite adjuvants containing KML-110.
Figure 34:
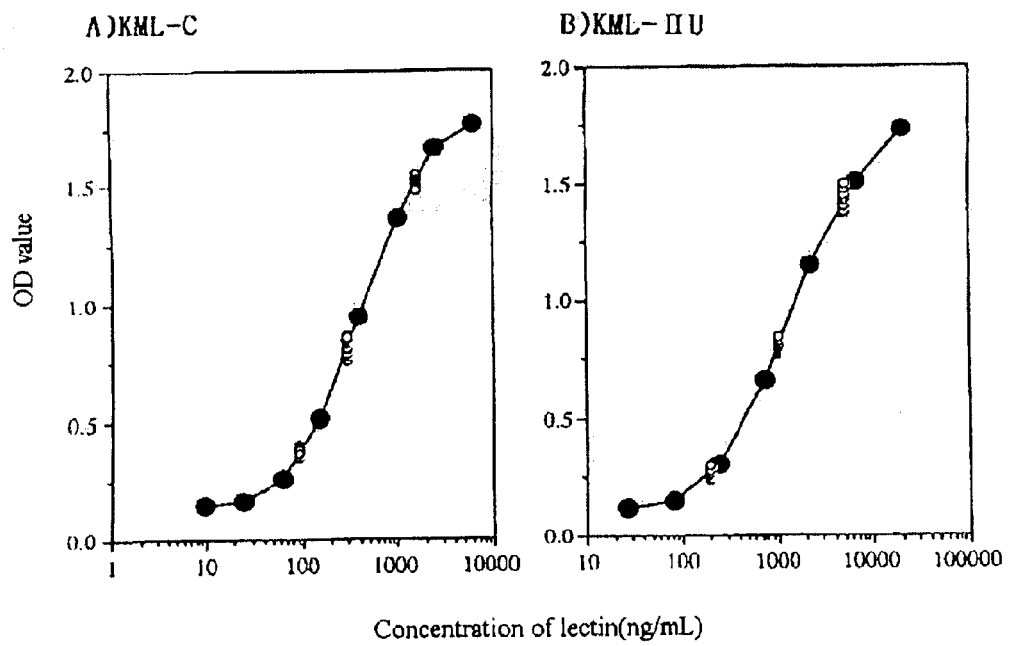
FIGS. 34A–34B are standard curves based on Sandwich ELISA for KML-C(A) and KML-IIU (B).

From the DNA base sequences, amino acid sequences were deduced (FIGS. 33 and 34), and are listed in Tables 9a to 9d, below, along with other plant lectins' for comparison. In Tables 9a to 9d, "IIU" stands for the amino acid sequence of purified KML-IIU, "IIL" for the amino acid sequence of purified KML-IIU", "C1" for the amino acid sequence deduced from the DNA base sequence of PCR product clone 1, "C2" for the amino acid sequence deduced from the DNA base sequence of PCR product clone 2, "EMLA" for the amino acid sequence of European mistletoe lectin I A-chain, "EMLB" for the amino acid sequence of European mistletoe lectin I B-chain, "RTA" for the amino acid sequence of ricin toxin B-chain, "ABA" for the amino acid sequence of abrin A-chain, and "ABB" for the amino acid of abrin B-chain.

TABLE 9a

Amino Acid Sequence Comparison of Korean Mistletoe Lectins, European Mistletoe Lectins, and Other Related Lectins <A Chain>

```
II U        Y E R L K L Y — V T H                                    (SEQ ID NO: 24)
II L        Y E R L R L R — V T H Q T T G D E Y F R F I T L L R D    (SEQ ID NO: 25)
CI                          H Q T T G D E Y F R F I T L L R D        (SEQ ID NO: 26)
EMLA        Y E R L R L R — V T H Q T T G E E Y F R F I T L L R D    (SEQ ID NO: 27)
RTA     I F P K Q Y P I I N F T T A G A T V Q S Y T N F I R A V R G  (SEQ ID NO: 28)
ABA           E D R P I — K F S T E G A T S Q S Y K Q F I E A L R E  (SEQ ID NO: 29)
II U
II L  Y V                                                            (SEQ ID NO: 30)
CI      Y V S S G S F S N E I P L L R Q S T I P V S D A Q R F V L    (SEQ ID NO: 31)

EMLA Y V S S G S P S N   E I P L L R Q S T I P V S D A Q R F V L     (SEQ. ID. NO. 32)
RTA  R L T T G A D V R H E I P V L P N R V G L P — I N Q R F I L     (SEQ. ID. NO. 33)
ABA  R L R G G L — — I H D I P V L P D P T T L Q — E R L R Y I T     (SEQ. ID. NO. 34)
CI   V E L T N Q G G D–S I T A A I D V T N L Y V V A Y Q A G D       (SEQ. ID. NO. 35)
EMLA V E L T N Q G Q D–S V T T A I D V T N A Y V V A Y Q A G D       (SEQ. ID. NO. 36)
RFA  V E L S N H A — E L S V T L A E D V T N A Y V V G Y R A G N     (SEQ. ID. NO. 37)
ANA  V E L S N S D T E — S I E V G I D V T N A Y V V A Y R A G T     (SEQ. ID. NO. 38)
CI   Q S Y F L R — D A P D G A E — — R H L F T G T T R — — — — —    (SEQ. ID. NO. 39)
EMLA Q S Y F L R — D A P R G A E — — T H L F T G T T R — — — — —    (SEQ. ID. NO. 40)
RTA  S A Y F F H P D N Q E D A E A I T H L F T — — — — D V Q N R     (SEQ. ID. NO. 41)
ABA  Q S Y F L R   D A P S S A S D Y — — L F T G T — — D — Q H —    (SEQ. ID. NO. 42)
CI   S S L P F T G S Y T D — L E R Y A G H — — R D Q I P L G — —    (SEQ. ID. NO. 43)
EMLA S S L P F N G S Y P D — L E R Y A G H — — R D Q I P L G — —    (SEQ. ID. NO. 44)
RTA  Y F T A F G G N Y — D P L E Q L A G — N L R E N I E L G N G    (SEQ. ID. NO. 45)
ABA  — S L P F Y G T Y G D — L E R W A — H Q S R Q Q I P L G L D    (SEQ. ID. NO. 46)
```

TABLE 9b

Amino Acid Sequence Comparison of Korean Mistletoe Lectins, European Mistletoe Lectins, and Other Related Lectins <A chain>

```
C1   — I E E L I Q S V S A L — — I Y P G G — — — S T R A Q A R S     (SEQ. ID. NO. 47)
EMLA — I D Q L I Q S V T A L — — I F P G G — — — S T R T Q A R S     (SEQ. ID. NO. 48)
RTA  P L E E A I — — — S A L Y Y Y S Y G G T Q L P T L — — A R S    (SEQ. ID. NO. 49)
ABA  A L T H G T — — — S F F — — R S — G G N D N E E K — — A R T    (SEQ. ID. NO. 50)
C2                   A R F N P I X W R L R R Q — I N S G E S        (SEQ. ID. NO. 51)
C1   L I I L I Q M I S E A A R F N P I F W R — A R Q Y I N S G E S  (SEQ. ID. NO. 52)
EMLA I L I L I Q M I S E A A R F N P I L W R — Y R Q Y I N S G A S  (SEQ. ID. NO. 53)
RTA  F I I C I Q M I S E A A R F Q Y I E G E — M R T R I R Y N R R  (SEQ. ID. NO. 54)
ABA  L I V I I Q M V A E A A R F R Y I S N R — V R V S I Q T G T A  (SEQ. ID. NO. 55)
C2   S S P P N Y M L E L E T S W G R Q S T Q V Q Q S K — D G I F    (SEQ. ID. NO. 56)
C1   F L P D M Y M L E L E T S W G Q Q S T Q V Q Q S T — D G V F    (SEQ. ID. NO. 57)
EMLA F L P D V Y M L E L E T S W G Q Q S T Q V Q H S T — D G V F    (SEQ. ID. NO. 58)
RFA  S A P D P S V I T L E N S W G R L S T A I Q E S N Q G A — F    (SEQ. ID. NO. 59)
ABA  F Q P D A A M I S L E N M W D N L S R G V Q E S V Q D T — F    (SEQ. ID. NO. 60)
C2   N T Q I R L — Q I S A G M F — V — T S X N V R D V — I — — S    (SEQ. ID. NO. 61)
C1   N N P F R L — G I S T G M F — V — T L S N V R D V — I — — A    (SEQ. ID. NO. 62)
EMLA N N P I R L — A I P P G M F — V — T L T N V R D V — I — — A    (SEQ. ID. NO. 63)
RTA  — — — — — A S P I Q L Q R R — N G S K F S V Y D V S I L I P    (SEQ. ID. NO. 64)
ABA  P N Q V T L T N I R N E P V I V D S L S H P T — V — — — — A    (SEQ. ID. NO. 65)
C2   S L A I M L F E C S G R P F S S                                (SEQ. ID. NO. 66)
C1   S L A I M L F V C R D R P S S S                                (SEQ. ID. NO. 67)
EMLA S L A I M L F V C G E R P S S S                                (SEQ. ID. NO. 68)
RTA  I I A L M V Y R C A P P P S S Q F                              (SEQ. ID. NO. 69)
ABA  V L A L M L F V C N P P P P N                                  (SEQ. ID. NO. 70)
```

TABLE 9C

Amino Acid Sequence Comparison of Korean Mistletoe Lectins, European Mistletoe Lectins, and Other Related Lectins <Linker>

| | | |
|---|---|---|
| C2 | L D H P S P L L L R S V V D A A N | (SEQ. ID. NO. 71) |
| C1 | D V R Y W P L V I R P V L E N S G A V | (SEQ. ID. NO. 72) |
| EMLA | | |
| RTA | S L – L L I R P V V P N F N | (SEQ. ID. NO. 73) |
| ABA | A N Q S P L L I R S | (SEQ. ID. NO. 74) |

TABLE 9d

Amino Acid Sequence Comparison of Korean Mistletoe Lectins, European Mistletoe Lectins, and Other Related Lectins <B chain>

| | | |
|---|---|---|
| IIL | D V T C T A S E C T V R I | (SEQ. ID. NO. 75) |
| C2 | D V T X T X S E P T V R I V | (SEQ. ID. NO. 76) |
| C1 | D D V T C T A S E P T V R I V | (SEQ. ID. NO. 77) |
| EMLB | D D V T S S A S E P T V R I V G R N G M | (SEQ. ID. NO. 78) |
| RTB | A D V C M D P – E P I V R I V G R N G M | (SEQ. ID. NO. 79) |
| ABB | S K I C S S R Y E P T V R I G G R D G M | (SEQ. ID. NO. 80) |

EXAMPLE 20

Imunological Enhancement Effect of Complex Adjuvant Containing Mistletoe

In this experiment, immunologically effective, novel adjuvant formulations were prepared by combining KM-110 with conventional adjuvants. If a synergistic activity is induced in the combinations by KM-110, various adjuvants can be developed by use of KM-110. Since adjuvants should be generally active against a broad spectrum of antigens, mycoplasma, which is one of the pathogenic bacteria causing pneumonia in domestic animals, was utilized in this experiment. The antibody titer was measured in the same manner as in Example 9 and the result is shown in FIG. 35. As conventional adjuvants, 20% aluminum hydroxide and 3% oil ASA25 were employed. As a result of the experiment, a combination of 100 μg of KM-110 and an alum adjuvant was recognized to be active for the enhancement of antibody production, showing a similar effect to that obtained in Example 9. In contrast, a combination of KM-110 and the oil was poor in antibody productivity, compared with the combination of KM-110 and alum adjuvant. A couple of weeks after the booster injection with antigen, a combination of alum adjuvant and ASA25 induced about 5-folds greater antibody titer than did each of the adjuvants. That is, when the conventional adjuvants were combined, a better synergistic effect was induced than when the conventional adjuvants were used singly. When KM-110 was additionally nil combined with the combination of alum adjuvant and ASA25, the resulting adjuvant made the antibodies produced at an antibody titer about 10 times as large as that obtained when the conventional adjuvants were used singly. Therefore, a significant immunological enhancement effect was obtained by adding KM-110 to conventional adjuvants, indicating that KM-110 can be used to prepare immunologically more effective adjuvants.

EXAMPLE 21

Lectin Contents in Extracts from Mistletoes Parasitic on Different Hosts

As revealed above, the antitumoral activity or the immunological enhancement effect of KM-110 is dependent mainly on its lectin fractions. Because lectin plays a role as an index material indicating the activity of the crude extract KM-110, development of a method for measuring the content of lectin has an important significance. In this example, an immuno assay method (sandwich ELISA) by which contents of KML-C and KML-IIU can be measured was developed by taking advantage of 9H7-D10, which is a monoclonal antibody specific for KML-IIU, and 8B11-2C5, which is of cross-reactivity with KML-IIU and KML-IIL. To this end, HRP was first conjugated to 9H7-D10 and 8B11-2C5 antibodies by a Lamini method with the aim of measuring the content of each lectin. As a coating Ab for a sandwich ELISA, 8E12-3E9 (x1,000), which is of an IgM type, was employed. After the antibodies were blocked by BSA, each lectin was diluted in series and allowed to react with the antibodies. After completion of the reaction, HRP-conjugated 9H7-D10 and 8B11-2C5 antibodies was reacted to their corresponding lectins. Addition of a TMB buffer induced a coloring reaction. Standard curves for KML-C and KML-IIU, which were drawn by use of sandwich ELISA, made KML-C and KML-IIU known to be detected in the range of 30 ng-2.5 μg/ml and 80 ng-5 μg/ml, respectively, as shown in FIG. 36. When applied to the standard curves of FIG. 6, the lectin contents of the mistletoes parasitic on 6 host trees were measured as shown in Table 10, below.

TABLE 10

Lectin and Total Protein Contents in Mistletoe Extracts According to Host Trees

| Host Trees | Leaves | Protein (μg) | KML-C (μg) | KML-IIU (μg) |
|---|---|---|---|---|
| Quercus | 200 mg | 1864 | 64.8 ± 8.6 | 33.8 ± 2.5 |
| Catanea | 200 mg | 1471 | 459.7 ± 22.4 | 235.4 ± 12.5 |
| Chaenomeles | 200 mg | 1755 | 112.9 ± 10.7 | 55.8 ± 5.5 |
| Prunus | 200 mg | 1258 | 710.2 ± 31.7 | 429.7 ± 36.5 |
| Ailanthus | 200 mg | 935 | 88.8 ± 8.2 | 47.2 ± 3.8 |
| Pyrus | 200 mg | 748 | 94.5 ± 7.3 | 52.9 ± 5.2 |

The protein contents were different from one host tree to another, as shown in Table 10. The total protein content in 200 mg of each mistletoe was widely changed in accordance with host trees, ranging from 748 μg to as much as 1864 μg, which can be calculated as being from 0.374 to ED 0.923 weight by percentage. As measured by ELISA, KML-C amounted to 3.6% in the total protein amount of *Quercus*-parasitic mistletoe and to 50% in the total protein amount of *Prunus*-parasitic mistletoe: the latter is 21 times as great as the former. In the case of *Castanea*, the content of KML-C in the total protein was measured to be as much as 30%. Based on the weight of the total protein, the parasitic mistletoe contained KML-C at an amount of 5.6% in case of *Chaenomeles* host, at an amount of 8.2% in case of *Ailanthus* host, and at an amount of 12.7% in case of *Pyrus* host. As for the percentage of KML-IIU in KML-C, it was calculated to be 53.7±3.9% on average, in the six host trees. Since the anticancer activity induced by the immune action of mistletoe has been revealed to be due mainly to the KML-C, thus far, the immunological enhancement of Korean mistletoe extracts is believed to be quite different from one host tree to another. The activity KMHBP and other active materials also might be different depending on hosts.

EXAMPLE 22

In Vitro Cytotoxicity Effects of Extracts of Mistletoes Parasitic on Different Hosts A measurement was made of the in vitro cytotoxicity effect that the extracts from mistletoes parasitic on different hosts exerted on various tumor cells. The in vitro anticancer activity of each mistletoe extract was expressed as the concentration ($IC_{50}$) at which each extract effectively inhibited the growth of each cell strain by 50%. As seen in Table 11, mistletoe extracts inhibited the growth of tumor cells at different activities according to the cell lines. In addition, the inhibitory activity was dependent on the hosts, showing a proportional relation to the lectin content in each mistletoe extract. The inhibitory activity against YAC-1 cell for example, was determined at $IC_{50}$ of 200 ng/ml for *Quercus*, 30 ng/ml for *Castanea*, 150 ng/ml for *Chaenomeles*, 5.6 ng/ml *Prunus*, 90 ng/ml for *Ailanthus*, and 60 ng/ml for *Pyrus*. The highest cytotoxicity was obtained from the extract from the *Prunus*-parasitic mistletoe extract which was highest in lectin content as measured by a lectin assay.

The immunological enhancement effect of the extracts from the mistletoes parasitic on different hosts was also found to come mainly from the lectin component KML-C.

TABLE 11

Killing Effect on Various Tumor Cell Lines Induced by Mistletoe Extracts from Various Host Trees

| Cell Lines | Conc. to Inhibit Tumor Cell Growth by 50% ($IC_{50}$) (ng/mL) | | | | | |
|---|---|---|---|---|---|---|
| | Quercus | Castanea | Chaenomeles | Prunus | Ailanthus | Pyrus |
| YAC-1 | 2100 | 400 | 1600 | 90 | 1800 | 1600 |
| RAW | 2500 | 1600 | 1700 | 590 | 2200 | 2600 |
| Molt-4 | 1400 | 500 | 1000 | 140 | 1000 | 1000 |

EXAMPLE 23

Immunological Stimulation by KMHBP and Lectin Fraction Combinations

As revealed in Example 4, the effective concentration at which the lectin fraction KML-C can induce cytokines such as TNF-α, IL-1 and IL-6 ranges from 5 to 100 ng/ml. For the induction of IFN-γ, KMHBP has an effective concentration range from 1 to 5 μg/ml. Based on these results, 2 μg of KMHBP and 20 ng of KML-C were mixed in 1 ml of PBS (the resulting fraction is, hereinafter, referred to as "KM") and KM was examined for the cytokine induction ability from lymphocytes of the spleen of normal mice in the same manner as in Example 4. The result is given in Table 12, below. The KM fraction was found to effectively induce all of the cytokines tested, TNF-α, IL-1, IFN-γ and IL-6.

TABLE 12

Activity of KM Fraction to Induce Cytokines

| Samples | Cytokines | | | | Cytotoxixity $IC_{50}$: ng/mL |
|---|---|---|---|---|---|
| | IL-1 | TNF-a | IFN-γ | IL-6 | |
| KML-C (20 ng) | 172 ± 25 | 311 ± 26 | 0 | 313 ± 15 | 2.5 ± 0.3 |
| KM-AS (2 μg) | 169 ± 12 | 220 ± 31 | 162 ± 20 | 220 ± 22 | 30 ± 2.5 |
| KMHBP-100 (2 μg) | 0 | 25 ± 4 | 356 ± 42 | 156 ± 22 | 1560 ± 62 |
| KM (2 μg) | 195 ± 21 | 256 ± 31 | 292 ± 21 | 286 ± 35 | 225 ± 13 |

This data shows that the KM fraction is endowed with the KMHBP's ability to induce INF-γ, which is not induced by lectins, in addition to being similar in induction activity to KM-110 or KM-AS with a great decrease in direct cytotoxicity on normal cells. KM showed 7 times as low direct cytotoxicity on normal cells as KMHBP-100. Therefore, the KM fraction is improved not only in cytokine induction activity, but also in safety to normal cells.

EXAMPLE 24

In Vivo Toxicity of KM Fraction

The KM fraction was measured for in vivo acute toxicity in the same manner as in Example 6 and the result is given in Table 13, below. In this experiment, KM-AS, a protein fraction of KM-110, was used as a control.

As seen in Table 13, KM-AS has an LD., of 10–15 μg/mouse while 75 μg/mouse was given to the $LD_{50}$ of the KM fraction. In the group which was administered with KM at 100 μg/mouse, no mice were found to die a sudden death within 6 hours. The mouse members all suffered from piloerection and adynamia due to the pyrexia caused by the induction of excessive inflammatory cytokines and were finally put to death within 72 hours. The mice survived in the group which was administered with $LD_{50}$ of KM, that is, 75 μg/?kg, and were observed to suffer from piloerection and adynamia until the fifth day after the administration and then, revived to the normal state. In contrast to the KM fraction, the KM-AS fraction caused mice to undergo adynamia immediately after the injection at a dose of 15 μg/kg? and died within 24 hours after the injection. All mice of the group injected with KM-AS at a dose of 10 μg/kg? survived. In them, a slight adynamia and piloerection was observed for 1–3 days after the injection, and then, they revived. Thus, KM-AS, a protein fraction of KM-110, contained a material or materials lethal to mice. The KM fraction, composed of KMHBP, separated through a heparin column, and KML-C, did not cause a sudden death in mice, so that the lethal material(s) was removed by the separation through the heparin column.

TABLE 13

Mortality Upon Intravenous Injection of KM Fraction

| Samples | Dose | Days/Viability (%) | | | | | | | Results (%) |
|---|---|---|---|---|---|---|---|---|---|
| | | 1 | 2 | 3 | 4 | 5 | 6 | 7 | |
| KM-AS | 15 μg | 0 | — | — | — | — | — | — | 0 |
| KM | 10 μg | 100 | 100 | 100 | 100 | 100 | 100 | 100 | 100 |
| | 100 μg | 40 | 20 | 0 | — | — | — | — | 0 |
| | 75 μg | 80 | 40 | 40 | 40 | 40 | 40 | 40 | 40 |
| | 50 μg | 100 | 100 | 100 | 100 | 100 | 100 | 100 | 100 |
| | 25 μg | 100 | 100 | 100 | 100 | 100 | 100 | 100 | 100 |

EXAMPLE 25

Repressive Activity of KM Fraction Against Tumor Metastasis

The KM fraction was examined for the repressive activity against tumor metastasis. Preventive effects of KM fractions on cancer cells were made as described in Example 7 while KM-110 (100 μg), KM-AS (2 μg) and KML-C were used as positive controls. As given in Table 14, below, no differences existed between the positive control group and KM, indicating that the KM fraction maintained the activity of KM-110 as it was.

TABLE 14

Repressive Activity of KM Fraction Against Tumor Metastasis

| Samples | Dose | Lung Cancer No. ± SD (% Inhibition) | Ranges |
|---|---|---|---|
| Control | — | 186 ± 25 (—) | 156–210 |
| KM-100 | 100 μg | 25 ± 6 (86.6) | 19–32 |
| KM-AS | 2 μg | 22 ± 8 (88.2) | 15–30 |
| KML-C | 50 ng | 30 ± 6 (83.9) | 24–37 |
| KM | 5 μg | 20 ± 5 (89.2) | 15–25 |
| KM | 1 μ | 22 ± 6 (88.2) | 16–28 |
| KM | 200 ng | 40 ± 7 (78.5) | 32–49 |

Taken together, the data obtained above demonstrate that the Korean mistletoe extract KM-110 and its purified fractions, such as, the KM-110-derived protein fraction KM-AS, the lectin fraction KML-C, the two lectins KML-IIU and KML-IIL, the protein KMHBP, separated through heparin column from C-free AS which is a fraction of KM-AS free of KML-C, and the mixed fraction KM containing the KMHBP and the KML-C, each has the functions of stimulating humoral and cell-mediated immune systems to enhance the totality of host immune mechanisms as well as of activating macrophages and natural killer cells, both taking direct and indirect part in controlling tumor cells, to improve the antitumoral activity of hosts. Therefore, the present invention finds numerous applications in the biological, medicinal, pharmacological and immunological industries.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

SEQUENCE LISTING

<160> NUMBER OF SEQ ID NOS: 80

<210> SEQ ID NO 1
<211> LENGTH: 762
<212> TYPE: DNA
<213> ORGANISM: Viscum album coloratum
<220> FEATURE:
<221> NAME/KEY: misc_feature

<400> SEQUENCE: 1

```
tacgagaggc taagactcag agttacgcat caaaccacgg gcgacgaata tttccggttc      60
atcacgcttc tccgagatta tgtctcaagc ggaagctttt ccaatgagat accactcttg     120
cgtcagtcta cgatccccgt ctcggatgcg caaagatttg tgttggtgga actcaccaat     180
```

```
cagggggggag actcgatcac ggccgccatc gacgttacta acctgtacgt ggtggcttac    240
caagcaggcg accaatccta cttttttgcgc gacgcaccag acggcgcgga aaggcatctc    300
ttcaccggca ccaccagatc ctccctccca ttcaccggaa gctacacaga tctggagcga    360
ttcgccggtc ataggaccag atccctctg ggtagagagg aactcattca atccgtctcg    420
gcccttcgtt ttccgggcag caacactcgt gcccaagctc gttcctttat catcctcatt    480
cagatgatct ccgaggccgc cagattcaat cccatcttat ggagggctcg ccaatacatt    540
agcagtgggg ggtcatttct gccagacacg tacattctcc agctggagac gagttggggg    600
caacaatcca cgcaagttca gcactcgacg gatggcgttt taataaccc aattcggttg     660 actatatcca ctggtgtctt cgtgacgttg agcaatgttc gcgacgtgat cgccagctta    720
gcgatcatgt tgtttgtatg cgaggaccgg ccatcttcct ct                       762
```

<210> SEQ ID NO 2
<211> LENGTH: 254
<212> TYPE: PRT
<213> ORGANISM: Viscum album coloratum
<220> FEATURE:
<221> NAME/KEY: misc_feature

<400> SEQUENCE: 2

```
Tyr Glu Arg Leu Arg Leu Arg Val Thr His Gln Thr Thr Gly Asp Glu
 1               5                  10                  15

Tyr Phe Arg Phe Ile Thr Leu Leu Arg Asp Tyr Val Ser Ser Gly Ser
                20                  25                  30

Phe Ser Asn Glu Ile Pro Leu Leu Arg Gln Ser Thr Ile Pro Val Ser
            35                  40                  45

Asp Ala Gln Arg Phe Val Leu Val Glu Leu Thr Asn Gln Gly Gly Asp
        50                  55                  60

Ser Ile Thr Ala Ala Ile Asp Val Thr Asn Leu Tyr Val Val Ala Tyr
 65                  70                  75                  80

Gln Ala Gly Asp Gln Ser Tyr Phe Leu Arg Asp Ala Pro Asp Gly Ala
                85                  90                  95

Glu Arg His Leu Phe Thr Gly Thr Thr Arg Ser Ser Leu Pro Phe Thr
               100                 105                 110

Gly Ser Tyr Thr Asp Leu Glu Arg Phe Ala Gly His Arg Asp Gln Ile
            115                 120                 125

Pro Leu Gly Arg Glu Glu Leu Ile Gln Ser Val Ser Ala Leu Arg Phe
        130                 135                 140

Pro Gly Ser Asn Thr Arg Ala Gln Ala Arg Ser Phe Ile Ile Leu Ile
145                 150                 155                 160

Gln Met Ile Ser Glu Ala Ala Arg Phe Asn Pro Ile Leu Trp Arg Ala
                165                 170                 175

Arg Gln Tyr Ile Ser Ser Gly Ser Phe Leu Pro Asp Thr Tyr Ile
            180                 185                 190

Leu Gln Leu Glu Thr Ser Trp Gly Gln Gln Ser Thr Gln Val Gln His
        195                 200                 205

Ser Thr Asp Gly Val Phe Asn Asn Pro Ile Arg Leu Thr Ile Ser Thr
    210                 215                 220

Gly Val Phe Val Thr Leu Ser Asn Val Arg Asp Val Ile Ala Ser Leu
225                 230                 235                 240

Ala Ile Met Leu Phe Val Cys Glu Asp Arg Pro Ser Ser Ser
                245                 250
```

-continued

```
<210> SEQ ID NO 3
<211> LENGTH: 762
<212> TYPE: DNA
<213> ORGANISM: Viscum album coloratum
<220> FEATURE:

<400> SEQUENCE: 3
tacgagaggc taagactcag agttacgcat caaaccacgg gcgaccaata tttcaagttc      60
atcacgcttc tccgagatca tgtctcaagc ggaagcttgt ccaatcaaat accactcttg     120
cggcagtcta ctgtccccgt ctcggatacg cagagatttg tgttggtgga actcagcaat     180
caggggggag actcgatcac ggccgccatc gacgttacca atctgtacgt ggtggcttac     240
caagcaggca accaatccta cttttttgcgc gacgcacctc gcggcgcgga aacgtatctc     300
ttcaccggca ccacccgatc ctctctccca ttcaacggaa gctaccctga tctggagcga     360
tacgccggac atagggacca gatccctctc ggtatagacc aactcattca atccgtctcg     420
gcccttcgtt ttccgggcag caacactcgt gcccaagctc gttcctttat catcctcatt     480
cagatgatct ccgaggccgc cagattcaat cccatcttat ggaggctcg ccaatacatt      540 agcagtgggg ggtcatttct gccagacacg tacattctcc agctggagac gagttggggg     600
caacaatcca cgcaagttca gcactcgacg gatggcgttt ttaataaccc aattcggttg     660
actatatcca ctggtgtctt cgtgacgttg agcaatgttc gcgacgtgat cgccagcyta     720
gcgatcatgt tgtttgtatg cgaggaccgg ccatcttcct ct                        762

<210> SEQ ID NO 4
<211> LENGTH: 254
<212> TYPE: PRT
<213> ORGANISM: Viscum album coloratum
<220> FEATURE:
<221> NAME/KEY: misc_feature
<222> LOCATION: 240
<223> OTHER INFORMATION: Xaa = any amino acid

<400> SEQUENCE: 4

Tyr Glu Arg Leu Arg Leu Arg Val Thr His Gln Thr Thr Gly Asp Gln
 1               5                  10                  15

Tyr Phe Lys Phe Ile Thr Leu Leu Arg Asp His Val Ser Ser Gly Ser
                20                  25                  30

Leu Ser Asn Gln Ile Pro Leu Leu Arg Gln Ser Thr Val Pro Val Ser
            35                  40                  45

Asp Thr Gln Arg Phe Val Leu Val Glu Leu Ser Asn Gln Gly Gly Asp
        50                  55                  60

Ser Ile Thr Ala Ala Ile Asp Val Thr Asn Leu Tyr Val Val Ala Tyr
 65                  70                  75                  80

Gln Ala Gly Asn Gln Ser Tyr Phe Leu Arg Asp Ala Pro Arg Gly Ala
                85                  90                  95

Glu Thr Tyr Leu Phe Thr Gly Thr Thr Arg Ser Ser Leu Pro Phe Asn
            100                 105                 110

Gly Ser Tyr Pro Asp Leu Glu Arg Tyr Ala Gly His Arg Asp Gln Ile
        115                 120                 125

Pro Leu Gly Ile Asp Gln Leu Ile Gln Ser Val Ser Ala Leu Arg Phe
    130                 135                 140

Pro Gly Ser Asn Thr Arg Ala Gln Ala Arg Ser Phe Ile Ile Leu Ile
145                 150                 155                 160

Gln Met Ile Ser Glu Ala Ala Arg Phe Asn Pro Ile Leu Trp Arg Ala
                165                 170                 175
```

```
Arg Gln Tyr Ile Ser Ser Gly Gly Ser Phe Leu Pro Asp Thr Tyr Ile
            180                 185                 190

Leu Gln Leu Glu Thr Ser Trp Gly Gln Gln Ser Thr Gln Val Gln His
        195                 200                 205

Ser Thr Asp Gly Val Phe Asn Asn Pro Ile Arg Leu Thr Ile Ser Thr
    210                 215                 220

Gly Val Phe Val Thr Leu Ser Asn Val Arg Asp Val Ile Ala Ser Xaa
225                 230                 235                 240

Ala Ile Met Leu Phe Val Cys Glu Asp Arg Pro Ser Ser Ser
                245                 250
```

<210> SEQ ID NO 5
<211> LENGTH: 768
<212> TYPE: DNA
<213> ORGANISM: Viscum album coloratum
<220> FEATURE:
<221> NAME/KEY: misc_feature

<400> SEQUENCE: 5

```
tacgagaggc taagactcag agttacgcat caaaccacgg gcgacgaata tttccggttc      60
atcaagcttc tccgagactc tgtctcaagc ggaagctttt ccaatgacat accgctcctg     120
cctccgtcaa tcccggtctc ctctgcgcag agatttgtgt tggtggaact cacaaatcag     180
ttgggaaagt gggaagactc gatcacggcc gccatcgacg ttaccaatct gtacgtggtg     240
gcttaccaag caggcgacca atcctacttt ttgcgcgacg caccgacgg cgcggaaagg      300
catctcttca ccggcaccac cagatcctct cttcctttca acggaagcta cgctgatctg     360
gagcggtacg ccggacatag ggaccggatc cctctgggta gagagccact catacgatcc     420
gtctcggcgc ttgattatcc cggcggcagc acgcgcgccc aagccagttc cattattatc     480
gtcattcaga tgatctccga ggcggccaga ttcaatccca tcctatggag ggctcgccaa     540
tacattaaca gtggggtgtc atatcttcca gacgtgtaca tgctggagct ggaggcgagt     600
tggggccaac aatcgaccca agtccagcag tcgaccgatg cgttttttaa taacccaatt     660
cggttgggta tatccaccgg caacttcgtg tggttgagca atgttcgcga cgtgatcgcc     720
agcttgggga tcatggtgtt tgtatgcagg gaccggtcat cttcccct              768
```

<210> SEQ ID NO 6
<211> LENGTH: 256
<212> TYPE: PRT
<213> ORGANISM: Viscum album coloratum
<220> FEATURE:
<221> NAME/KEY: misc_feature

<400> SEQUENCE: 6

```
Tyr Glu Arg Leu Arg Leu Arg Val Thr His Gln Thr Thr Gly Asp Glu
  1               5                  10                  15

Tyr Phe Arg Phe Ile Lys Leu Leu Arg Asp Ser Val Ser Ser Gly Ser
             20                  25                  30

Phe Ser Asn Asp Ile Pro Leu Leu Pro Pro Ser Ile Pro Val Ser Ser
         35                  40                  45

Ala Gln Arg Phe Val Leu Val Glu Leu Thr Asn Gln Leu Gly Lys Trp
     50                  55                  60

Glu Asp Ser Ile Thr Ala Ala Ile Asp Val Thr Asn Leu Tyr Val Val
 65                  70                  75                  80

Ala Tyr Gln Ala Gly Asp Gln Ser Tyr Phe Leu Arg Asp Ala Pro Asp
                 85                  90                  95
```

Gly Ala Glu Arg His Leu Phe Thr Gly Thr Thr Arg Ser Ser Leu Pro
            100                 105                 110

Phe Asn Gly Ser Tyr Ala Asp Leu Glu Arg Tyr Ala Gly His Arg Asp
        115                 120                 125

Arg Ile Pro Leu Gly Arg Glu Pro Leu Ile Arg Ser Val Ser Ala Leu
    130                 135                 140

Asp Tyr Pro Gly Gly Ser Thr Arg Ala Gln Ala Ser Ser Ile Ile Ile
145                 150                 155                 160

Val Ile Gln Met Ile Ser Glu Ala Ala Arg Phe Asn Pro Ile Leu Trp
                165                 170                 175

Arg Ala Arg Gln Tyr Ile Asn Ser Gly Val Ser Tyr Leu Pro Asp Val
            180                 185                 190

Tyr Met Leu Glu Leu Glu Ala Ser Trp Gly Gln Ser Thr Gln Val
        195                 200                 205

Gln Gln Ser Thr Asp Gly Val Phe Asn Asn Pro Ile Arg Leu Gly Ile
    210                 215                 220

Ser Thr Gly Asn Phe Val Trp Leu Ser Asn Val Arg Asp Val Ile Ala
225                 230                 235                 240

Ser Leu Gly Ile Met Val Phe Val Cys Arg Asp Arg Ser Ser Pro
                245                 250                 255

<210> SEQ ID NO 7
<211> LENGTH: 797
<212> TYPE: DNA
<213> ORGANISM: Viscum album coloratum
<220> FEATURE:
<221> NAME/KEY: misc_feature

<400> SEQUENCE: 7

```
acgatgtaac ctgcactact tccgaaccta cggtacggtt tgtgggtcga atggcctgt      60
gtctcgacgt cccagagggc gattaccacg atggaagtcg atacagttg tggccctgca    120
agtccaactc cgatcagaat cagctgtgga cgatcagaag ggatggaacc attcgatcta    180
atggaaggtg cttgacgacc tatgggtata ctgcgggcag ctatataatg atctacgact    240
gtaatagagg ggggtgggac cttactactt ggcagataag gggcaatgga atcatcctta    300
atccaagatc catgatggtg atcggaacac catccgggag ccgcgaaacc cgtggcacta    360
cttttactct gcaaacactg ggttactcat taggacaggg ctggcttgcc agcaatgata    420
ccgctcctcg cgaggtaacc atatatggtt tccgcgatca ttgcatggaa actagtggag    480
ggaaagtgtg ggttgggact tgtgtgagtg caagcagaa ccaaagatgg ctttgtacg    540
gggatggttc cattcgcccg aaaccttacc aagaccaatg cctcacctct cagggagact    600
ccgttagatc cgtaatcaat ttatttagct gcaccgctgg atcgccaagg caacgatggg    660
tatttaccaa taaaggggcc attttgaatt taaagaatag gttggccatg gatgtggcgg    720
aatcaaatcc aagcctccgc cgaataatca tcttttcagt cactggaaat ccaaatcaaa    780
tgtggcttcc cgtgcca                                                   797
```

<210> SEQ ID NO 8
<211> LENGTH: 266
<212> TYPE: PRT
<213> ORGANISM: Viscum album coloratum
<220> FEATURE:
<221> NAME/KEY: misc_feature

<400> SEQUENCE: 8

-continued

```
Asp Asp Val Thr Cys Thr Thr Ser Glu Pro Thr Val Arg Phe Val Gly
 1               5                  10                 15
Arg Asn Gly Leu Cys Leu Asp Val Pro Glu Gly Asp Tyr His Asp Gly
             20                  25                  30
Ser Arg Ile Gln Leu Trp Pro Cys Lys Ser Asn Ser Asp Gln Asn Gln
         35                  40                  45
Leu Trp Thr Ile Arg Arg Asp Gly Thr Ile Arg Ser Asn Gly Arg Cys
 50                  55                  60
Leu Thr Thr Tyr Gly Tyr Thr Ala Gly Ser Tyr Ile Met Ile Tyr Asp
 65                  70                  75                  80
Cys Asn Arg Gly Gly Trp Asp Leu Thr Thr Trp Gln Ile Arg Gly Asn
                 85                  90                  95
Gly Ile Ile Leu Asn Pro Arg Ser Met Met Val Ile Gly Thr Pro Ser
                100                 105                 110
Gly Ser Arg Gly Thr Arg Gly Thr Thr Phe Thr Leu Gln Thr Leu Gly
            115                 120                 125
Tyr Ser Leu Gly Gln Gly Trp Leu Ala Ser Asn Asp Thr Ala Pro Arg
        130                 135                 140
Glu Val Thr Ile Tyr Gly Phe Arg Asp His Cys Met Glu Thr Ser Gly
145                 150                 155                 160
Gly Lys Val Trp Val Gly Thr Cys Val Ser Gly Lys Gln Asn Gln Arg
                165                 170                 175
Trp Ala Leu Tyr Gly Asp Gly Ser Ile Arg Pro Lys Pro Tyr Gln Asp
                180                 185                 190
Gln Cys Leu Thr Ser Gln Gly Asp Ser Val Arg Ser Val Ile Asn Leu
            195                 200                 205
Phe Ser Cys Thr Ala Gly Ser Pro Arg Gln Arg Trp Val Phe Thr Asn
        210                 215                 220
Lys Gly Ala Ile Leu Asn Leu Lys Asn Arg Leu Ala Met Asp Val Ala
225                 230                 235                 240
Glu Ser Asn Pro Ser Leu Arg Arg Ile Ile Ile Phe Ser Val Thr Gly
                245                 250                 255
Asn Pro Asn Gln Met Trp Leu Pro Val Pro
            260                 265
```

<210> SEQ ID NO 9
<211> LENGTH: 789
<212> TYPE: DNA
<213> ORGANISM: Viscum album coloratum
<220> FEATURE:
<221> NAME/KEY: misc_feature

<400> SEQUENCE: 9

| | | | | | |
|---|---|---|---|---|---|
| gacgatggta | cctgcactgc | ttccgaacct | acggtgcgga | ttgtgggtct | aaatggcctg | 60 |
| tgcgtcgacg | tccgaaatgg | aaaattccac | gatggaaatc | cgatacagtt | gtggccctgc | 120 |
| aagtccaaca | ccgataggaa | tcagctgtgg | acgatcagaa | gggatggaac | cattcgatct | 180 |
| aatagcaagt | gcttgaccac | ctatggctat | cgtgatggca | tgtatgtaat | gatctacaac | 240 |
| tgtaatacgg | ccgtgcggga | ggccactatt | tggcaaatat | gggaaaatgg | aaccatcgtt | 300 |
| aatccaagat | ccagtctggt | actgggagca | gcatctggaa | acagccgcac | taggcttact | 360 |
| gtgcaaacac | aggcttactc | gttgggacag | ggctggcttg | ccagcaatga | taccgcccct | 420 |
| cgcgaggtaa | cctatacgg | attccgtgac | ctttgcatgg | aagctaatgg | atcgagtgtg | 480 |
| tgggtggaga | cttgtgtgag | taacaagcag | aaccaaaaat | gggctttgta | cggggatggt | 540 |

```
tctatacgcc ccaaacaaaa ccgaaaccaa tgcctcacct gccagaaaga ctccgtttca    600
accgtaatca atattgttag ctgcagcgca ggatcgtctg ggcagcgatg ggtgtttacc    660
aataaaggga ccattttgaa tttaaagaat gggttggtca tggatgtggc gcaatcaaat    720
ccaagcctcc gccgaataat catctaccca gccaccggaa agcctaatca atgtggctt     780 cccgtgcca                                                            789
```

<210> SEQ ID NO 10
<211> LENGTH: 263
<212> TYPE: PRT
<213> ORGANISM: Viscum album coloratum
<220> FEATURE:
<221> NAME/KEY: misc_feature

<400> SEQUENCE: 10

```
Asp Asp Gly Thr Cys Thr Ala Ser Glu Pro Thr Val Arg Ile Val Gly
 1               5                  10                  15

Leu Asn Gly Leu Cys Val Asp Val Arg Asn Gly Lys Phe His Asp Gly
            20                  25                  30

Asn Pro Ile Gln Leu Trp Pro Cys Lys Ser Asn Thr Asp Arg Asn Gln
        35                  40                  45

Leu Trp Thr Ile Arg Arg Asp Gly Thr Ile Arg Ser Asn Ser Lys Cys
    50                  55                  60

Leu Thr Thr Tyr Gly Tyr Arg Asp Gly Met Tyr Val Met Ile Tyr Asn
65                  70                  75                  80

Cys Asn Thr Ala Val Arg Glu Ala Thr Ile Trp Gln Ile Trp Glu Asn
                85                  90                  95

Gly Thr Ile Val Asn Pro Arg Ser Ser Leu Val Leu Gly Ala Ala Ser
            100                 105                 110

Gly Asn Ser Arg Thr Arg Leu Thr Val Gln Thr Gln Ala Tyr Ser Leu
        115                 120                 125

Gly Gln Gly Trp Leu Ala Ser Asn Asp Thr Ala Pro Arg Glu Val Thr
    130                 135                 140

Ile Tyr Gly Phe Arg Asp Leu Cys Met Glu Ala Asn Gly Ser Ser Val
145                 150                 155                 160

Trp Val Glu Thr Cys Val Ser Asn Lys Gln Asn Gln Lys Trp Ala Leu
                165                 170                 175

Tyr Gly Asp Gly Ser Ile Arg Pro Lys Gln Asn Arg Asn Gln Cys Leu
            180                 185                 190

Thr Cys Gln Lys Asp Ser Val Thr Val Ile Asn Ile Val Ser Cys
        195                 200                 205

Ser Ala Gly Ser Ser Gly Gln Arg Trp Val Phe Thr Asn Lys Gly Thr
    210                 215                 220

Ile Leu Asn Leu Lys Asn Gly Leu Val Met Asp Val Ala Gln Ser Asn
225                 230                 235                 240

Pro Ser Leu Arg Arg Ile Ile Tyr Pro Ala Thr Gly Lys Pro Asn
                245                 250                 255

Gln Met Trp Leu Pro Val Pro
            260
```

<210> SEQ ID NO 11
<211> LENGTH: 789
<212> TYPE: DNA
<213> ORGANISM: Viscum album coloratum
<220> FEATURE:
<221> NAME/KEY: misc_feature

```
<400> SEQUENCE: 11
gacgatggaa cctgcactcc ttccgaacct acggtgtgga ttgtgggtct aaatggcctg      60
tgcgtcgacg tccgacatgg aaaattccac gatggaaatc cgatacagtt gtggccctgc     120
aagtccaaca ccgataggaa tcagctgtgg acgatcagaa gggatggaac cattcgatct     180
aatagcaagt gcttgaccac ctatggctat cgtgatggca tgtatgtcat gatctacaac     240
tgtaatacgg ccgtgcggga ggccactatt tggcaaatat gggaaaatgg aaccatcgtt     300
aatccaaaat ccagtctggt actgggagca gcatctggaa gcagccgcac tacgcttact     360
gtgcaaacac aggcttactc gttgggacag gctggcttg ccagccatga tacagccct       420 cgcgaggtaa ccatatacgg tttccgtgac ctttgcatgg aagctaatgg atcgagtgtg     480
tkggtggaga cttgtgtgag tcacaagcag aaccaaaaat gggctttgta cggggatggt     540
tctatacgcc caaacaaaa ccgaaaccaa tgcctcacct gccagaaaga ctccgtttca      600
accgtaatca atattgttag ctgcagcgca ggatcgtctg ggcagcgatg ggtgtttacc     660
aataaaggga ccattttgaa tttaaagaat gggttggtcc tggatgtggc gcaatcaaat     720
ccaagcctcc gccgaataat catctaccca gccaccggaa agcctaatca aatgtggctt     780
cccgtgcca                                                             789

<210> SEQ ID NO 12
<211> LENGTH: 263
<212> TYPE: PRT
<213> ORGANISM: Viscum album coloratum
<220> FEATURE:
<221> NAME/KEY: misc_feature
<222> LOCATION: 161
<223> OTHER INFORMATION: Xaa = any amino acid

<400> SEQUENCE: 12

Asp Asp Gly Thr Cys Thr Pro Ser Glu Pro Thr Val Trp Ile Val Gly
 1               5                  10                  15

Leu Asn Gly Leu Cys Val Asp Val Arg His Gly Lys Phe His Asp Gly
             20                  25                  30

Asn Pro Ile Gln Leu Trp Pro Cys Lys Ser Asn Thr Asp Arg Asn Gln
         35                  40                  45

Leu Trp Thr Ile Arg Arg Asp Gly Thr Ile Arg Ser Asn Ser Lys Cys
     50                  55                  60

Leu Thr Thr Tyr Gly Tyr Arg Asp Gly Met Tyr Val Met Ile Tyr Asn
 65                  70                  75                  80

Cys Asn Thr Ala Val Arg Glu Ala Thr Ile Trp Gln Ile Trp Glu Asn
                 85                  90                  95

Gly Thr Ile Val Asn Pro Lys Ser Ser Leu Val Leu Gly Ala Ala Ser
            100                 105                 110

Gly Ser Ser Arg Thr Thr Leu Thr Val Gln Thr Gln Ala Tyr Ser Leu
        115                 120                 125

Gly Gln Gly Trp Leu Ala Ser His Asp Thr Ala Pro Arg Glu Val Thr
    130                 135                 140

Ile Tyr Gly Phe Arg Asp Leu Cys Met Glu Ala Asn Gly Ser Ser Val
145                 150                 155                 160

Xaa Val Glu Thr Cys Val Ser His Lys Gln Asn Gln Lys Trp Ala Leu
                165                 170                 175

Tyr Gly Asp Gly Ser Ile Arg Pro Lys Gln Asn Arg Asn Gln Cys Leu
            180                 185                 190

Thr Cys Gln Lys Asp Ser Val Ser Thr Val Ile Asn Ile Val Ser Cys
```

```
                195                 200                 205
Ser Ala Gly Ser Ser Gly Gln Arg Trp Val Phe Thr Asn Lys Gly Thr
    210                 215                 220

Ile Leu Asn Leu Lys Asn Gly Leu Val Leu Asp Val Ala Gln Ser Asn
225                 230                 235                 240

Pro Ser Leu Arg Arg Ile Ile Ile Tyr Pro Ala Thr Gly Lys Pro Asn
                245                 250                 255

Gln Met Trp Leu Pro Val Pro
            260

<210> SEQ ID NO 13
<211> LENGTH: 357
<212> TYPE: DNA
<213> ORGANISM: Viscum album coloratum
<220> FEATURE:
<221> NAME/KEY: misc_feature
<222> LOCATION: 19, 57, 190, 331
<223> OTHER INFORMATION: "n" = any single nucleotide

<400> SEQUENCE: 13
gccagattca atcccatcnt gtggaggctt cgccggcaaa ttaacagtgg ggagtcntct      60
ccaccaaaca tgtacatgct cgagctggag acgagttggg gtcgacaatc cacccaagtc    120
cagcagtcca aggatggcat ttttaatacc caaataagat tgcagatttc cgccggtaac    180
tttgtgacgn tgagcaatgt tcgcgacgtg atctccagct tggcgatcat gttgttcgaa    240
tgcagtggtc ggccattctc ctctctcgac cacccttcgc cgctgctcct aaggtccgtc    300
gtggatgcgg ccaacgatgt cacctgcact ntttccgaac ccaccgtgcg catcgta       357

<210> SEQ ID NO 14
<211> LENGTH: 119
<212> TYPE: PRT
<213> ORGANISM: Viscum album coloratum
<220> FEATURE:
<221> NAME/KEY: misc_feature
<222> LOCATION: 7, 64, 111
<223> OTHER INFORMATION: Xaa = any amino acid

<400> SEQUENCE: 14

Ala Arg Phe Asn Pro Ile Xaa Trp Arg Leu Arg Arg Gln Ile Asn Ser
1               5                   10                  15

Gly Glu Ser Ser Pro Pro Asn Met Tyr Met Leu Glu Leu Glu Thr Ser
            20                  25                  30

Trp Gly Arg Gln Ser Thr Gln Val Gln Gln Ser Lys Asp Gly Ile Phe
        35                  40                  45

Asn Thr Gln Ile Arg Leu Gln Ile Ser Ala Gly Asn Phe Val Thr Xaa
    50                  55                  60

Ser Asn Val Arg Asp Val Ile Ser Ser Leu Ala Ile Met Leu Phe Glu
65                  70                  75                  80

Cys Ser Gly Arg Pro Phe Ser Ser Leu Asp His Pro Ser Pro Leu Leu
                85                  90                  95

Leu Arg Ser Val Val Asp Ala Ala Asn Asp Val Thr Cys Thr Xaa Ser
            100                 105                 110

Glu Pro Thr Val Arg Ile Val
        115

<210> SEQ ID NO 15
<211> LENGTH: 837
<212> TYPE: DNA
<213> ORGANISM: Viscum album coloratum
```

-continued

<400> SEQUENCE: 15

```
catcagacga cgggcgacga atatttccgg ttcatcacgc ttctccgaga ttatgtctca    60
agcggaagct tttccaatga gataccactc ttgcgtcagt ctacgatccc cgtctcggat   120
gcgcaaagat ttgtgttggt ggaactcacc aatcaggggg gagactcgat cacggccgcc   180
atcgacgtta ccaatctgta cgtggtggct taccaagcag gcgaccaatc ctactttttg   240
cgcgacgcac cagacggcgc ggaaaggcat ctcttcaccg gcaccaccag atcctctctc   300
ccattcaccg gaagctacac agatctggag cgatacgccg tcataggga ccagatccct   360
ctgggtatag aggaactcat tcaatccgtc tcggcgcttc gttatccagg cggcagcacc   420
cgggcccaag ctcgttccct tataatcctc attcagatga tctccgaggc cgcgagattc   480
aatcccatct tttggagggc tcgccaatac attaacagcg gggagtcatt tcttcccgac   540
atgtacatgc tcgagctgga gactagttgg ggccaacaat ccacgcaagt ccagcagtct   600
acggatggcg ttttaataa cccatttcgg ttgggtatat ccaccggtaa cttcgtgacg   660
ttgagcaatg ttcgcgacgt gatcgccagc ttagcgatca tgttgtttgt atgtagggac   720
cgaccatctt cctccgacgt gcgctattgg ccgctggtca tacgaccgt cttggaaaat   780
agcggcgccg tcgacgatgt tacctgcact gcttccgaac ccaccgtgcg catcgta     837
```

<210> SEQ ID NO 16
<211> LENGTH: 279
<212> TYPE: PRT
<213> ORGANISM: Viscum album coloratum

<400> SEQUENCE: 16

```
His Gln Thr Thr Gly Asp Glu Tyr Phe Arg Phe Ile Thr Leu Leu Arg
  1               5                  10                  15

Asp Tyr Val Ser Ser Gly Ser Phe Ser Asn Glu Ile Pro Leu Leu Arg
             20                  25                  30

Gln Ser Thr Ile Pro Val Ser Asp Ala Gln Arg Phe Val Leu Val Glu
         35                  40                  45

Leu Thr Asn Gln Gly Gly Asp Ser Ile Thr Ala Ala Ile Asp Val Thr
     50                  55                  60

Asn Leu Tyr Val Val Ala Tyr Gln Ala Gly Asp Gln Ser Tyr Phe Leu
 65                  70                  75                  80

Arg Asp Ala Pro Asp Gly Ala Glu Arg His Leu Phe Thr Gly Thr Thr
                 85                  90                  95

Arg Ser Ser Leu Pro Phe Thr Gly Ser Tyr Thr Asp Leu Glu Arg Tyr
            100                 105                 110

Ala Gly His Arg Asp Gln Ile Pro Leu Gly Ile Glu Glu Leu Ile Gln
        115                 120                 125

Ser Val Ser Ala Leu Arg Tyr Pro Gly Gly Ser Thr Arg Ala Gln Ala
    130                 135                 140

Arg Ser Leu Ile Ile Leu Ile Gln Met Ile Ser Glu Ala Ala Arg Phe
145                 150                 155                 160

Asn Pro Ile Phe Trp Arg Ala Arg Gln Tyr Ile Asn Ser Gly Glu Ser
                165                 170                 175

Phe Leu Pro Asp Met Tyr Met Leu Glu Leu Glu Thr Ser Trp Gly Gln
            180                 185                 190

Gln Ser Thr Gln Val Gln Gln Ser Thr Asp Gly Val Phe Asn Asn Pro
        195                 200                 205

Phe Arg Leu Gly Ile Ser Thr Gly Asn Phe Val Thr Leu Ser Asn Val
```

-continued

```
            210                 215                 220
Arg Asp Val Ile Ala Ser Leu Ala Ile Met Leu Phe Val Cys Arg Asp
225                 230                 235                 240

Arg Pro Ser Ser Asp Val Arg Tyr Trp Pro Leu Val Ile Arg Pro
                245                 250                 255

Val Leu Glu Asn Ser Gly Ala Val Asp Asp Val Thr Cys Thr Ala Ser
            260                 265                 270

Glu Pro Thr Val Arg Ile Val
        275

<210> SEQ ID NO 17
<211> LENGTH: 18
<212> TYPE: DNA
<213> ORGANISM: Viscum album coloratum
<220> FEATURE:
<221> NAME/KEY: misc_feature
<222> LOCATION: 3, 6, 12, 16
<223> OTHER INFORMATION: n = inosine

<400> SEQUENCE: 17
gtnacncatc anaacngg                                                        18

<210> SEQ ID NO 18
<211> LENGTH: 19
<212> TYPE: DNA
<213> ORGANISM: Viscum album coloratum
<220> FEATURE:
<221> NAME/KEY: misc_feature
<222> LOCATION: 3, 6, 13, 16
<223> OTHER INFORMATION: n = inosine

<400> SEQUENCE: 18
acnatncgca cngtnggtc                                                       19

<210> SEQ ID NO 19
<211> LENGTH: 29
<212> TYPE: PRT
<213> ORGANISM: Viscum album coloratum
<220> FEATURE:
<221> NAME/KEY: misc_feature

<400> SEQUENCE: 19

Tyr Glu Arg Glu Lys Leu Arg Val Thr His Gln Thr Thr Gly Asp Gln
1               5                   10                  15

Tyr Phe Lys Phe Ile Thr Leu Leu Ala Asp Gln His Ser
            20                  25

<210> SEQ ID NO 20
<211> LENGTH: 28
<212> TYPE: PRT
<213> ORGANISM: Viscum album coloratum
<220> FEATURE:
<221> NAME/KEY: misc_feature

<400> SEQUENCE: 20

Tyr Glu Arg Glu Lys Leu Arg Val Thr His Gln Thr Thr Gly Asp Glu
1               5                   10                  15

Tyr Phe Arg Phe Ile Thr Leu Leu Ala Asp Thr Val
            20                  25

<210> SEQ ID NO 21
<211> LENGTH: 30
<212> TYPE: PRT
<213> ORGANISM: Viscum album loranthacea
```

```
<220> FEATURE:
<221> NAME/KEY: misc_feature

<400> SEQUENCE: 21

Tyr Glu Arg Glu Lys Leu Arg Val Thr His Gln Thr Thr Gly Asp Glu
1               5                   10                  15

Tyr Phe Arg Phe Ile Thr Leu Leu Ala Asp Thr Val Ser Ser
            20                  25                  30

<210> SEQ ID NO 22
<211> LENGTH: 13
<212> TYPE: PRT
<213> ORGANISM: Viscum album coloratum
<220> FEATURE:
<221> NAME/KEY: misc_feature
<222> LOCATION: 4
<223> OTHER INFORMATION: Xaa = any amino acid

<400> SEQUENCE: 22

Asp Val Thr Xaa Thr Ala Ser Glu Pro Thr Val Arg Ile
1               5                   10

<210> SEQ ID NO 23
<211> LENGTH: 20
<212> TYPE: PRT
<213> ORGANISM: Viscum album loranthacea
<220> FEATURE:
<221> NAME/KEY: misc_feature

<400> SEQUENCE: 23

Asp Asp Val Thr Ser Ser Ala Ser Glu Pro Thr Val Arg Ile Val Gly
1               5                   10                  15

Arg Asn Gly Met
            20

<210> SEQ ID NO 24
<211> LENGTH: 10
<212> TYPE: PRT
<213> ORGANISM: Viscum album coloratum
<220> FEATURE:
<221> NAME/KEY: misc_feature

<400> SEQUENCE: 24

Tyr Glu Arg Leu Lys Leu Tyr Val Thr His
1               5                   10

<210> SEQ ID NO 25
<211> LENGTH: 28
<212> TYPE: PRT
<213> ORGANISM: Viscum album coloratum
<220> FEATURE:
<221> NAME/KEY: misc_feature

<400> SEQUENCE: 25

Tyr Glu Arg Leu Arg Leu Arg Val Thr His Gln Thr Thr Gly Asp Glu
1               5                   10                  15

Tyr Phe Arg Phe Ile Thr Leu Leu Arg Asp Tyr Val
            20                  25

<210> SEQ ID NO 26
<211> LENGTH: 17
<212> TYPE: PRT
<213> ORGANISM: Viscum album coloratum
<220> FEATURE:
<221> NAME/KEY: misc_feature
```

-continued

<210> SEQ ID NO 26 (continued)

<400> SEQUENCE: 26

His Gln Thr Thr Gly Asp Glu Tyr Phe Arg Phe Ile Thr Leu Leu Arg
1               5                   10                  15
Asp

<210> SEQ ID NO 27
<211> LENGTH: 26
<212> TYPE: PRT EMLA
<213> ORGANISM: Viscum album loranthacea
<220> FEATURE:
<221> NAME/KEY: misc_feature

<400> SEQUENCE: 27

Tyr Glu Arg Leu Lys Leu Tyr Val Thr His Gln Thr Thr Gly Glu Glu
1               5                   10                  15
Tyr Phe Arg Phe Ile Thr Leu Leu Arg Asp
                20                  25

<210> SEQ ID NO 28
<211> LENGTH: 30
<212> TYPE: PRT
<213> ORGANISM: Viscum album coloratum
<220> FEATURE:
<221> NAME/KEY: misc_feature

<400> SEQUENCE: 28

Ile Phe Pro Lys Gln Tyr Pro Ile Ile Asn Phe Thr Thr Ala Gly Ala
1               5                   10                  15
Thr Val Gln Ser Tyr Thr Asn Phe Ile Arg Ala Val Arg Gly
                20                  25                  30

<210> SEQ ID NO 29
<211> LENGTH: 26
<212> TYPE: PRT
<213> ORGANISM: Viscum album coloratum
<220> FEATURE:
<221> NAME/KEY: misc_feature

<400> SEQUENCE: 29

Glu Asp Arg Pro Ile Lys Phe Ser Arg Glu Gly Ala Thr Ser Gln Ser
1               5                   10                  15
Tyr Lys Gln Phe Ile Glu Ala Leu Arg Glu

<210> SEQ ID NO 30
<211> LENGTH: 2
<212> TYPE: PRT
<213> ORGANISM: Viscum album coloratum
<220> FEATURE:
<221> NAME/KEY: misc_feature

<400> SEQUENCE: 30

Tyr Val
1

<210> SEQ ID NO 31
<211> LENGTH: 29
<212> TYPE: PRT
<213> ORGANISM: Viscum album coloratum
<220> FEATURE:
<221> NAME/KEY: misc_feature

<400> SEQUENCE: 31

Tyr Val Ser Ser Gly Ser Phe Ser Asn Glu Ile Pro Leu Leu Arg Gln
1               5                   10                  15

-continued

```
Ser Thr Ile Pro Val Ser Asp Ala Gln Arg Phe Val Leu
            20                  25

<210> SEQ ID NO 32
<211> LENGTH: 29
<212> TYPE: PRT
<213> ORGANISM: Viscum album loranthacea
<220> FEATURE:
<221> NAME/KEY: misc_feature

<400> SEQUENCE: 32

Tyr Val Ser Ser Gly Ser Pro Ser Asn Glu Ile Pro Leu Leu Arg Gln
1               5                   10                  15
Ser Thr Ile Pro Val Ser Asp Ala Gln Arg Phe Val Leu
            20                  25

<210> SEQ ID NO 33
<211> LENGTH: 29
<212> TYPE: PRT
<213> ORGANISM: Viscum album coloratum
<220> FEATURE:
<221> NAME/KEY: misc_feature

<400> SEQUENCE: 33

Arg Leu Thr Thr Gly Ala Asp Val Arg His Glu Ile Pro Val Leu Pro
1               5                   10                  15

Asn Arg Val Gly Leu Pro Ile Asn Gln Arg Phe Ile Leu
            20                  25

<210> SEQ ID NO 34
<211> LENGTH: 27
<212> TYPE: PRT
<213> ORGANISM: Viscum album coloratum
<220> FEATURE:
<221> NAME/KEY: misc_feature

<400> SEQUENCE: 34

Arg Leu Arg Gly Gly Leu Ile His Asp Ile Pro Val Leu Pro Asp Pro
1               5                   10                  15

Thr Thr Leu Gln Glu Arg Leu Arg Tyr Ile Thr
            20                  25

<210> SEQ ID NO 35
<211> LENGTH: 29
<212> TYPE: PRT
<213> ORGANISM: Viscum album coloratum
<220> FEATURE:
<221> NAME/KEY: misc_feature

<400> SEQUENCE: 35

Val Glu Leu Thr Asn Gln Gly Gly Asp Ser Ile Thr Ala Ala Ile Asp
1               5                   10                  15

Val Thr Asn Leu Tyr Val Val Ala Tyr Gln Ala Gly Asp
            20                  25

<210> SEQ ID NO 36
<211> LENGTH: 29
<212> TYPE: PRT
<213> ORGANISM: Viscum album loranthacea
<220> FEATURE:
<221> NAME/KEY: misc_feature

<400> SEQUENCE: 36

Val Glu Leu Thr Asn Gln Gly Gln Asp Ser Val Thr Thr Ala Ile Asp
```

```
                 1               5                  10                 15
Val Thr Asn Ala Tyr Val Val Ala Tyr Gln Ala Gly Asp
            20                  25

<210> SEQ ID NO 37
<211> LENGTH: 29
<212> TYPE: PRT
<213> ORGANISM: Viscum album coloratum
<220> FEATURE:
<221> NAME/KEY: misc_feature

<400> SEQUENCE: 37

Val Glu Leu Ser Asn His Ala Glu Leu Ser Val Thr Leu Ala Leu Asp
1               5                  10                 15
Val Thr Asn Ala Tyr Val Val Gly Tyr Arg Ala Gly Asn
            20                  25

<210> SEQ ID NO 38
<211> LENGTH: 29
<212> TYPE: PRT
<213> ORGANISM: Viscum album coloratum
<220> FEATURE:
<221> NAME/KEY: misc_feature

<400> SEQUENCE: 38

Val Glu Leu Ser Asn Ser Asp Thr Glu Ser Ile Glu Val Gly Ile Asp
1               5                  10                 15
Val Thr Asn Ala Tyr Val Val Ala Tyr Arg Ala Gly Thr
            20                  25

<210> SEQ ID NO 39
<211> LENGTH: 22
<212> TYPE: PRT
<213> ORGANISM: Viscum album coloratum
<220> FEATURE:
<221> NAME/KEY: misc_feature

<400> SEQUENCE: 39

Gln Ser Tyr Phe Leu Arg Asp Ala Pro Asp Gly Ala Glu Arg His Leu
1               5                  10                 15
Phe Thr Gly Thr Thr Arg
            20

<210> SEQ ID NO 40
<211> LENGTH: 22
<212> TYPE: PRT
<213> ORGANISM: Viscum album loranthacea
<220> FEATURE:
<221> NAME/KEY: misc_feature

<400> SEQUENCE: 40

Gln Ser Tyr Phe Leu Arg Asp Ala Pro Arg Gly Ala Glu Thr His Leu
1               5                  10                 15
Phe Thr Gly Thr Thr Arg
            20

<210> SEQ ID NO 41
<211> LENGTH: 26
<212> TYPE: PRT
<213> ORGANISM: Viscum album coloratum
<220> FEATURE:
<221> NAME/KEY: misc_feature

<400> SEQUENCE: 41
```

```
Ser Ala Tyr Phe Phe His Pro Asp Asn Gln Glu Asp Ala Glu Ala Ile
1               5                   10                  15

Thr His Leu Phe Thr Asp Val Gln Asn Arg
            20                  25
```

<210> SEQ ID NO 42
<211> LENGTH: 23
<212> TYPE: PRT
<213> ORGANISM: Viscum album coloratum
<220> FEATURE:
<221> NAME/KEY: misc_feature

<400> SEQUENCE: 42

```
Gln Ser Tyr Phe Leu Arg Asp Ala Pro Ser Ser Ala Ser Asp Tyr Leu
1               5                   10                  15

Phe Thr Gly Thr Asp Gln His
            20
```

<210> SEQ ID NO 43
<211> LENGTH: 25
<212> TYPE: PRT
<213> ORGANISM: Viscum album coloratum
<220> FEATURE:
<221> N -continued Ser Leu Pro Phe Tyr Gly Thr Tyr Gly Asp Leu Glu Arg Trp Ala His
1               5                   10                  15

Gln Ser Arg Gln Gln Ile Pro Leu Gly Leu Asp
            20                  25

<210> SEQ ID NO 47
<211> LENGTH: 24
<212> TYPE: PRT
<213> ORGANISM: Viscum album coloratum
<220> FEATURE:
<221> NAME/KEY: misc_feature

<400> SEQUENCE: 47

Ile Glu Glu Leu Ile Gln Ser Val Ser Ala Leu Ile Tyr Pro Gly Gly
1               5                   10                  15

Ser Thr Arg Ala Gln Ala Arg Ser
            20

<210> SEQ ID NO 48
<211> LENGTH: 24
<212> TYPE: PRT
<213> ORGANISM: Viscum album loranthacea
<220> FEATURE:
<221> NAME/KEY: misc_feature

<400> SEQUENCE: 48

Ile Arg Gln Leu Ile Gln Ser Val Thr Ala Leu Ile Phe Pro Gly Gly
1               5                   10                  15

Ser Thr Arg Thr Gln Ala Arg Ser
            20

<210> SEQ ID NO 49
<211> LENGTH: 25
<212> TYPE: PRT
<213> ORGANISM: Ricin toxin
<220> FEATURE:
<221> NAME/KEY: misc_feature

<400> SEQUENCE: 49

Pro Leu Glu Glu Ala Ile Ser Ala Leu Tyr Tyr Tyr Ser Tyr Gly Gly
1               5                   10                  15

Thr Gln Leu Pro Thr Leu Ala Arg Ser
            20                  25

<210> SEQ ID NO 50
<211> LENGTH: 22
<212> TYPE: PRT
<213> ORGANISM: Arbin
<220> FEATURE:
<221> NAME/KEY: misc_feature

<400> SEQUENCE: 50

Ala Leu Thr His Gly Thr Ser Phe Phe Arg Ser Gly Gly Asn Arg Asn
1               5                   10                  15

Glu Glu Lys Ala Arg Thr
            20

<210> SEQ ID NO 51
<211> LENGTH: 19
<212> TYPE: PRT
<213> ORGANISM: Viscum album coloratum
<220> FEATURE:
<221> NAME/KEY: misc_feature
<222> LOCATION: 7

-continued

<223> OTHER INFORMATION: Xaa = any amino acid

<400> SEQUENCE: 51

Ala Arg Phe Asn Pro Ile Xaa Trp Arg Leu Arg Arg Gln Ile Asn Ser
1               5                   10                  15

Gly Glu Ser

<210> SEQ ID NO 52
<211> LENGTH: 30
<212> TYPE: PRT
<213> ORGANISM: Viscum album coloratum
<220> FEATURE:
<221> NAME/KEY: misc_feature

<400> SEQUENCE: 52

Leu Ile Ile Leu Ile Gln Met Ile Ser Glu Ala Ala Arg Phe Asn Pro
1               5                   10                  15

Ile Phe Trp Arg Ala Arg Gln Tyr Ile Asn Ser Gly Glu Ser
            20                  25                  30

<210> SEQ ID NO 53
<211> LENGTH: 30
<212> TYPE: PRT
<213> ORGANISM: Viscum album loranthacea
<220> FEATURE:
<221> NAME/KEY: misc_feature

<400> SEQUENCE: 53

Ile Leu Ile Leu Ile Gln Met Ile Ser Glu Ala Ala Arg Phe Asn Pro
1               5                   10                  15

Ile Leu Trp Arg Tyr Arg Gln Tyr Ile Asn Ser Gly Ala Ser
            20                  25                  30

<210> SEQ ID NO 54
<211> LENGTH: 30
<212> TYPE: PRT
<213> ORGANISM: Risin toxin
<220> FEATURE:
<221> NAME/KEY: misc_feature

<400> SEQUENCE: 54

PHE ILE ILE CYS ILE GLN MET ILE SER GLU ALA ALA ARG PHE GLN
                5                   10                  15

TYR ILE GLU GLY GLU MET ARG THR ARG ILE ARG TYR ASN ARG ARG
            20                  25                  30

<210> SEQ ID NO 55
<211> LENGTH: 30
<212> TYPE: PRT
<213> ORGANISM: Abrin
<220> FEATURE:
<221> NAME/KEY: misc_feature

<400> SEQUENCE: 55

LEU ILE VAL ILE ILE GLN MET VAL ALA GLU ALA ALA ARG PHE ARG
                5                   10                  15

TYR ILE SER ASN ARG VAL ARG VAL SER ILE GLN THR GLY THR ALA
            20                  25                  30

<210> SEQ ID NO 56
<211> LENGTH: 29
<212> TYPE: PRT
<213> ORGANISM: Viscum album coloratum
<220> FEATURE:

-continued

<221> NAME/KEY: misc_feature

<400> SEQUENCE: 56

SER SER PRO PRO ASN TYR MET LEU GLU LEU GLU THR SER TRP GLY
                 5                  10                 15

ARG GLN SER THR GLN VAL GLN GLN SER LYS ASP GLY ILE PHE
             20                  25

<210> SEQ ID NO 57
<211> LENGTH: 29
<212> TYPE: PRT
<213> ORGANISM: Viscum album coloratum
<220> FEATURE:
<221> NAME/KEY: misc_feature

<400> SEQUENCE: 57

PHE LEU PRO ASP MET TYR MET LEU GLU LEU GLU THR SER TRP GLY
                 5                  10                 15

GLN GLN SER THR GLN VAL GLN GLN SER THR ASP GLY VAL PHE
             20                  25

<210> SEQ ID NO 58
<211> LENGTH: 29
<212> TYPE: PRT
<213> ORGANISM: Viscum album loranthacea
<220> FEATURE:
<221> NAME/KEY: misc_feature

<400> SEQUENCE: 58

PHE LEU PRO ASP VAL TYR MET LEU GLU LEU GLU THR SER TRP GLY
                 5                  10                 15

GLN GLN SER THR GLN VAL GLN HIS SER THR ASP GLY VAL PHE
             20                  25

<210> SEQ ID NO 59
<211> LENGTH: 29
<212> TYPE: PRT
<213> ORGANISM: Risin toxin
<220> FEATURE:
<221> NAME/KEY: misc_feature

<400> SEQUENCE: 59

SER ALA PRO ASP PRO SER VAL ILE THR LEU GLU ASN SER TRP GLY
                 5                  10                 15

ARG LEU SER THR ALA ILE GLN GLU SER ASN GLN GLY ALA PHE
             20                  25

<210> SEQ ID NO 60
<211> LENGTH: 29
<212> TYPE: PRT
<213> ORGANISM: Arbin
<220> FEATURE:
<221> NAME/KEY: misc_feature

<400> SEQUENCE: 60

PHE GLN PRO ASP ALA ALA MET ILE SER LEU GLU ASN MET TRP ASP
                 5                  10                 15

ASN LEU SER ARG GLY VAL GLN GLU SER VAL GLN ASP THR PHE
             20                  25

<210> SEQ ID NO 61
<211> LENGTH: 24
<212> TYPE: PRT
<213> ORGANISM: Viscum album coloratum

```
<220> FEATURE:
<221> NAME/KEY: misc_feature
<222> LOCATION: 17
<223> OTHER INFORMATION: Xaa = any amino acid

<400> SEQUENCE: 61

ASN THR GLN ILE ARG LEU GLN ILE SER ALA GLY MET PHE VAL THR
                5                   10                  15
SER Xaa ASN VAL ARG ASP VAL ILE SER
            20

<210> SEQ ID NO 62
<211> LENGTH: 24
<212> TYPE: PRT
<213> ORGANISM: Viscum album coloratum
<220> FEATURE:
<221> NAME/KEY: misc_feature

<400> SEQUENCE: 62

ASN ASN PRO PHE ARG LEU GLY ILE SER THR GLY MET PHE VAL THR
                5                   10                  15
LEU SER ASN VAL ARG ASP VAL ILE ALA
            20

<210> SEQ ID NO 63
<211> LENGTH: 24
<212> TYPE: PRT
<213> ORGANISM: Viscum album loranthacea
<220> FEATURE:
<221> NAME/KEY: misc_feature

<400> SEQUENCE: 63

ASN ASN PHE ILE ARG LEU ALA ILE PHE PHE GLY MET PHE VAL THR
                5                   10                  15
LEU THR ASN VAL ARG ASP VAL ILE ALA
            20

<210> SEQ ID NO 64
<211> LENGTH: 24
<212> TYPE: PRT
<213> ORGANISM: Risin toxin
<220> FEATURE:
<221> NAME/KEY: misc_feature

<400> SEQUENCE: 64

ALA SER PRO ILE GLN LEU GLN ARG ARG ASN GLY SER LYS PHE SER
                5                   10                  15
VAL TYR ASP VAL SER ILE LEU ILE PRO
            20

<210> SEQ ID NO 65
<211> LENGTH: 25
<212> TYPE: PRT
<213> ORGANISM: Abrin
<220> FEATURE:
<221> NAME/KEY: misc_feature

<400> SEQUENCE: 65

PHE ASN GLN VAL THR LEU THR ASN ILE ARG ASN GLU PRO VAL ILE
                5                   10                  15
VAL ASP SER LEU SER HIS PRO THR VAL ALA
            20                  25

<210> SEQ ID NO 66
```

```
<211> LENGTH: 16
<212> TYPE: PRT
<213> ORGANISM: Viscum album coloratum
<220> FEATURE:
<221> NAME/KEY: misc_feature

<400> SEQUENCE: 66

SER LEU ALA ILE MET LEU PHE GLU CYS SER GLY ARG PRO PHE SER
                5                   10                  15

SER

<210> SEQ ID NO 67
<211> LENGTH: 16
<212> TYPE: PRT
<213> ORGANISM: Viscum album coloratum
<220> FEATURE:
<221> NAME/KEY: misc_feature

<400> SEQUENCE: 67

SER LEU ALA ILE MET LEU PHE VAL CYS ARG ASP ARG PHE SER SER
                5                   10                  15

SER

<210> SEQ ID NO 68
<211> LENGTH: 16
<212> TYPE: PRT
<213> ORGANISM: Viscum album loranthacea
<220> FEATURE:
<221> NAME/KEY: misc_feature

<400> SEQUENCE: 68

SER LEU ALA ILE MET LEU PHE VAL CYS GLY GLU ARG PHE SER SER
                5                   10                  15

SER

<210> SEQ ID NO 69
<211> LENGTH: 17
<212> TYPE: PRT
<213> ORGANISM: Risin toxin
<220> FEATURE:
<221> NAME/KEY: misc_feature

<400> SEQUENCE: 69

ILE ILE ALA LEU MET VAL TYR ARG CYS ALA PHE PHE PHE SER SER
                5                   10                  15

GLN PHE

<210> SEQ ID NO 70
<211> LENGTH: 15
<212> TYPE: PRT
<213> ORGANISM: Abrin
<220> FEATURE:
<221> NAME/KEY: misc_feature

<400> SEQUENCE: 70

VAL LEU ALA LEU MET LEU PHE VAL CYS ASN PRO PRO PRO PRO ASN
                5                   10                  15

<210> SEQ ID NO 71
<211> LENGTH: 17
<212> TYPE: PRT
<213> ORGANISM: Viscum album coloratum
<220> FEATURE:
<221> NAME/KEY: misc_feature
```

-continued

```
<400> SEQUENCE: 71

LEU ASP HIS PRO SER PRO LEU LEU LEU ARG SER VAL VAL ASP ALA
              5                  10                  15

ALA ASN

<210> SEQ ID NO 72
<211> LENGTH: 19
<212> TYPE: PRT
<213> ORGANISM: Viscum album coloratum
<220> FEATURE:
<221> NAME/KEY: misc_feature

<400> SEQUENCE: 72

ASP VAL ARG TYR TRP PRO LEU VAL ILE ARG PRO VAL LEU GLU ASN
              5                  10                  15

SER GLY ALA VAL

<210> SEQ ID NO 73
<211> LENGTH: 12
<212> TYPE: PRT
<213> ORGANISM: Risin toxin
<220> FEATURE:
<221> NAME/KEY: misc_feature

<400> SEQUENCE: 73

SER LEU LEU ILE ARG PRO VAL VAL PRO ASN PHE ASN
              5                  10

<210> SEQ ID NO 74
<211> LENGTH: 10
<212> TYPE: PRT
<213> ORGANISM: Abrin
<220> FEATURE:
<221> NAME/KEY: misc_feature

<400> SEQUENCE: 74

ALA ASN GLN SER PRO LEU LEU ILE ARG SER
              5                  10

<210> SEQ ID NO 75
<211> LENGTH: 13
<212> TYPE: PRT
<213> ORGANISM: Viscum album coloratum
<220> FEATURE:
<221> NAME/KEY: misc_feature

<400> SEQUENCE: 75

ASP VAL THR CYS THR ALA SER GLU CYS THR VAL ARG ILE
              5                  10

<210> SEQ ID NO 76
<211> LENGTH: 14
<212> TYPE: PRT
<213> ORGANISM: Viscum album coloratum
<220> FEATURE:
<221> NAME/KEY: misc_feature
<222> LOCATION: 4, 6
<223> OTHER INFORMATION: Xaa = any amino acid

<400> SEQUENCE: 76

ASP VAL THR Xaa THR Xaa SER GLU PRO THR VAL ARG ILE VAL
              5                  10

<210> SEQ ID NO 77
<211> LENGTH: 15
```

-continued

```
<212> TYPE: PRT
<213> ORGANISM: Viscum album coloratum
<220> FEATURE:
<221> NAME/KEY: misc_feature

<400> SEQUENCE: 77

ASP ASP VAL THR CYS THR ALA SER GLU PRO THR VAL ARG ILE VAL
                5                   10                  15

<210> SEQ ID NO 78
<211> LENGTH: 20
<212> TYPE: PRT
<213> ORGANISM: Viscum album loranthacea
<220> FEATURE:
<221> NAME/KEY: misc_feature

<400> SEQUENCE: 78

ASP ASP VAL THR SER SER ALA SER GLU PRO THR VAL ARG ILE VAL
                5                   10                  15

GLY ARG ASN GLY MET
                20

<210> SEQ ID NO 79
<211> LENGTH: 19
<212> TYPE: PRT
<213> ORGANISM: Risin toxin
<220> FEATURE:
<221> NAME/KEY: misc_feature

<400> SEQUENCE: 79

ALA ASP VAL CYS MET ASP PRO GLU PRO ILE VAL ARG ILE VAL GLY
                5                   10                  15

ARG ASN GLY MET

<210> SEQ ID NO 80
<211> LENGTH: 20
<212> TYPE: PRT
<213> ORGANISM: Abrin
<220> FEATURE:
<221> NAME/KEY: misc_feature

<400> SEQUENCE: 80

SER LYS ILE CYS SER SER ARG TYR GLU PRO THR VAL ARG ILE GLY
                5                   10                  15

GLY ARG ASP GLY MET
                20
```

What is claimed is:

1. A method of effectuating antitumoral activity, comprising administering to an animal in need thereof an amount of a lectin isolated from Korean mistletoe effective to enhance an anti-tumoral immune response, to reduce the size of a tumor, to inhibit tumor growth, to inhibit metastasis of a tumor, or a combination thereof, wherein the lectin is selected from the group consisting of KML-IIU having a molecular weight of 61.8 kD and KML-IIL having a molecular weight of 56.4 kD.

2. The method of claim 1, wherein said KML-IIU has the amino acid sequence SEQ ID NO: 16.

3. The method of claim 1, wherein said KML-IIL has the amino acid sequence SEQ ID NO: 14.

* * * * *